United States Patent [19]
Yanofsky

[11] Patent Number: 6,127,123
[45] Date of Patent: Oct. 3, 2000

[54] CAULIFLOWER FLORAL MERISTEM IDENTITY GENES AND METHODS OF USING SAME

[75] Inventor: Martin F. Yanofsky, San Diego, Calif.

[73] Assignee: Regents of the University of California, Oakland, Calif.

[21] Appl. No.: 09/149,976

[22] Filed: Sep. 9, 1998

Related U.S. Application Data

[62] Division of application No. 08/592,214, Jan. 26, 1996, Pat. No. 5,811,536.

[51] Int. Cl.⁷ .............................. C12Q 1/68; C12P 19/34; C07H 21/04
[52] U.S. Cl. ............................ 435/6; 435/91.2; 536/23.6; 536/24.3
[58] Field of Search ...................... 435/6, 91.2; 536/24.3, 536/23.6

[56] References Cited

PUBLICATIONS

Smyth. Current Biology. 5:361–366, 1995.
Crisp and Tapsell, "Cauliflower *Brassica oleracea*L.," *Genetic Improvement of Vegetable Crops*, 157–178 (1993).
Figdore et al., "Association of RFLP markers with trait loci affecting clubroot resistance and morphological characters in *Brassica oleracea*L., " *Euphytica* 69:33–44 (1993).
Hulbert and Bennetzen, "Recombination at the Rp1 locus of maize," *Molec. Gen. Genet.* 226:377–382 (1991).
Kempin et al., "Molecular Basis of the cauliflower Phenotype in Arabidopsis," *Science* 267:522–525 (1995).
Kennard et al., "Genetic analysis of morphological variation in *Brassica oleracea* using molecular markers," *Theor. Appl. Genet.* 87:721–732 (1994).
Kianian and Quiros, "Trait inheritance, fertility and genomic relationships of some n=9 Brassica species," *Genetic Resources and Crop Evolution* 39:165–175 (1992).
King, "Molecular genetics and breeding of vegetable brassicas," *Euphytica* 50:97–112 (1990).

Mandel et al., "Molecular characterization of the Arabidopsis floral homeotic gene Apetala1," *Nature* 360:273–277 (1992).
Slocum et al., "Linkage arrangement of restriction fragment length polymorphism loci in *Brassica oleracea*"*Theor. Appl. Genet.* 80:57–64 (1990).
Weigel, "The Genetics of Flower Development: From Floral Induction to Ovule Morphogenesis," *Annu. Rev. Genetics* 29:19–39 (1995).
Yanofsky, "Floral Meristems to Floral Organs: Genes Controlling Early Events in Arabidopsis Flower Development," *Annu. Rev. Plant Physiol. Plant Mol. Biol.* 46:167–188 (1995).

*Primary Examiner*—Carla J. Myers
*Attorney, Agent, or Firm*—Campbell & Flores LLP

[57] ABSTRACT

The present invention provides a nucleic acid molecule encoding a CAULIFLOWER (CAL) gene product such as a nucleic acid molecule encoding *Arabidopsis thaliana* CAL and a nucleic acid molecule encoding *Brassica oleracea* CAL (BoCAL). The invention also provides a nucleic acid molecule encoding a truncated CAL gene product such as a nucleic acid molecule encoding *Brassica oleracea* var. *botrytis* CAL (BobCAL). The invention also provides a nucleic acid containing the *Arabidopsis thaliana* CAL gene, a nucleic acid molecule containing the *Brassica oleracea* CAL gene and a nucleic acid molecule containing the *Brassica oleracea* var. *botrytis* CAL gene. The invention further provides a kit for converting shoot meristem to floral meristem and a kit for promoting early flowering in an angiosperm. The invention provides a CAL polypeptide and an antibody that specifically binds CAL polypeptide. In addition, the invention provides the truncated BobCAL polypeptide and an antibody that specifically binds truncated BobCAL polypeptide. The invention further provides a method of identifying a Brassica having a modified CAL allele by detecting a polymorphism associated with a CAL locus, where the CAL locus comprises a modified CAL allele that does not encode an active CAL gene product.

5 Claims, 44 Drawing Sheets

```
                                                                         -81
         *         *         *         *         *         *
GAATTCCTCG AGCTACGTCA GGGCCCTGAC GTAGCTCGAA GTCTGAGCTC TTCTTTATAT
                                                                         -21
         *         *         *         *         *         *
CTCTCTTGTA GTTTCTTATT GGGGGTCTTT GTTTTGTTTG GTTCTTTTAG AGTAAGAAGT

*         *         *         *         *         *
TTCTTAAAAA AGGATCAAAA ATG GGA AGG GGT AGG GTT CAA TTG AAG AGG ATA
                        M   G   R   G   R   V   Q   L   K   R   I>       11

40
         *         *         *         *         *         *
GAG AAC AAG ATC AAT AGA CAA GTG ACA TTC TCG AAA AGA AGA GCT GGT
 E   N   K   I   N   R   Q   V   T   F   S   K   R   R   A   G>          27

100
         *         *         *         *         *         *
CTT TTG AAG AAA GCT CAT GAG ATC TCT GTT CTC TGT GAT GCT GAA GTT
 L   L   K   K   A   H   E   I   S   V   L   C   D   A   E   V>          43

160
         *         *         *         *         *         *
GCT CTT GTT GTC TTC TCC CAT AAG GGA AAA CTC TTC GAA TAC TCC ACT
 A   L   V   V   F   S   H   K   G   K   L   F   E   Y   S   T>          59

220
         *         *         *         *         *         *
GAT TCT TGT ATG GAG AAG ATA CTT GAA CGC TAT GAG AGG TAC TCT TAC
 D   S   C   M   E   K   I   L   E   R   Y   E   R   Y   S   Y>          75

*         *         *         *         *         *
GCC GAA AGA CAG CTT ATT GCA CCT GAG TCC GAC GTC AAT ACA AAC TGG
 A   E   R   Q   L   I   A   P   E   S   D   V   N   T   N   W>          91

280
         *         *         *         *         *         *
TCG ATG GAG TAT AAC AGG CTT AAG GCT AAG ATT GAG CTT TTG GAG AGA
 S   M   E   Y   N   R   L   K   A   K   I   E   L   L   E   R>          107

340
         *         *         *         *         *         *
AAC CAG AGG CAT TAT CTT GGG GAA GAC TTG CAA GCA ATG AGC CCT AAA
 N   Q   R   H   Y   L   G   E   D   L   Q   A   M   S   P   K>          123

400
         *         *         *         *         *         *
GAG CTT CAG AAT CTG GAG CAG CAG CTT GAC ACT GCT CTT AAG CAC ATC
 E   L   Q   N   L   E   Q   Q   L   D   T   A   L   K   H   I>          139

460
         *         *         *         *         *         *
CGC ACT AGA AAA AAC CAA CTT ATG TAC GAG TCC ATC AAT GAG CTC CAA
 R   T   R   K   N   Q   L   M   Y   E   S   I   N   E   L   Q>          155

*         *         *         *         *         *
AAA AAG GAG AAG GCC ATA CAG GAG CAA AAC AGC ATG CTT TCT AAA CAG
 K   K   E   K   A   I   Q   E   Q   N   S   M   L   S   K   Q>          171
```

FIG. 1A

```
         520                 *                 *                 *                 *                 *
ATC AAG GAG AGG GAA AAA ATT CTT AGG GCT CAA CAG GAG CAG TGG GAT
 I   K   E   R   E   K   I   L   R   A   Q   Q   E   Q   W   D>                                           187

580                 *                 *                 *
CAG CAG AAC CAA GGC CAC AAT ATG CCT CCC CCT CTG CCA CCG CAG CAG
 Q   Q   N   Q   G   H   N   M   P   P   P   L   P   P   Q   Q>                                           203

*                 *                 *          640                    *
CAC CAA ATC CAG CAT CCT TAC ATG CTC TCT CAT CAG CCA TCT CCT TTT
 H   Q   I   Q   H   P   Y   M   L   S   H   Q   P   S   P   F>                                           219

*                 *                 *                 *      700
CTC AAC ATG GGT GGT CTG TAT CAA GAA GAT GAT CCT ATG GCA ATG AGG
 L   N   M   G   G   L   Y   Q   E   D   D   P   M   A   M   R>                                           235

*                 *                 *                 *                 *
AAT GAT CTC GAA CTG ACT CTT GAA CCC GTT TAC AAC TGC AAC CTT GGC
 N   D   L   E   L   T   L   E   P   V   Y   N   C   N   L   G>                                           251

760                     *                 *                 *                 *
TGC TTC GCC GCA TGA AGC ATT TCC ATA TAT ATA TTT GTA ATC GTC AAC
 C   F   A   A   *   S   I   S   I   Y   I   F   V   I   V   N>                                           267

*          820                *                 *                 *
AAT AAA AAC AGT TTG CCA CAT ACA TAT AAA TAG TGG CTA GGC TCT TTT
 N   K   N   S   L   P   H   T   Y   K   *   W   L   G   S   F>                                           283

*                 *                 *          880        *
CAT CCA ATT AAT ATA TTT TGG CAA ATG TTC GAT GTT CTT ATA TCA TCA
 H   P   I   N   I   F   W   Q   M   F   D   V   L   I   S   S>                                           299

*                 *                 *                 *    940              *
TAT ATA AAT TAG C AGGCTCCTTT CTTCTTTTGT AATTTGATAA GTTTATTTGC
 Y   I   N   *   X>                                                                                       302

1000
         *                 *                 *                 *              *                 *
TTCAATATGG AGCAAAATTG TAATATATTT GAAGGTCAGA GAGAATGAAC GTGAACTTAA

1060
         *                 *                 *                 *              *                 *
TAGAAAAAAA AAAAAAAAAA AAAAAAAAAA AAAAAAAAAA AAACCCGACG TAGCTCGAGG
AATTC
```

FIG. 1B

```
                                                            *                    *
TCTTAGAGGA AATAGTTCCT TTAAAAGGGA TAAAA ATG GGA AGG GGT AGG GTT CAG
                                       M   G   R   G   R   V   Q        7

25
   *                *                *                *                *
TTG AAG AGG ATA GAA AAC AAG ATC AAT AGA CAA GTG ACA TTC TCG AAA
 L   K   R   I   E   N   K   I   N   R   Q   V   T   F   S   K          23

85
        *                *                *                *                *
AGA AGA GCT GGT CTT ATG AAG AAA GCT CAT GAG ATC TCT GTT CTG TGT
 R   R   A   G   L   M   K   K   A   H   E   I   S   V   L   C          39

145
        *                *                *                *                *
GAT GCT GAA GTT GCG CTT GTT GTC TTC TCC CAT AAG GGG AAA CTC TTT
 D   A   E   V   A   L   V   V   F   S   H   K   G   K   L   F          55

205
        *                *                *                *                *
GAA TAC TCC ACT GAT TCT TGT ATG GAG AAG ATA CTT GAA CGC TAT GAG
 E   Y   S   T   D   S   C   M   E   K   I   L   E   R   Y   E          71

*                *                *                *                *
AGA TAC TCT TAC GCC GAG AGA CAG CTT ATA GCA CCT GAG TCC GAC TCC
 R   Y   S   Y   A   E   R   Q   L   I   A   P   E   S   D   S          87

265
  *                *                *                *                *
AAT ACG AAC TGG TCG ATG GAG TAT AAT AGG CTT AAG GCT AAG ATT GAG
 N   T   N   W   S   M   E   Y   N   R   L   K   A   K   I   E          103

325
                  *                *                *                *
CTT TTG GAG AGA AAC CAG AGG CAC TAT CTT GGG GAA GAC TTG CAA GCA
 L   L   E   R   N   Q   R   H   Y   L   G   E   D   L   Q   A          119

385
        *                *                *                *                *
ATG AGC CCT AAG GAA CTC CAG AAT CTA GAG CAA CAG CTT GAT ACT GCT
 M   S   P   K   E   L   Q   N   L   E   Q   Q   L   D   T   A          135

445
        *                *                *                *                *
CTT AAG CAC ATC CGC TCT AGA AAA AAC CAA CTT AGT TAC GAC TCC ATC
 L   K   H   I   R   S   R   K   N   Q   L   S   Y   D   S   I          151

*                *                *                *                *
AAT GAG CTC CAA AGA AAG GAG AAA GCC ATA CAG GAA CAA AAC AGC ATG
 N   E   L   Q   R   K   E   K   A   I   Q   E   Q   N   S   M          167

505
  *                *                *                *                *
CTT TCC AAG CAG ATT AAG GAG AGG GAA AAC GTT CTT AGG GCG CAA CAA
 L   S   K   Q   I   K   E   R   E   N   V   L   R   A   Q   Q          183
```

FIG. 2A

```
                       565                  *                  *                  *
GAG CAA TGG GAC GAG CAG AAC CAT GGC CAT AAT ATG CCT CCG CCT CCA
 E   Q   W   D   E   Q   N   H   G   H   N   M   P   P   P   P     199

*                   *         625           *                   *
CCC CCG CAG CAG CAT CAA ATC CAG CAT CCT TAC ATG CTC TCT CAT CAG
 P   P   Q   Q   H   Q   I   Q   H   P   Y   M   L   S   H   Q     215

*                   *                   *   685
CCA TCT CCT TTT CTC AAC ATG GGG GGG CTG TAT CAA GAA GAA GAT CAA
 P   S   P   F   L   N   M   G   G   L   Y   Q   E   E   D   Q     231

*                   *                   *                   *
ATG GCA ATG AGG AGG AAC GAT CTC GAT CTG TCT CTT GAA CCC GGT TAT
 M   A   M   R   R   N   D   L   D   L   S   L   E   P   G   Y     247

745              *
AAC TGC AAT CTC GGC TGC
 N   C   N   L   G   C                                             253
```

FIG. 2B

```
ATG GGA AGG GGT AGG GTT CAG TTG AAG AGG ATA GAA AAC AAG ATC AAT        16
 M   G   R   G   R   V   Q   L   K   R   I   E   N   K   I   N

60
AGA CAA GTG ACA TTC TCG AAA AGA AGA GCT GGT CTT ATG AAG AAA GCT        32
 R   Q   V   T   F   S   K   R   R   A   G   L   M   K   K   A

120
CAT GAG ATC TCT GTT CTG TGT GAT GCT GAA GTT GCG CTT GTT GTC TTC        48
 H   E   I   S   V   L   C   D   A   E   V   A   L   V   V   F
                                              180
TCC CAT AAG GGG AAA CTC TTT GAA TAC CCC ACT GAT TCT TGT ATG GAG        64
 S   H   K   G   K   L   F   E   Y   P   T   D   S   C   M   E
                                                              240
GAG ATA CTT GAA CGC TAT GAG AGA TAC TCT TAC GCC GAG AGA CAG CTT        80
 E   I   L   E   R   Y   E   R   Y   S   Y   A   E   R   Q   L

ATA GCA CCT GAG TCC GAC TCC AAT ACG AAC TGG TCG ATG GAG TAT AAT        96
 I   A   P   E   S   D   S   N   T   N   W   S   M   E   Y   N
          300
AGG CTT AAG GCT AAG ATT GAG CTT TTG GAG AGA AAC CAG AGG CAC TAT       112
 R   L   K   A   K   I   E   L   L   E   R   N   Q   R   H   Y
                      360
CTT GGG GAA GAC TTG CAA GCA ATG AGC CCT AAG GAA CTC CAG AAT CTA       128
 L   G   E   D   L   Q   A   M   S   P   K   E   L   Q   N   L
                                      420
GAG CAA CAG CTT GAT ACT GCT CTT AAG CAC ATC CGC TCT AGA AAA AAC       144
 E   Q   Q   L   D   T   A   L   K   H   I   R   S   R   K   N
                                                      480
CAA CTT ATG TAC GAC TCC ATC AAT GAG CTC CAA AGA AAG GAG AAA GCC       160
 Q   L   M   Y   D   S   I   N   E   L   Q   R   K   E   K   A

ATA CAG GAA CAA AAC AGC ATG CTT TCC AAG CAG ATT AAG GAG AGG GAA       176
 I   Q   E   Q   N   S   M   L   S   K   Q   I   K   E   R   E
          540
AAC GTT CTT AGG GCG CAA CAA GAG CAA TGG GAC GAG CAG AAC CAT GGC       192
 N   V   L   R   A   Q   Q   E   Q   W   D   E   Q   N   H   G
```

FIG. 3A

```
                                600
CAT AAT ATG CCT CCG CCT CCA CCC CCG CAG CAG CAT CAA ATC CAG CAT
 H   N   M   P   P   P   P   P   P   Q   Q   H   Q   I   Q   H     208
                                              660
CCT TAC ATG CTC TCT CAT CAG CCA TCT CCT TTT CTC AAC ATG GGA GGG
 P   Y   M   L   S   H   Q   P   S   P   F   L   N   M   G   G     224
                                                          720
CTG TAT CAA GAA GAA GAT CAA ATG GCA ATG AGG AGG AAC GAT CTC GAT
 L   Y   Q   E   E   D   Q   M   A   M   R   R   N   D   L   D     240
CTG TCT CTT GAA CCC GTT TAC AAC TGC AAC CTT GGC CGT CGC TGC TGA
 L   S   L   E   P   V   Y   N   C   N   L   G   R   R   C   *     255
```

FIG. 3B

```
                    GCACGAGTCCTCCTCCTCTGGCATCCCACCCCACCTTCTCCTTAAAGCTACCTGCCTACCCGG    60
CGGTTGCGCGGCCGCAATCGATCGACCGGAAGAGAAGCAGCTAGCTAGCAGATCGGAGCACGGCAACAAGGCG    20

ATG GGG CGC GGC AAG GTA CAG CTG AAG GTA AAC CGG CAG GTG ACC                 120
 M   G   R   G   K   V   Q   L   K   I   N   R   Q   V   T                   40

TTC TCC AAG CGC CGG AAC GGC CTG CTC AAG ATA GAG AAC CAC GTC CTC GAT         180
 F   S   K   R   R   N   G   L   L   K   I   E   N   H   V   L   D           60

GCC GAG GTC GCC GTC ATC GTC TTC TCC CCC AAG GGC ATC TCC TAC ATC TGC GAC     240
 A   E   V   A   V   I   V   F   S   P   K   G   I   S   Y   I   C   D       80

TCC CGC ATG GAC AAA ATT CTT GAA CGC TAT GAG TAT TCC TAC GAA GCT CTT         300
 S   R   M   D   K   I   L   E   R   Y   E   Y   S   Y   E   A   L          100

ATT TCA GCT GAA TCT AAA CAA ATA TGG TGC CAC GAG GGA AGG TAC AGG GCC         360
 I   S   A   E   S   K   Q   I   W   C   H   E   G   R   Y   R   A          120

AAA ATT GAG AAA ACC CAA CAA AAG AGT GAG GAG ATG GGA GAT AGC TCA GAG TCT TTG 420
 K   I   E   K   T   Q   Q   K   S   E   E   M   G   D   S   S   E   S   L  140

AAT CCC AAA GAG CTC CTC CAG CAG CAG CAG CAC CTG ATT TCT ATT CAG AGG CAC ATC AGA 480
 N   P   K   E   L   L   Q   Q   Q   Q   H   L   I   S   I   Q   R   H   I   R  160

TCA AGG AAG AGC AGC CAT CTT ATG GCT CTA GAG GAT TCT GCG GAA CTT AAG GAG AGG TCA 540
 S   R   K   S   S   H   L   M   A   L   E   D   S   A   E   L   K   E   R   S  180

CTG CAG GAG CAG CAG CAG CTG CAG GCT GTC CAG CTA GAG CAG CAG CAA CAT CAT GCC CAG A 600
 L   Q   E   Q   Q   Q   L   Q   A   V   Q   L   E   Q   Q   Q   H   H   A   Q    200

AGC CAG CAG CAG CAG CAG CAC CAC CAC CAG CAG CAG TGG GAC AAG AAG CAG ACA CAG CTG CCG A 660
 S   Q   Q   Q   Q   Q   H   H   H   Q   Q   Q   W   D   K   K   Q   T   Q   L   P    220

CAG ACA AGC TCA TCA TCG TCC TCC TCC TTC ATG ATG AGG CAG GAT CAG GGA CCT
 Q   T   S   S   S   S   S   S   F   M   M   R   Q   D   Q   G   P
```

FIG. 4A

```
CCA CAC AAC ATC TGC TTC CCG CCG TTG ACA ATG GGA GAT AGA GGT GAA GAG CTG GCT GCG    720
 P   H   N   I   C   F   P   P   L   T   M   G   D   R   G   E   E   L   A   A    240

GCG GCG GCG CAG CAG CAG CAG CCA CTG CCG GGG CAG GCG CAA CCG CAG CTC CGC ATC        780
 A   A   A   Q   Q   Q   Q   P   L   P   G   Q   A   Q   P   Q   L   R   I        260

GCA GGT CTG CCA CCA TGG ATG CTG AGC CAC CTC AAT GCA TAA  GGAGAGGGTCGATGAACACATCG   845
 A   G   L   P   P   W   M   L   S   H   L   N   A   *                             273

ACCTCCTCTCTCTCTCGTCATGGATCATGACGTACGCGTACCATGGTTGCTGTGCCTGCCCCCATCGATCG            924
CGAGCAATGGCACGCTCAAGTGATCATTGCTCCCCGTTGGTTAAACCCTAGCCTATGTTCATGGCGTCAGCAACT       1003
AAGCTAAACTATTGTTTGCAAGAAAGGGTAAACCCGCTAGCTGTGTAATCTGTCCAGCTGTCTTGTCAGTATGCTTGT    1082
TACTGCCCAGTTACCCTTGAATCTTAGCGCGGCGCTTTGGTGAGAGGGTGCAGTTGCAGTTTACTTTAAACATGGTTCGTGACTTGC  1161
TGTAAATAGTAGTATTAATCGATTTGGGCATCT(A)n                                            1195
```

FIG. 4B

```
           *               *              *                *              *
TTAAGAGAA ATG GGA AGG GGT AGG GTT GAA TTG AAG AGG ATA GAG AAC AAG
          M   G   R   G   R   V   E   L   K   R   I   E   N   K>      14

51
         *              *               *              *
ATC AAT AGA CAA GTG ACA TTC TCG AAA AGA AGA ACT GGT CTT TTG AAG
 I   N   R   Q   V   T   F   S   K   R   R   T   G   L   L   K>      30

111
 *              *        *              *              *
AAA GCT CAG GAG ATC TCT GTT CTT TGT GAT GCC GAG GTT TCC CTT ATT
 K   A   Q   E   I   S   V   L   C   D   A   E   V   S   L   I>      46

171
 *              *              *         *              *
GTC TTC TCC CAT AAG GGC AAA TTG TTC GAG TAC TCC TCT GAA TCT TGC
 V   F   S   H   K   G   K   L   F   E   Y   S   S   E   S   C>      62

231
 *              *              *              *         *
ATG GAG AAG GTA CTA GAA CGC TAC GAG AGG TAT TCT TAC GCC GAG AGA
 M   E   K   V   L   E   R   Y   E   R   Y   S   Y   A   E   R>      78

*              *              *              *              *
CAG CTG ATT GCA CCT GAC TCT CAC GTT AAT GCA CAG ACG AAC TGG TCA
 Q   L   I   A   P   D   S   H   V   N   A   Q   T   N   W   S>      94

291
         *              *              *              *
ATG GAG TAT AGC AGG CTT AAG GCC AAG ATT GAG CTT TTG GAG AGA AAC
 M   E   Y   S   R   L   K   A   K   I   E   L   L   E   R   N>     110

351
 *              *        *              *              *
CAA AGG CAT TAT CTG GGA GAA GAG TTG GAA CCA ATG AGC CTC AAG GAT
 Q   R   H   Y   L   G   E   E   L   E   P   M   S   L   K   D>     136

411
 *              *              *         *              *
CTC CAA AAT CTG GAG CAG CAG CTT GAG ACT GCT CTT AAG CAC ATT CGC
 L   Q   N   L   E   Q   Q   L   E   T   A   L   K   H   I   R>     152

471
 *              *              *              *         *
TCC AGA AAA AAT CAA CTC ATG AAT GAG TCC CTC AAC CAC CTC CAA AGA
 S   R   K   N   Q   L   M   N   E   S   L   N   H   L   Q   R>     168

*              *              *              *              *
AAG GAG AAG GAG ATA CAG GAG GAA AAC AGC ATG CTT ACC AAA CAG ATA
 K   E   K   E   I   Q   E   E   N   S   M   L   T   K   Q   I>     184

531
         *              *              *              *
AAG GAG AGG GAA AAC ATC CTA AAG ACA AAA CAA ACC CAA TGT GAG CAG
 K   E   R   E   N   I   L   K   T   K   Q   T   Q   C   E   Q>     200

591
 *              *              *              *              *
CTG AAC CGC AGC GTC GAC GAT GTA CCA CAG CCA CAA CCA TTT CAA CAC
```

FIG. 5A

```
                L    N    R    S    V    D    D    V    P    Q    P    Q    P    F    Q    H>   216
                                                            651
     *                        *                        *                        *
    CCC  CAT  CTT  TAC  ATG  ATC  GCT  CAT  CAG  ACT  TCT  CCT  TTC  CTA  AAT  ATG
     P    H    L    Y    M    I    A    H    Q    T    S    P    F    L    N    M>   232
                                                                           711
          *                   *                   *                   *         *
    GGT  GGT  TTG  TAC  CAA  GGA  GAA  GAC  CAA  ACG  GCG  ATG  AGG  AGG  AAC  AAT
     G    G    L    Y    Q    G    E    D    Q    T    A    M    R    R    N    N>   248
               *              *              *              *              *
    CTG  GAT  CTG  ACT  CTT  GAA  CCC  ATT  TAC  AAT  TAC  CTT  GGC  TGT  TAC  GCC
     L    D    L    T    L    E    P    I    Y    N    Y    L    G    C    Y    A>   262
    GCT  TGA  --
     A    *    X>                                                                    263
```

FIG. 5B

```
ATG GGA AGG GGT AGG GTT GAA ATG AAG AGG ATA GAG AAC AAG ATC AAC
 M   G   R   G   R   V   E   M   K   R   I   E   N   K   I   N     16
          60
CGA CAA GTG ACG TTT TCG AAA AGA AGA GCT GGT CTT TTG AAG AAA GCC
 R   Q   V   T   F   S   K   R   R   A   G   L   L   K   K   A     32
                     120
CAT GAG ATC TCG ATC CTT TGT GAT GCT GAG GTT TCC CTT ATT GTC TTC
 H   E   I   S   I   L   C   D   A   E   V   S   L   I   V   F     48
                                     180
TCC CAT AAG GGG AAA CTG TTC GAG TAC TCG TCT GAA TCT TGC ATG GAG
 S   H   K   G   K   L   F   E   Y   S   S   E   S   C   M   E     64
                                                         240
AAG GTA CTA GAA CAC TAC GAG AGG TAC TCT TAC GCC GAG AAA CAG CTA
 K   V   L   E   H   Y   E   R   Y   S   Y   A   E   K   Q   L     80
AAA GTT CCA GAC TCT CAC GTC AAT GCA CAA ACG AAC TGG TCA GTG GAA
 K   V   P   D   S   H   V   N   A   Q   T   N   W   S   V   E     96
          300
TAT AGC AGG CTT AAG GCT AAG ATT GAG CTT TTG GAG AGA AAC CAA AGG
 Y   S   R   L   K   A   K   I   E   L   L   E   R   N   Q   R    112
                     360
CAT TAT CTG GGC GAA GAT TTA GAA TCA ATC AGC ATA AAG GAG CTA CAG
 H   Y   L   G   E   D   L   E   S   I   S   I   K   E   L   Q    128
                                         420
AAT CTG GAG CAG CAG CTT GAC ACT TCT CTT AAA CAT ATT CGC TCG AGA
 N   L   E   Q   Q   L   D   T   S   L   K   H   I   R   S   R    144
                                                     480
AAA AAT CAA CTA ATG CAC GAG TCC CTC AAC CAC CTC CAA AGA AAG GAG
 K   N   Q   L   M   H   E   S   L   N   H   L   Q   R   K   E    160
AAA GAA ATA CTG GAG GAA AAC AGC ATG CTT GCC AAA CAG ATA AGG GAG
 K   E   I   L   E   E   N   S   M   L   A   K   Q   I   R   E    176
          540
AGG GAG AGT ATC CTA AGG ACA CAT CAA AAC CAA TCA GAG CAG CAA AAC
 R   E   S   I   L   R   T   H   Q   N   Q   S   E   Q   Q   N    192
```

FIG. 6A

```
                                600
      *          *               *                  *                *
CGC AGC CAC CAT GTA GCT CCT CAG CCG CAA CCG CAG TTA AAT CCT TAC
 R   S   H   H   V   A   P   Q   P   Q   P   Q   L   N   P   Y       208

*               *              *       660
                                              *                     *
ATG GCA TCA TCT CCT TTC CTA AAT ATG GGT GGC ATG TAC CAA GGA GAA
 M   A   S   S   P   F   L   N   M   G   G   M   Y   Q   G   E       224

720
      *               *              *              *         *
TAT CCA ACG GCG GTG AGG AGG AAC CGT CTC GAT CTG ACT CTT GAA CCC
 Y   P   T   A   V   R   R   N   R   L   D   L   T   L   E   P       240

*              *              *
ATT TAC AAC TGC AAC CTT GGT TAC TTT GCC GCA TGA
 I   Y   N   C   N   L   G   Y   F   A   A   *                        251
```

FIG. 6B

```
ATG GGA AGG GGT AGG GTT GAA ATG AAG AGG ATA GAG AAC AAG ATC AAC
 M   G   R   G   R   V   E   M   K   R   I   E   N   K   I   N     16

60
AGA CAA GTG ACG TTT TCG AAA AGA AGA GCT GGT CTT TTG AAG AAA GCC
 R   Q   V   T   F   S   K   R   R   A   G   L   L   K   K   A     32

120
CAT GAG ATC TCG ATT CTT TGT GAT GCT GAG GTT TCC CTT ATT GTC TTC
 H   E   I   S   I   L   C   D   A   E   V   S   L   I   V   F     48

180
TCC CAT AAG GGG AAA CTG TTC GAG TAC TCG TCT GAA TCT TGC ATG GAG
 S   H   K   G   K   L   F   E   Y   S   S   E   S   C   M   E     64

240
AAG GTA CTA GAA CGC TAC GAG AGG TAC TCT TAC GCC GAG AAA CAG CTA
 K   V   L   E   R   Y   E   R   Y   S   Y   A   E   K   Q   L     80

AAA GCT CCA GAC TCT CAC GTC AAT GCA CAA ACG AAC TGG TCA ATG GAA
 K   A   P   D   S   H   V   N   A   Q   T   N   W   S   M   E     96

300
TAT AGC AGG CTT AAG GCT AAG ATT GAG CTT TGG GAG AGG AAC CAA AGG
 Y   S   R   L   K   A   K   I   E   L   W   E   R   N   Q   R    112

360
CAT TAT CTG GGA GAA GAT TTA GAA TCA ATC AGC ATA AAG GAG CTA CAG
 H   Y   L   G   E   D   L   E   S   I   S   I   K   E   L   Q    128

420
AAT CTG GAG CAG CAG CTT GAC ACT TCT CTT AAA CAT ATT CGC TCC AGA
 N   L   E   Q   Q   L   D   T   S   L   K   H   I   R   S   R    144

480
AAA AAT CAA CTA ATG CAC TAG T CCCTCA ACCACCTCCA AAGAAAGGAG
 K   N   Q   L   M   H   *  X                                     150

540
AAAGAAATAC TGGAGGAAAA CAGCATGCTT GCCAAACAGA TAAAGGAGAG GGAGAGTATC

600
CTAAGGACAC ATCAAAACCA ATCAGAGCAG CAAAACCGCA GCCACCATGT AGCTCCTCAG

660
CCGCAACCGC AGTTAAATCC TTACATGGCA TCATCTCCTT TCCTAAATAT GGGTGGCATG

720
TACCAAGGAG AATATCCAAC GGCGGTGAGG AGGAACCGTC TCGATCTGAC TCTTGAACCC

ATTTACAACT GCAACCTTGG TTACTTTGCC GCATGA
```

FIG. 7

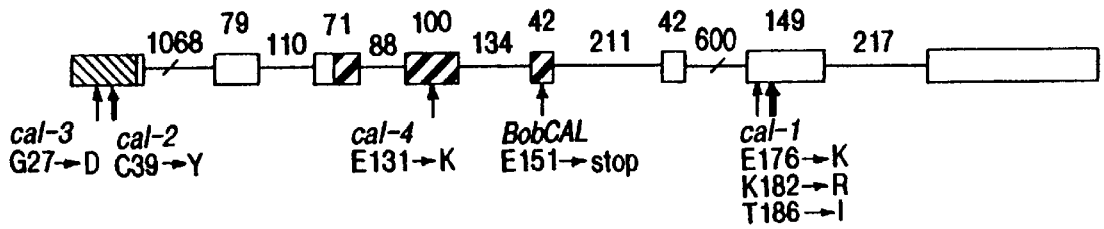

FIG. 8A

```
CAL     MGRGRVLLKRIKNKINRQVTFSKRRTGLLKKAQKISVLCDAKVSLIVFSK    50
BoCAL        M                  A      H   I
BobCAL       M                  A      H   I
AP1          Q                  A      H
                                                     A V

CAL     KGKLFEYSSESCMEKVLERYERYSYAERQLIAPDSHVNAQTNWSMEYSRL    100
BoCAL                H         K KV
BobCAL                         K K
AP1          TD     I              E D   --        N

CAL     KAKIELLERNQRHYLGEELEPMSLKDLQNLEQQLETALKHIRSRKNQLMY   150
BoCAL                 D SI I E         D S             H
BobCAL         W      D SI I E         D               H
AP1                   D QA  P E        D         T     Y

CAL     ESLNHLQRKEKEIQEENSMLTKQIKERENILKTKQTQCEQLNRSVDDVPQ   200
BoCAL           L      V A    R    S   R H N S  Q   HHVA
BobCAL    *
AP1        I E K   A    Q     S      K  RAQ E WD Q  QGHNMP -

CAL     PQPFQHPHL---YMIAHQTSPFLNMGGLYQGEDQTAMRRNNLDLTLEPIY   247
BoCAL       QLN YM  -----AS         M      YP   V    R
BobCAL
AP1       L P QHQIQHP  LS  P            ED PM    D E     V

CAL     NY-LGCYAA*                                           255
BoCAL     CN YF
BobCAL
AP1       CN  F
```

FIG. 8B

```
AAAGCAATCTGCTCAAAGAGTAAAGAAGAGTAGAAAAAGAGAGAAAAATAGATTGATAGAGAGAGAAAAATAGATTATGATCCTGAAGGTTCACGAGTGGCTT    100
                                                                           M  D  P  E  G  F  T  S  G  L      10

ATTCCGGTGAACCCAACGAGAGCATTGGTTCAAGCACCTCCGTTCCACTTCCGCTGCAGCAACAGCCGGTGACACCGCAGCAACGGCTGCTTTTGGG          200
 F  R  W  N  P  T  R  A  L  V  Q  A  P  P  P  V  P  P  P  L  Q  Q  P  V  T  P  Q  T  A  A  F  G            43

ATGCGACTTGGGTGGTTTAGAGGACTATTCGGTCCATACGGTTTCTCACACGGTTATATACGTTTCTCCATATCTTCGTATACGGAGTTAGTTTACGGCAGCACGCTTG    300
 M  R  L  G  G  L  E  G  L  F  G  P  Y  G  I  R  F  Y  T  A  A  K  I  A  E  L  G  F  T  A  S  T  L  V     77

TGGGTATGAAGGACGAGGAGCTTGAAGAGATGATGAATAGTCTCTCATATCTTCGTTGGTGAGCTTCTGTTGGTGAACGGTACGGTATCAAAGCTGC            400
 G  M  K  D  E  E  L  E  E  M  M  N  S  L  S  H  I  F  R  W  E  L  L  V  G  E  R  Y  G  I  K  A  A        110

CGTTAGAGCTGAACGGAGACGATTGCAAGAGAAGAGGAAGAATCTTCTAGACGCCGTCATTTGCTACTCTCCGCCGTCGTGATTCCGGTACTCAT             500
 V  R  A  E  R  R  R  L  Q  E  E  E  E  E  E  E  S  R  R  R  H  L  L  S  A  A  G  D  S  G  T  H         143

CACGCTCTGATGCTCTCCCAAGAAGATGATTGGACAGGGTTATCTGAGGAACAGGTGCAGCAACAAGACCAGACTGATGCGGGGAATAACGGCG             600
 H  A  L  D  A  L  S  Q  E  D  D  W  T  G  L  S  E  E  P  V  Q  Q  Q  D  T  D  A  A  G  N  N  G  G    177

GAGGAGGAAGTGGTTACTGGGACGCAGTCAAGGAAAGATGAAGAAGCAGCAGAACGAGAAAGAAACCAATGCTGACGTCAGTGAAACCGA                 700
 G  G  S  G  Y  W  D  A  G  Q  G  K  M  K  K  Q  Q  Q  R  R  K  K  P  M  L  T  S  V  E  T  D        210

CGAAGACGTCAACGAAGGTGAGGATGACGACGGATGATAACGGCAACGGAGTAGTGGTTTGGGACAGAGGAGCATCCGTTTATCGTA                    800
 E  D  V  N  E  G  E  D  D  D  G  M  D  N  G  N  G  G  S  G  L  G  T  E  R  Q  R  E  H  P  F  I  V   243
```

FIG. 9A

```
ACGGAGCCTGGGGAAGTGGCACGTGGCAAAAAGAACGGCTTAGATTATCTGTTCCACTTGTTACGAACAATGCCGTGAGTTCCTTCTTCAGGTCCAGACAA    900
 T  E  P  G  E  V  A  R  G  K  K  N  G  L  D  Y  L  F  H  L  Y  E  Q  C  R  E  F  L  L  Q  V  Q  T  I    ..277

TTGCTAAAGACCTGGCGCGGAAAAATGCCCCACCAAGGTGACGAACCAAGTATTCAGTGCGAAGAAATCAGGAGCGAGTTACATAAACAAGCCTAAAAT    1000
 A  K  D  R  G  E  K  C  P  T  K  V  T  N  Q  V  F  R  Y  A  K  K  S  G  A  S  Y  I  N  K  P  K  M     310

GCGACACTACGTTCACTGTACGCTCTCCACTGCCTAGACGAAGAAGCTTCAAATGCTCTCAGAAGAGCGTTAAAGAACGCGGTGAGAACGTTGGCTCA    1100
 R  H  Y  V  H  C  Y  A  L  H  C  L  D  E  E  A  S  N  A  L  R  R  A  F  K  E  R  G  E  N  V  G  S     343

TGGCGTCAGGCTGTGTTACAAGCCACTTGTGAACATCGCTGTCGTCTGGAATATAGACGCCGTCTTAACGCTCATCCTGTCTCTATTGGT    1200
 W  R  Q  A  C  Y  K  P  L  V  N  I  A  C  R  H  G  W  D  I  D  A  V  F  N  A  H  P  R  L  S  I  W  Y  377

ATGTTCCAACAAAGCTGCGTCAGCTTTGCCATTTGGAGCGGAACAATGCGGTTGCTGCGGCTTAGTTGGCGGTATTAGCTGTACCGATCGTC    1300
 V  P  T  K  L  R  Q  L  C  H  L  E  R  N  N  A  V  A  A  A  A  L  V  G  G  I  S  C  T  G  S  S     410

GACGTCTGACGTGGTGGATGCGGCGGCGACGACTGCGTTCTAGTTGGTTTCTTAGTTGTGTTTAGTGTTGTTTAGTGTTATCCTAATTAACTATTAGTC  1400
 T  S  G  R  G  G  C  G  G  D  D  D  L  R  F stop                                                      424

TTTAATTAGTCTCTTGGCTAATATTTATTTCTTTTTGTCAAACCTTAATTGTTATGGCTAATTGTTATACACGCAGTTTCTTAATGCGTTA           1500
```

FIG. 9B

```
         *          *          *          *          *
    GAATTCCCCG GATCTCCATA TACATATCAT ACATATATAT AGTATACTAT
         60
         *          *          *          *          *
    CTTTAGACTG ATTTCTCTAT ACACTATCTT TTAACTTATG TATCGTTTCA
                    120
         *          *          *          *          *
    AAACTCAGGA CGTACATGTT TTAAATTTGG TTATATAACC ACGACCATTT
                              180
         *          *          *          *          *
    CAAGTATATA TGTCATACCA TACCAGATTT AATATAACTT CTATGAAGAA
                                        240
         *          *          *          *          *
    AATACATAAA GTTGGATTAA AATGCAAGTG ACATCTTTTT AGCATAGGTT
                                                  300
         *          *          *          *          *
    CATTTGGCAT AGAAGAAATA TATAACTAAA AATGAACTTT AACTTAAATA

*          *          *          *          *
    GATTTTACTA TATTACAATT TTTCTTTTTA CATGGTCTAA TTTATTTTTC
         360
         *          *          *          *          *
    TAAAATTAGT ATGATTGTTG TTTTGATGAA ACAATAATAC CGTAAGCAAT
                    420
         *          *          *          *          *
    AGTTGCTAAA AGATGTCCAA ATATTTATAA ATTACAAAGT AAATCAAATA
                              480
         *          *          *          *          *
    AGGAAGAAGA CACGTGGAAA ACACCAAATA AGAGAAGAAA TGGAAAAAAC
                                        540
         *          *          *          *          *
    AGAAAGAAAT TTTTTAACAA GAAAAATCAA TTAGTCCTCA AACCTGAGAT
                                                  600
         *          *          *          *          *
    ATTTAAAGTA ATCAACTAAA ACAGGAACAC TTGACTAACA AAGAAATTTG

*          *          *          *          *
    AAATGTGGTC CAACTTTCAC TTAATTATAT TATTTTCTCT AAGGCTTATG
         660
         *          *          *          *          *
    CAATATATGC CTTAAGCAAA TGCCGAATCT GTTTTTTTTT TTTGTTATTG
                    720
         *          *          *          *          *
    GATATTGACT GAAAATAAGG GGTTTTTTCA CACTTGAAGA TCTCAAAAGA
                              780
         *          *          *          *          *
    GAAAACTATT ACAACGGAAA TTCATTGTAA AAGAAGTGAT TAAGCAAATT
                                        840
         *          *          *          *          *
```

FIG. 10A

```
GAGCAAAGGT TTTTATGTGG TTTATTTCAT TATATGATTG ACATCAAATT
                                                    900
     *          *          *          *          *
GTATATATAT GGTTGTTTTA TTTAACAATA TATATGGATA TAACGTACAA
     *          *          *          *          *
ACTAAATATG TTTGATTGAC GAAAAAAAAT ATATGTATGT TTGATTAACA
    960
     *          *          *          *          *
ACATAGCACA TATCAACTGA TTTTTGTCCT GATCATCTAC AACTTAATAA
              1020
     *          *          *          *          *
GAACACACAA CATTGAAAAA ATCTTTGACA AAATACTATT TTTGGGTTTG
                        1080
     *          *          *          *          *
AAATTTTGAA TACTTACAAT TATCTTCTCG ATCTTCCTCT CTTTCCTTAA
                                   1140
     *          *          *          *          *
ATCCTGCGTA CAAATCCGTC GACGCAATAC ATTACACAGT TGTCAATTGG
                                                    1200
     *          *          *          *          *
TTCTCAGCTC TACCAAAAAC ATCTATTGCC AAAAGAAAGG TCTATTTGTA
     *          *          *          *          *
CTTCACTGTT ACAGCTGAGA ACATTAAATA TAATAAGCAA ATTTGATAAA
    1260
     *          *          *          *          *
ACAAAGGGTT CTCACCTTAT TCCAAAAGAA TAGTGTAAAA TAGGGTAATA
              1320
     *          *          *          *          *
GAGAAATGTT AATAAAAGGA AATTAAAAAT AGATATTTTG GTTGGGTTCA
                        1380
     *          *          *          *          *
GATTTTGTTT CGTAGATCTA CAGGGAAATC TCCGCCGTCA ATGCAAAGCG
                                   1440
     *          *          *          *          *
AAGGTGACAC TTGGGGAAGG ACCAGTGGTC GTACAATGTT ACTTACCCAT
                                                    1500
     *          *          *          *          *
TTCTCTTCAC GAGACGTCGA TAATCAAATT GTTTATTTTC ATATTTTTAA
     *          *          *          *          *
GTCCGCAGTT TTATTAAAAA ATCATGGACC CGACATTAGT ACGAGATATA
    1560
     *          *          *          *          *
CCAATGAGAA GTCGACACGC AAATCCTAAA GAAACCACTG TGGTTTTTGC
              1620
     *          *          *          *          *
AAACAAGAGA AACCAGCTTT AGCTTTTCCC TAAAACCACT CTTACCCAAA
```

FIG. 10B

```
                        1680
      *         *         *         *         *
TCTCTCCATA AATAAAGATC CCGAGACTCA AACACAAGTC TTTTTATAAA
                                  1740
      *         *         *         *         *
GGAAAGAAAG AAAAACTTTC CTAATTGGTT CATACCAAAG TCTGAGCTCT
                                                 1800
      *         *         *         *         *
TCTTTATATC TCTCTTGTAG TTTCTTATTG GGGGTCTTTG TTTTGTTTGG
      *         *         *         *         *
TTCTTTTAGA GTAAGAAGTT TCTTAAAAAA GGATCAAAAA TGGGAAGGGG
         1860
      *         *         *         *         *
TAGGGTTCAA TTGAAGAGGA TAGAGAACAA GATCAATAGA CAAGTGACAT
                1920
      *         *         *         *         *
TCTCGAAAAG AAGAGCTGGT CTTTTGAAGA AAGCTCATGA GATCTCTGTT
                        1980
      *         *         *         *         *
CTCTGTGATG CTGAAGTTGC TCTTGTTGTC TTCTCCCATA AGGGGAAACT
                                        2040
      *         *         *         *         *
CTTCGAATAC TCCACTGATT CTTGGTAACT TCAACTAATT CTTTACTTTT
                                                 2100
      *         *         *         *         *
AAAAAAATCT TTTAATCTGC TACTTTATAT AGTTTTTTTC CCCC----GG
      *         *         *         *         *
TCTATGATTC ATACTGTTTT GTTATTATAA AGGTATCATA GAGATCGGTA
         2160
      *         *         *         *         *
CTTGATTTGT TATAGGAAAT CTTGGTTTAA TTGCATAAAA CCATCATTAG
                2220
      *         *         *         *         *
ATTTATCCTA AAATGTGATG ATATTTTGGT CACATCTCCA TATTATTTAT
                        2280
      *         *         *         *         *
ATAATAAAAT GATAATTGGT TGATGATAAA GCTAACCCTA ATTCTGTGAA
                                        2340
      *         *         *         *         *
ATGATCAGTA TGGAGAAGAT ACTTGAACGC TATGAGAGGT ACTCTTACGC
                                                 2400
      *         *         *         *         *
CGAAAGACAG CTTATTGCAC CTGAGTCCGA CGTCAATGTA TTTCAATAAA
      *         *         *         *         *
TATTTCTCCT TTTAATCCAC ATATATATTA TATCAATCTA TTTGTAGTAT
         2460
      *         *         *         *         *
```

FIG. 10C

```
TGATGAATTT TATTTGTATA AAACTTCTGG TACACAGACA AACTGGTCGA
                    2520
        *           *          *          *          *
TGGCGTATAA CAGGCTTAAG GCTAAGATTG AGCTTTTGGA GAGAAACCAG
                               2580
        *           *          *          *          *
AGGTACACAT TTACACTCAT CACATTTCTA TCTAGAAAAT CGATCGGGTT
                                          2640
        *           *          *          *          *
CCATTTTAAA GTAAGTTAAA ATTCATTGAT GCTATTGAAA TTCAGGCATT
                                                    2700
        *           *          *          *          *
ATCTTGGGGA AGACTTGCAA GCAATGAGCC CTAAAGAGCT TCAGAATCTG

*           *          *          *          *
GAGCAGCAGC TTGACACTGC TCTTAAGCAC ATCCGCACTA GAAAAGTATT
         2760
        *           *          *          *          *
GCCTTCTGCT ATTTCGTTGA ACATATCTAT ATAACTTAAA CGTTTACAAG
                    2820
        *           *          *          *          *
TGTTATTATA ATGTGAACAT TGAAATACAT ATGTGTATGT ATCAATATAT
                               2880
        *           *          *          *          *
ATATCAGTAA TCAATATCAA TTTGATATGT CTATAGGTTG GTTCGAATGT
                                          2940
        *           *          *          *          *
ATGAGTTATG TTGTGTATTT TAAGACTCCA TATTACTTAA AGTAATGGGT
                                                    3000
        *           *          *          *          *
TGTTAATGTT GATGTGTGTG TATGCAGAAC CAACTTATGT ACGAGTCCAT

*           *          *          *          *
CAATGAGCTC CAAAAAAAGG TATGTAAAAC CCCTATCAAA TGTATGTCTT
         3060
        *           *          *          *          *
ATAGAGAAAC GTATAGGAAA GCTAATTAAC AATCGTGCCG TTTCGGAATG
                    3120
        *           *          *          *          *
ACAGGAGAAG GCCATACAGG AGCAAAACAG CATGCTTTCT AAACAGGAAC
                               3180
        *           *          *          *          *
ACATGTCATC ATTTCTCTTT CATCAACATG TTGTCCATTG CATTACTGTT
                                          3240
        *           *          *          *          *
ACCTTCCACT GTTCTGCTCC ACACTTCCAG CCAAGCTATA CCTACGATAT
                                                    3300
        *           *          *          *          *
CTTCATATCT CCACTTAACT TCGGCACCAT TAAATAAAAA TAGAAAATCT
```

FIG. 10D

```
                 *          *          *          *          *
        TTGCAAATTT GTTTGAAATA GCATAGATGT TGTCTATTGA TTGATATAAT
        3360
           *          *          *          *          *
        CACCAGCCTG TACGTAGATA TGGTTTGTCC GTTTAGTTTT AAGGTGTCTC
                       3420
           *          *          *          *          *
        TCGGATTGAA AATATTTTGA AATCTTTTGA AATGTTTGTC CCATCATTCT
                                  3480
           *          *          *          *          *
        TACTTAGCTC ATATCTATGT ATATGAATAT AGACACTACT CCTAATTATA
                                             3540
           *          *          *          *          *
        AAATGTTATA ATAGTTCATT GCATGAGTGC AACTGTGAAA ATAACTATTT
                                                        3600
           *          *          *          *          *
        GTAACCATTG CATATATATA GTTTCTTCAC TTTGAAAATT GATGATGATA
           *          *          *          *          *
        ATATGGTTTG AAATAAATTT GCTGGCAGAT CAAGGAGAGG GAAAAAATTC
        3660
           *          *          *          *          *
        TTAGGGCTCA ACAGGAGCAG TGGGATCAGC AGAACCAAGG CCACAATATG
                  3720
           *          *          *          *          *
        CCTCCCCCTC TGCCACCGCA GCAGCACCAA ATCCAGCATC CTTACATGCT
                       3780
           *          *          *          *          *
        CTCTCATCAG CCATCTCCTT TTCTCAACAT GGGGTAACAA AAAATTACTA
                                  3840
           *          *          *          *          *
        ATCAGTCTTA ATTTAAAGCA CATATGTTAT GCAAGCTAGT TACGTTAGGT
                                                        3900
           *          *          *          *          *
        GTTGTAATTT CATTGAAGTT ATAGCTGTTA GTGATGGTTA CATGATGCTA
           *          *          *          *          *
        GATTTTGAAA CTAGAAAACT TTATTTTAAA ACATTATTTT ATTAACGTAG
        3960
           *          *          *          *          *
        GTTAATGCAA TGGTCGCCAA ACGAACAAAC TTATTAGTGT GGAAAAATGT
                  4020
           *          *          *          *          *
        ACATGGAATG GTTGCGAAAA GCCTAAGTCG ACTTTTGTTG TTGTTGGTCT
                       4080
           *          *          *          *          *
        ATGTGTTTAA GTACAATTTT AGTTTGTTAG ATAAATGAAA TTAATATATC
                                  4140
                        FIG. 10E
```

```
         *          *          *          *          *
TTTGACATTT CACAATGGAC TGATATTTGA TTTTCCTTTG TTGTACGGTG
                                                  4200
         *          *          *          *          *
AAACATATGA TTACATATGC ACTTTCATAT ATATCCTATG TATGATTGTG
         *          *          *          *          *
AATGCAGTGG TCTGTATCAA GAAGATGATC CAATGGCAAT GAGGAGGAAT
4260
         *          *          *          *          *
GATCTCGAAC TGACTCTTGA ACCCGTTTAC AACTGCAACC TTGGCCGTTC
           4320
         *          *          *          *          *
GCCGCATGAA GCATTTCCAT ATATATATAT TTGTAATCGT CAACAATAAA
         *          *
AACTAGTTTG CCATCATACA TATAAATAG
```

FIG. 10F

```
                  *          *          *          *          *
         GCACCTGAGT CCGACTCCAA TGTAAACCAA TTTCTCTCCA TTAACTTATA
              60
               *          *          *          *          *
         TAAATTAAAT ATTATTTCAG TATTAGTGAT ATATACTTAT CTGTATTAAA
                        120
               *          *          *          *          *
         CTTGTGAGAT ATAGACGAAC TGGTCGATGG AGTATAATAG CTTAAGGCT
                                   180
               *          *          *          *          *
         AAGATTGAGC TTTTGGAGAG AAACCAGAGG TACATTTTCA TTCATCATTT
                                              240
               *          *          *          *          *
         ATATTAATAG ATGAAATATC AAACAGGATT AATGTTAGTT AAAAATGCAT
                                                         300
               *          *          *          *          *
         GATTACTTAT AAGAAAATGA TGCATTTAAA TAACAAAAAA ATGCATCGAT

*          *          *          *          *
         GCTCTATTGA AATTTAGGCA CTATCTTGGG GAAGACTTGC AAGCAATGAG
              360
               *          *          *          *          *
         CCCTAAGGAA CTCCAGAATC TAGAGCAACA GCTTGATACT GCTCTTAAGC
                        420
               *          *          *          *          *
         ACATCCGCTC TAGAAAAGTA TGAATCCTCC TATTTCTTTA ATTAACATGT
                                   480
               *          *          *          *          *
         ATACAACTTA AACACATATT ATTTTATTAT TCAATACATA TATATGAATA
                                              540
               *          *          *          *          *
         GTACATATGT GATTTTATTG GTTGGATATA AAAGATCAAT CACGTCGATT
                                                         600
               *          *          *          *          *
         AGATGTATGA CTTTTTAAAG AATTAGTATA TAGAGTATGA TTAGTCAATG

*          *          *          *          *
         TAATGGTACG TACGTTTATG CAGAACCAAC TTATGTACGA CTCCATCAAT
              660
               *          *          *          *          *
         GAGCTCCAAA GAAAGGTATG TATAAACCCT ATCAAATTGA CGTTTACATA
                        720
               *          *          *          *          *
         GAATAACTGC GTGTAAGAAT CCTATAGGGG AGCTAACAAT CGTGCCGTTT
                                   780
               *          *          *          *          *
         TGGAAATGAC AGGAGAAAGC CATACAGGAA CAAAACAGCA TGCTTTCCAA
                                              840
               *          *          *          *          *
```

FIG. IIA

```
GCAGGTGCCA TTTGTCATTA TTTTTATATC GTCAAAATGT TTTCTATTGT
                                                  900
             *          *          *          *    *
AGTACTGTTA GCTTCCACTG TTCTACTCCA CACTTCAAGC CAAGCTATAC
     *          *          *          *          *
CTACCTACGA CTACGAGATT CTCCACATAT TTCTCCACTT AGCTTCGGCA
      960
       *          *          *          *          *
CCACTATAAC TAAAATATAG ATAAAATATC ATTTTTATAG TCTATGATTG
               1020
                *         *          *          *
ATATACTCGT CAGCCAGTAC GTAGTTGGGT ATTTGCCCGT TTAGTTTTAA
                         1080
                           *          *          *
GGTTCTTTTC CGGATTGAAA ATATTT---- -ACCCTACCT TTGATGCTAT
                                     1140
      *          *          *          *          *
TATATGTATA TCTATTTAGA AGTCGTGGCT TTGAAAATTG ATGATGATAT
                                                  1200
      *          *          *          *           *
GTATGGTATA AGTTGGTAAC AAACTGGTGT GTGAAATTGA AACTTGTCAG
      *          *          *          *          *
ATTAAGGAGA GGGAAAACGT TCTTAGGGCG CAACAAGAGC AATGGGACGA
    1260
     *          *          *          *          *
GCAGAACCAT GGCCATATAT GCCTCCGCCT CCACCCCCGC AGCAGCATCA
               1320
                *         *          *          *
AATCCAGCAT CCTTACATGC TCTCTCATCA GCCATCTCCT TTTCTCAACA
                          1380
      *          *           *         *          *
TGGGGTAGTT AAAAATTCGT TCCTCTTACT TTCAAGTCAT ATGTGTATAT
                                    1440
      *          *          *         *          *
ATACAAGATA GTTAGGTGTT ATAAGTCCAG TGAGTTAGGT TGTGTTAGTG
                                                  1500
      *          *          *          *           *
ATGGTTAGAT GTCTAGATTG TGAATTACAA GTACTAAGAT TTTTCAGTTA
      *          *          *          *          *
TATAATTAAC GTATTGATCA TCAATCAAAT GGTCGTAAAA AAACAGACTT
    1560
     *          *          *          *          *
ATATTTTTGG GAAAGTAGAT GGAATGGCTG CTAAAAGTCT AAGAAACCTT
               1620
                 *        *          *          *
TGGGAGCAGG TCGTATTTAT TGTTGTTCAA ATTAAACTTG AGGTAGTTAG
```

FIG. 11B

```
                              1680
     *          *              *            *            *
ATAAATAAAC  TATCTTTGAT  ATGGCCTTTA  CCAATTTCAC  TACAAAACAT
                                           1740
     *          *              *            *            *
GTGATATTTT  CAGCACCTAT  GTAGATAATT  TGTAAGCTAT  ATCATGTGCA
                                                        1800
     *          *              *            *            *
TATGAATGTA  AATGCAGGGG  GCTGTATCAA  GAAGAAGATC  AAATGGCAAT
     *          *              *            *            *
GAGGAGGAAC  GATCTCGATC  TGTCTCTTGA  ACCCGGTTAC  AACTGCAACC
    1860
     *
TTGGCCGTCG  CCGCT
```

FIG. 11C

```
                    *          *          *          *          *
           GAGCTCTTCT TTATATCTCT TCTTGTAGTT TCTTGTTTCG TTTGGTTCTC
                60
                *          *          *          *          *
           TTAGAGGAAA TAGTTCCTTT AAAAGGGATA AAAATGGGAA GGGGTAGGGT
                          120
                *          *          *          *          *
           TCAGTTGAAG AGGATAGAAA ACAAGATCAA TAGACAAGTG ACATTCTCGA
                                     180
                *          *          *          *          *
           AAAGAAGAGC TGGTCTTATG AAGAAAGCTC ATGAGATCTC TGTTCTGTGT
                                                240
                *          *          *          *          *
           GATGCTGAAG TTGCGCTTGT TGTCTTCTCC CATAAGGGGA AACTCTTTGA
                                                           300
                *          *          *          *          *
           ATACCCCACT GATTCTTGGT AACTTTCTCA TTTAAGAAAC AAAA---TAC
                *          *          *          *          *
           CCTAAGATTG TATTTTACAT GATCATTTAC TTGTTTTACA CAGTATATAC
                360
                *          *          *          *          *
           TCTATGTATA TAATATGATC ATAAATTGTT GATGATAAGA AGCTAGCCCT
                          420
                *          *          *          *          *
           AATTCTGTGA ATTGAACAGT ATGGAGGAGA TACTTGAACG CTATGAGAGA
                                     480
                *          *          *          *          *
           TACTCTTACG CCGAGAGACA GCTTATAGCA CCTGAGTCCG ACTCCAATGT
                                                540
                *          *          *          *          *
           AAACCAATTT CTCTCCATTA ACTTATATAA ATTAAATATT ATTTCAGTAT
                                                           600
                *          *          *          *          *
           TAGTGATATA TACTTATCTG TATTAAACTT GTGAGATATA GACGAACTGG
                *          *          *          *          *
           TCGATGGAGT ATAATAGGCT TAAGGCTAAG ATTGAGCTTT TGGAGAGAAA
                660
                *          *          *          *          *
           CCAGAGGTAC ATTTTCATTC ATCATTTATA TATATGATGA AATATCAAAC
                          720
                *          *          *          *          *
           AGGATTAATG TTAGTTAAAA ATGCATGATT ACTTATAAAA AAATGATGCA
                                     780
                *          *          *          *          *
           TTTAAATAAC AAAAAAATGC ATCGATGCTC TATTGAAATT TAGGCACTAT
                                                840
                *          *          *          *          *
```

FIG. 12A

```
           CTTGGGGAAG ACTTGCAAGC AATGAGCCCT AAGGAACTCC AGAATCTAGA
                                                              900
                   *          *          *          *          *
           GCAACAGCTT GATACTGCTC TTAAGCACAT CCGCTCTAGA AAAGTATGAA

*          *          *          *          *
           TCCTCCTATT TCTTTAATTA ACATGTATAC AACTTAAACA CATATTATTT
                 960
                   *          *          *          *          *
           TATTATTCAA ATACATATAT ATAAATAGTA CATATGTGAT TTTATTGGTT
                                1020
                   *          *          *          *          *
           GGATTTGAAA AGATCAATCA CGTCGATTAG AATGTATGAC TTTTTAAAGA
                                           1080
                   *          *          *          *          *
           ATTAGTATAT AGAGTATGAT TAGTCAATGT AATGGATCGT TTATGCAGAA
                                                     1140
                   *          *          *          *          *
           CCAACTTATG TACGACTCCA TCAATGAGCT CCAAAGAAAG GTATGTATAA
                                                              1200
                   *          *          *          *          *
           ACCCTATCAA ATTGACGTTT ACATAGAATA ACTGCGTGTA AGAATCCTAT

*          *          *          *          *
           AGGGGAGCTA AAAATCGTGC CGTTTTGGAA ATGACAGGAG AAAGCCATAC
                1260
                   *          *          *          *          *
           AGGAACAAAA CAGCATGCTT TCCAAGCAGG TGCCATTTGT CATTATTTTT
                                1320
                   *          *          *          *          *
           ATTTCGTCAA AATGTTTTCT ATTGTAGATC TGTTAGCTTC CACTGTTCTC
                                           1380
                   *          *          *          *          *
           ACCACACTTC AAGCCAAGCT ATACCTACCT ACGACTAC-- -CCTACATTT
                                                     1440
                   *          *          *          *          *
           GATGCTATTT ATATGTATAT CTATTTAGAA GTCGTGGCTT TGAAAATTGA
                                                              1500
                   *          *          *          *          *
           TGATGATATG GTATGGTATA AGTTGGTAAC AAACTGGTGT GTGAAATTGA

*          *          *          *          *
           AACTTGTCAG ATTAAGGAGA GGGAAAACGT TCTTAGGGCG CAACAAGAGC
                1560
                   *          *          *          *          *
           AATGGGACGA GCAGAACCAT GGCCATAATA TGCCTCCGCC TCCACCCCCG
                                1620
                   *          *          *          *          *
           CAGCAGCATC AAATCCAGCA TCCTTACATG CTCTCTCATC AGCCATCTCC
```

FIG. 12B

```
                                    1680
    *             *             *             *             *
TTTTCTCAAC    ATGGGGTAGT    TAAAAATTCG    TTCCTCTTAC    TTTCAAGTAC

1740
    *             *             *             *             *
ATATGTGTTA    TATATACAAG    ATAGTTAGGT    GTTATAAGTC    CAGTGAGTTA

1800
    *             *             *             *             *
AGTTGTGTTA    GTGATGGTTA    GATGTCTAAA    TTGTGAAATA    CAAGTACTAA

*             *             *             *             *
GATTTTTCAT    GTATATATTT    AAACGTATTA    ATCATCAATC    AAATGGTCGT

1860
    *             *             *             *             *
AAAAGAAACA    GACTTATATT    TTTGGGAAAA    GTAGATGGAA    TGGCTGCTAA

1920
    *             *             *             *             *
AAGTCTAAGA    AACCTTTGGG    AGCAGGTCGT    TTTTATTGTT    GTTCAAATTA

1980
    *             *             *             *             *
AACTTGAGGT    AGTTAGATAA    ATAAACTATC    TTTGATATGG    GCCTTTACCA

2040
    *             *             *             *             *
ATTTCACTAC    AAAACATGTG    ATATTTTCAG    CACCTATGTA    GATAATTTTG

2100
    *             *             *             *             *
TAAGCTATAT    CATGTGCATA    TGAATGTAAA    TGTAGAGGGC    TGTATCAAGA

*             *             *             *             *
AGAAGATCAA    ATGGCAATGA    GGAGGAACGA    TCTCGATCTG    TCTCTTGAAC

2160
    *             *             *
CCGTTTACAA    CTGCAACCTT    GGCCGTCGCT    GCTGA
```

FIG. 12C

```
GGATCCCTCC GGAAGCCTTA GATCAATGGT AGTTGTGGTT ATTTTAAGAT
       60
CAGATTCTTT TGGAAATCCA GTAACATAGT CTGGGAATAT GATTTGCTTG
           120
TTGGTCACCG TTACTGCTTC TGCGTTCGTC ATTTCCGATT TTACGTACTT
                 180
TTGATCACTA TGATAATTTC TTCTTTCTTA CGTCGAGATG TGTCTGCTTT
                       240
TTGTAGATTG AATTTCTCAA TGTTGCTTTG ATCATAAGAC CATTTGATTT
                                   300
CTTTCCTTCA TTGATCGATC CAATTTCTTC GGGAGATAAA TAAGGTAAAA
ATGGACTATT ATTTTTGGAA AATACAGGAG AAAAAAATTC TTAAGAATAA
     360
AAGAGTATTT ATAGTGACCA TGAATTTTGT TGTTTTTTTA AAAAGAAAAA
         420
AAAACTCGAT TGGATTGGAT GACACATTGA AATTAACATT CAAATAGCAT
                480
CTTAGTTAAC AGATATTGCA TGCACCATAT AATAAAATAT CATAATTATG
                            540
TGTGATGCGA GGTTTGTTTT GGTCAAAATG TTATTTTAAT CACAATTTAA
                                         600
TAACAGATCA TTTACCAATT TGTTTTTTGA TAATTTATGC CAACTTAGTA
AATTCATCCA AAAAGTTGAA AAATATAGAT GTGTAATATG TTGACGGATA
     660
TACAACACTC AAAACAATAT ACTCAAAAAA AAAAAAAATT GAAAGCGGCA
             720
ACGATTCAAA CATATATGCT AAATTTTAAT AATGGACAAA GGAGGAAGTA
                       780
CTGCATATGT ACGAAAAGTG TTGATAATGG AGAGCAGCGG ATAGTGTCGC
                              840
```

FIG. 13A

```
CAAGGGCACG AGCTTTAGAT TCTTTTAGTT TGCTCTAAAT GTTCTTCTTT
                                                   900
     *         *          *          *          *
GGTACTTTTA ATTGCTTTAG TTGCTTGCTT CTTATCTCCA CATAAATAAA

*         *          *          *          *
TGGGGTAACC ATTTTCTCTC GTATCTTATT CCGATCTTTG GATCTATGTA
    960
     *         *          *          *          *
CGTACTACAT GAATAAATCG TGTTCAATAA GTTATTATCA TTTGGTCTGC
              1020
     *         *          *          *          *
TTAAAGTGAT CATGGTGTAT TAATCTATAA TACGTAGTTC TCTTAATTTA
                       1080
     *         *          *          *          *
TTCCCTAGAA TTCCATCAAA GACAAATTTT AGCAAAAAGA AAAGTTGAGT
                                  1140
     *         *          *          *          *
ATATAATTTG CTTAGTAGTA CAAAAAAAAA CTTTATGGTA ATTGTATTT
                                                  1200
     *         *          *          *          *
TGGATATTTC CTTNATTAAC CCAAACTTCA AAATTAATTT TCTTCTGCTG

*         *          *          *          *
TATCTTTATA TCCAACGTGA AATCTATTGA CTCAACAAAA TACACAGTTG
   1260
     *         *          *          *          *
TCAATTGAAG TTCAACTCTA CCAAGAAACA TCTATATGTA CTTCACTGTT
              1320
     *         *          *          *          *
CTTACCGCCG AGCAATTAAA ACCTCTATAA CTACTTGGTT ACATTATTAC
                       1380
     *         *          *          *          *
ATTTTTATTT ACAAAAAATA TATATCAACA ACCAATAATA TAGTTAGAAA
                                  1440
     *         *          *          *          *
ATGAAAGAAA ATTATTTAAG AAATATCCGC CGTCAATGCA AATCGAATGC
                                                  1500
     *         *          *          *          *
GACACTTGGG GAAGCTCTGA AGTCTGTGGT CTGTGCATAT TTCACTTGTC

*         *          *          *          *
TAGCTAACCC ATTTTCACGT CACTAGACGT CGATAATCAA TTATTGTTAT
   1560
     *         *          *          *          *
TTTTTTTATC AATGTTCCAC TTATTGAAAA TTATATACGA GAAAACATAG
              1620
     *         *          *          *          *
ACTCGACATT AGGCAATGGA AGTCTAATCA GACCAATGAG AAGTCGACAA
```

FIG. 13B

```
                          1680
       *         *         *         *         *
   CACATCCTAG AAACCAACTC TGGTTTATTT CCTTCCCTAA TACCAAGTTA

1740
       *         *         *         *         *
   TAGNNTTCTT TCAAACCGCT ATTTCCAAAA TATCTCTTCT TTAAATAAAG

1800
       *         *         *         *         *
   AGTGAAAGAA GCACTCTTTC ACATTACCAT CATTAGAAAA CTTTCCTAAT

*         *         *         *         *
   TAGATCAAGA TCGTCGTTAT CTCTCTTGTT TTTTCTTCAT ATAATTTAGT

1860
       *         *         *         *         *
   TATTTTAAGA GAAATGGGAA GGGGTAGGGT TGAATTGAAG AGGATAGAGA

1920
       *         *         *         *         *
   ACAAGATCAA TAGACAAGTG ACATTCTCGA AAAGAAGAAC TGGTCTTTTG

1980
       *         *         *         *         *
   AAGAAAGCTC AGGAGATCTC TGTTCTTTGT GATGCCGAGG TTTCCCTTAT

2040
       *         *         *         *         *
   TGTCTTCTCC CATAAGGGCA AATTGTTCGA GTACTCCTCT GAATCTTGGT

2100
       *         *         *         *         *
   AATTGCTTAA TTCCTTCTTT TTTTAATGTT ATTTTTAGTG TGCCTTCGTT

*         *         *         *         *
   TGCCCTAACT AGTAGTCTTT GTTCTACTTA AGGCATATTT TCTGTGTCTT

2160
       *         *         *         *         *
   CTATGCTATT ATCTGTCTTT GCTGAAAATT TGCCACTGAT TTGGTATCTA

2220
       *         *         *         *         *
   TTTACTTGGG ATCTACGAAC TGATTGTGTT GGTCATATCA TTAGTTTATT

2280
       *         *         *         *         *
   TTTATCAATA ATTTATTATA TATCAAAGAA AATGAAATTT TTTAGGACTT

2340
       *         *         *         *         *
   TTAGTGAACC CTACAATACG ATCTACTTAA TTATAGTGGC ATGGATTTGT

2400
       *         *         *         *         *
   AAGAAATCTT CAGCATCTTC TTTAATCTGG AAATGTACAT TTGCTTCAA

*         *         *         *         *
   GTCAAGTTTA GTATATTAGG TACAGAAAGA ACGGATGTTT ATGGTCTAGA

```
CTAGGGTTTT TGCTTTTAGG AAAGCTATAC TTTTGCTTAA ATATCTTTAA
              2520
           *       *          *         *         *
GTTGCATTTT ATGAACACAC ACACACATAT ATATATATAT ATATTAGTAT
                      2580
           *       *    *        *         *
ACCAATAATC TTAATTAAGT TTAGAAAGAA ACTCTTCATT TTTTCCCATT
                                2640
           *       *          *   *       *
TAATAATGGT TTATAGCTAG GTATAGAGAA ACTGGAAATA AGTATGTGAC
                                          2700
           *       *          *         *  *
ATCTAAGTAT GGGGAGTCTT TGACCTCTGG GGATTAATGT AAAACAGATC
           *       *          *         *         *
GTTCTTTTTT TTCTAAACAG TTCCTCCGTA CTGATGGTCA AACTTAACTT
    2760
     *     *       *          *         *         *
CAACAGTTCC TTTTAAACTT TTATAGGGTG CTTGAATACG TCTTGGGGTG
              2820
           *    *         *         *         *
TGGGGTTAGT GGCTCAACTG GTTTATTTAT TTTTAAAAAT GGTAGAAATC
                      2880
           *       *    *        *         *
AGTACTGTTT CTAGCTAGGG TTTAGGCACA AAACTAGAGA TCATCTTTAT
                                          2940
           *       *          *         *  *          *
TCCATAATAG AAAGGAAGAA ACTAATGTTT AATGACATAG ATTAATTAGA
                                                    3000
           *       *          *         *          *
TAACCCTACA TAATCAGATG CTATATGTTA TCACATATTT TGGGTGAATC
           *       *          *         *         *
GTTAATTACG TTTGAAACAA GTGGCCTCTT GTGCTAGCTG ATAAGATAGT
    3060
     *     *       *          *         *         *
TGNGTATGCA ATTATATTGG TGGTTGAATC CAAACTAATT CTAACTCGTA
              3120
           *    *         *         *         *
AGCTTAATAT TTGTAGCATG GAGAAGGTAC TAGAACGCTA CGAGAGGTAT
                      3180
           *       *    *        *         *
TCTTACGCCG AGAGACAGCT GATTGCACCT GACTCTCACG TTAATGTATG
                                3240
           *       *          *   *       *
TTTAATGGTC TCCATCATAT ATTTGTGTAT ATTTTGAATC TTGCATGTGT
                                          3300
           *       *          *         *  *
TTTAACATAG CATATAACTG ATTATTGGCT TTCATGTTGG AAATTAATTG
```

FIG. I3D

```
TGAAGGCACA GACGAACTGG TCAATGGAGT ATAGCAGGCT TAAGGCCAAG
     3360
ATTGAGCTTT TGGAGAGAAA CCAAAGGTAC ATAGTACATT TAAATTTATT
            3420
GTAGTAGTTA AATATTGAGG AATAACAGAA GAGAGAATGT TCTTAATTAA
                      3480
CTAAATCATC ATAGGCATTA TCTGGGAGAA GAGTTGGAAC CAATGAGCCT
                                3540
CAAGGATCTC CAAAATCTGG AGCAGCAGCT TGAGACTGCT CTTAAGCACA
                                                    3600
TTCGCTCCAG AAAAGTGTGT AAATATATCC CACACTCTAT CTCTATGCAT
AACTAACTTT GACTTTGTGT GGATGTATTA CATATAGTCA AATATTGTAT
     3660
AGAGATTGTC TCATATAAAT AAATAATTTT TGGCCTTTTT GTATGCAGAA
            3720
TCAACTCATG AATGAGTCCC TCAACCACCT CCAAAGAAAG GTAGCTAAGT
                      3780
TAAAACCATT TTATCTCTCA AGTCCTGTGT GTATAGAGTC ATGACTTATA
                                3840
TGTTAGAGAT ATAAATCTTT TAATAAATAA ATAACATATA GGTTATATAT
                                                    3900
AATTCAGGTT AATATATTAT TAATTACTAG ATGTATATAT ACTTATATAG
ATCATATAAA AAGAGAAATT GACAATGGTG TCATTTTTGT GGAAATGACA
     3960
GGAGAAGGAG ATACAGGAGG AAAACAGCAT GCTTACCAAA CAGGTGATCA
            4020
TTGTTTTTTG CATTTCTAAC TGTTTCACTA TTTACAATTC CACTGTTGAA
                      4080
CTCCACTTCA ATCTCTACCT TAACGTACCA TCTCTCCACT TTCGGCCCCA
                                                    4140
```

FIG. 13E

```
           *          *          *          *          *
    ACTCTTTTGA GTAAAAAGAA TTGATATGTA GTTTCTTTTG ATTGGTATAA

4200
           *          *          *          *          *
    TCATGAGCCT AGCTGCACGT ATAGGTAAGC TTTGTCCGTT TAGTATTAAG

*          *          *          *          *
    GTTGTCTCCC AGATTTGAAC TTGAACTTGA ACTGTCTTCT CATAATCATA
        4260
           *          *          *          *          *
    GTCTATGTGT AAATTACACA TACATTAGCT AGATAGCTAG GAGCTATATT

4320
           *          *          *          *          *
    TTAAGTTTTA TTGAGAAGTA AGAAAACGTA CGATGAAACT ACTTGATTAA

4380
           *          *          *          *          *
    GAACATATAT TAAATGAAAA AATATCACAA TAGTAAGACC TTGACGACGC

4440
           *          *          *          *          *
    TAAAATTCGC TTAACATTTT GCAGATTTAA TTATTACTTT GCATTTGTT

4500
           *          *          *          *          *
    TGAAAATATC ATATTACAAA AAAAAGTATA AGAATAAAAA ATTGAAGTTC

*          *          *          *          *
    CTTGAATAAA TGCAAATAGC TGATTAGTTG CAAATGGGAA TCTATATAAC
        4560
           *          *          *          *          *
    GATGATGCTT ATATCATTTT CTTGGCGTGT GTAATCGGTA TAGATAAAGG

4620
           *          *          *          *          *
    AGAGGGAAAA CATCCTAAAG ACAAAACAAA CCCAATGTGA GCAGCTGAAC

4680
           *          *          *          *          *
    CGCAGCGTCG ACGATGTACC ACAGCCACAA CCATTTCAAC ACCCCCATCT

4740
           *          *          *          *          *
    TTACATGATC GCTCATCAGA CTTCTCCTTT CCTAAATATG GGGTAACGGC

4800
           *          *          *          *          *
    AGTATTTCTT ATTTTTTTAA GTTCTTTTTT CTTACCATAA TGTCAAATTC

*          *          *          *          *
    TCATATATAG TGAAGTGTTG TCAGTCAGTC ATATAGGCAA TGATAGTGAA
        4860
           *          *          *          *          *
    TGCACTTCAT ATATAGGGTT TGTGTTAGGT ATGGCGTTAG AGGTTGATGG

4920
           *          *          *          *          *
    TATGCATGCA TATTATTGTA TTATGATTTT TAATTTGCTA TATATGATTG
```

FIG. 13F

```
                              4980
TAATTTCAGT GGTTTGTACC AAGGAGAAGA CCAAACGGCG ATGAGGAGGA

5040
ACAATCTGGA TCTGACTCTT GAACCCATTT ACAATTACCT TGGCTGTTAC

5100
GCCGCTTGAA TAGACTACAT CGATCTATAT CAATCTCTTT AAAATAATAT

AAGATCGATC CTCTATTCAT GATCTATATT AAACACCGGT TAATTAATAT

5160
ATTTTTGGTA TGTCCTTATA TCATATCAAC ATCATCAAGC CTTTTTCCAA

5220
TTCAATATAT CTTGTATTTC GGGGAGCAAT GAATAAATGT AATATTTGTG

5280
GACTGAGAGA GCTAGAAAGA ATTGTTGTTC AAACCTTTTC TATATTGATC

5340
TCATCGTTAC ATTGTAATTT GATTTCTTTC ACACCCCAAA ATATTTGTAA

5400
TACGAATTTA GTCTTTGATG ATTTGAACTT TACTTGGTCA AAGTAAATCA

CAGCCTTAGA AGGTAAATTT TGAATTGAAA ATAGAAATAA AAATGTTGGG

5460
AACGTGACAT TCGGTTTCTT CTCCATTTGC TTCATGTAGG TGCGTGATAC

5520
GATCGGAAAT GAGAATTATT GGGCCCTTGT GGGCTTCATA ATTATTAGTT

5580
CATTGTTTAA GCCCATAATA CTTGGCATTT TTGCCAAAGA AGAAACTGTA

5640
TAAAAGAAAT CGGAGAAGAA AAGAAAAATA GTAGTCGCGG CAATGGAGGA

5700
TCTATGGAAG AGGGCAAAAT CGTTCGCAGA AGAAGCGGGT AAGAAGTCTC

AGACGATAAC ACAATCATCC TCCGCGACCT TCGTCAATCT CGTCACCGAG
     5760
```

FIG. 13G

```
                *          *          *          *          *
            TCTAGATAAT CTTCTCAAGA AGGATTTAGA ATGGCATAAT CCAAAGGCTC
                60
                *          *          *          *          *
            AAATCTCGGC ATCTGAAACC ATATTATCAA TTTATTCATG ATTTAGGATG
                           120
                *          *          *          *          *
            CAACCAATTA AAAATAATCA GTGCATATGA TTTCATAAGT CTCTCGACCA
                                      180
                *          *          *          *          *
            AAACACTTTA CTACTCGATC ATGGTGCGAA ACAAGTCGAG AATGCTAGGT
                                                 240
                *          *          *          *          *
            CTATATGTGA TGCTTAGGCC ACACGGCATG TAATGTGATA CAACGATCCT
                                                            300
                *          *          *          *          *
            AGAGATCGGT TCTGAGATAT GCAAGCAAGG TCACACGACC ATTCATATAT
                *          *          *          *          *
            GGTGTCTCTC TAGGCCACAC GGCAAGCTAT GATGCATTAA GCCACACGGC
                360
                *          *          *          *          *
            TTTCAATCAC ATGATGCAAC AATGTGATCT ATCAAGGG-- ---CTCGAGC
                           420
                *          *          *          *          *
            TGCACACAGA CGGACGCGAG CTGGCTGTCG TCGGATGCGA GCTGAACGGG
                                      480
                *          *          *          *          *
            ACGGGACTCG TCTGCTTCCT ATCGGGTTCG CGAGCTGCTT CCTATCGGGT
                                                 540
                *          *          *          *          *
            TTTCAAGCGG CTGATCGGA TTACAAGCTG GTTGATCAGG AACACGAGCT
                                                            600
                *          *          *          *          *
            GGCTGTGATG CGAACGGAAG CTGAGGTTGT CTAGGATCAG GAACACCTTA
                *          *          *          *          *
            GGGATGGAGC TGATCGGTTG CTGACGAGCT GGAACGCGAG CTAGGACGAA
                660
                *          *          *          *          *
            TTAGGGTTCG TCGGGATTAG GTTAAAGTCG CCGGCTAGGT TAGGTTTAAG
                           720
                *          *          *          *          *
            GGATTGGCGA TTTTAGCTTA GATTGCAGAG AACAATCGTG CTGATAACAT
                                      780
                *          *          *          *          *
            GTTGTAATTA GAAGATTGAA GATTGAATAG TTCTGTGTTT TATTAACATA
                                                 840
                *          *          *          *          *
```

FIG. 14A

```
ACATGAATT- ----AAAGAT TCCACGAGTT TCGTACATGT TCTATTGCTA
                                                   900
     *          *          *          *          *
GTTAGGTTAA GGGAGTTAAG CAAAGTAGAG TGATTGGCAT TAACTCTTCA
     *          *          *          *          *
GTAGTGCCCA CGAAGACTCT AGTTAGAAGT CAGTTCAATC TGACAAGCTG
    960
     *          *          *          *          *
TTAGAGGTTC ACTAACACTT GAGTTTGGAT CTTGAAGGTC CATATAATAG
               1020
     *          *          *          *          *
TATAACGTAG ACCCAATATA ATACAAAACT ATAGTATTGA CTATAAATTT
                          1080
     *          *          *          *          *
GAGTGTCTAC ACCAACTCGT TTAAGCAAGA CAGGTCCCGA GACCGGAGTG
     *          *
GTTTCTTTGT TGAGCTC---
```

FIG. 14B

```
                 *              *              *              *              *
         AAGCTTTAGG     GTTTTAGGGT     TTTTGATTCC     AAGATTTAGG     GTTTTCATAA
                  60
                  *              *              *              *              *
         TTCAGATCAG     AACAATCAAT     CAACATGTTC     TAATGGAATC     GATTTCAATC
                                120
                  *              *              *              *              *
         TAGTGATTAT     AAGATGATCA     GTTTTAGGTT     ATACCAATTT     TTAGGATTTA
                                               180
                  *              *              *              *              *
         TCAAGATCAT     TGGATTTCCA     TAATAATGGA     TTAGGGTTTT     AGGGTTTGAT
                                                              240
                  *              *              *              *              *
         CATTATGTTT     TTAGATTAAT     CGGTATACTT     TTGTTTGTAG     GGTTGAAACC
                                                                            300
                  *              *              *              *              *
         GGACCACCAA     AGAGAACGGA     TGAACCTCGA     GCTGCACACC     GACAGATGCG
                  *              *              *              *              *
         AGCTGGCTGT     CGTCGGATGC     GAGCTGAACG     GGACGGGACG     CGTCTGCTTC
                 360
                  *              *              *              *              *
         CTATCGGGTT     CGCGAGCTGC     TTCCTATCGG     GTTTGCAAGC     GGCTGATCGG
                                420
                  *              *              *              *              *
         GATTGCGAGC     TGGTTGATCG     GGAACACGAG     CTGGCTGTGA     TGCGAACGGA
                                               480
                  *              *              *              *              *
         AGCTGAGGTC     GTCTAGGATC     AGGAACACCT     TAGGGATGGA     GCTGATCGGT
                                                              540
                  *              *              *              *              *
         TGCTGACGAG     CTGGAACGCG     AGCTAGGACA     AATTAGGGTT     CGTCGGGATT
                                                                            600
                  *              *              *              *              *
         AGGTTAAAGT     CGCCGGCTAG     GTTAGGTTTA     AGGGATTGGC     GATTTTAGCT
                  *              *              *              *              *
         TAGATTGCAG     AGAACAATCG     TGCTGATAAC     GTGTTGTAAA     ACAAACGGTT
                 660
                  *              *              *              *              *
         TTAGAAACTG     AATGTTTATG     TGTATTATTA     ATCATAATAT     GGGTTTTTT-
                                720
                  *              *              *              *              *
         ---------T     ACAGTGCGAG     AATGATAGAC     TCGCATAGCC     AATGAAGTCC
                                               780
                  *              *              *              *              *
         AGTCAGACCA     ATGAGAAGTC     GACAGCAAAA     CCTAGTAAAC     TACTCTTGTT
                                                              840
                  *              *              *              *              *
```

FIG. 15A

```
TTATCCTTGT CCAAAACCAG CTTTAGGTTT CCCTGAAACC GCTTATTCCA
                                                    900
                *         *         *         *     *
AAACATCTTC TCCTTAAATA AAGAAAGACT CTTTCACATT GTTATTATCA
    *         *         *         *         *
TCAGAAGGGA AAGAAGAAAA ACTTTCCTAA TTAGATCGAG CTTGTCGTTA
      960
       *         *         *         *         *
TCTCTCTATT ATAGTTTATA TTTCTTACTG GGCTTGTTT GGTTGCTTCT
          1020
            *         *         *         *         *
CTTTTTGGAC TTCTTTTATA TAATTTATAT ATTCTACGAG AAATGGGAAG
                    1080
            *         *         *         *         *
GGGTAGGGTT GAAATGAAGA GGATAGAGAA CAAGATCAAC AGACAAGTGA
                              1140
      *         *         *         *         *
CGTTTTCGAA AAGAAGAGCT GGTCTTTTGA AGAAAGCCCA TGAGATCTCG
                                                   1200
       *         *         *         *         *
ATTCTTTGTG ATGCTGAGGT TTCCCTTATT GTCTTCTCCC ATAAGGGGAA
       *         *         *         *         *
ACTGTTCGAG TACTCGTCTG AATCTTGGTA ACTGCATAAT TCCCTTTTTA
   1260
    *         *         *         *         *
ATTGTTTTAG TGTGCCTTTG TTCGCCCTAA TAAATAGTTT TTGTTCTCCT
          1320
            *         *         *         *         *
TTAGGCCATT TCTTGGTATC TTCTTATGTT TTTATGAAAA TTCTCACAAA
                    1380
            *         *         *         *         *
TTTTGTAGTT AATTACTTGG ATCTACGAAT TGATTTCACC AAAGTGAAAT
                              1440
       *         *         *         *         *
TAAACCATTA TAGCATATTT GCTTATATCA GAAGAAAATA AAAAAAATAG
                                                   1500
       *         *         *         *         *
GGCATAATAA GGTGTTATGT GAAGTGAAAG TTTACTTCAG GTAACACGTT
       *         *         *         *         *
ATTAAGATAT GCTTAACCCT AGATCAAGAT CTACTTCTAC TGGTCGCGAC
  1560
   *         *         *         *         *
ATGGATTTAC AAGAAATCGT CACTGTATAT GAACTTTAAT TTAAACATGT
             1620
               *         *         *         *         *
ATAGACCTTT TTGTTTCAAA TAGAGAGTTA AGTAATTTAA TCATAGAAAG
```

FIG. 15B

```
                              1680
         *         *           *           *          *
    AACCAACGTT ATGTTCATCT AGGCTAGAGT GATTTTTGCC TAACAATTTT

1740
         *         *           *           *          *
    GAAAAGCTGT CCTTATGCTT AAATATCTTT CAGCAGCATA GTAGTATGAA

1800
         *         *           *           *          *
    AGAAAATATT TCAATATCGT TGTATAAAGG TTCTATAATT TTCGTTTTTT

*         *           *           *          *
    TTTTTTTCGC AAATGGTTTA TATAGAGAAA CTAGAACTAG GGATGTGACA

1860
           *         *          *           *          *
    TCTAGGTATA GGGGTCTTTG ACCTCTGGGA TCAATGTAAA AGAGACCATT

1920
           *         *          *           *          *
    CTATTTTCTA TCAACTTCTC AGTTTCCGAT GGTCAAAACT TAACTTCAAC

1980
         *         *           *           *          *
    AACTGTTTTT CTTTTCAGAA GAGGACAAAC TATTATATGT ATATTATGTT

2040
         *         *           *           *          *
    ATGTCGTTTC ATACATAAAT ATCTAATAAC AAATTTATTT TTAAAAACAT

2100
         *         *           *           *          *
    ATAACAAAAC TTTATTGAAG AATTGGAAAC TCAAAACGGG GACATATAGG

*         *           *           *          *
    ACGCTGCACG TCTAGAGGTG TGGGGTTAGT GATTCAACGG GTTTTTAATG

2160
           *         *          *           *          *
    TAGAGAAACT GTAGATGTAA GATTGTTTCT AGGGTTAAGG CACTAAACCA

2220
           *         *          *           *          *
    GGGATTATCT CTTTTCCATG ATAAAAGTTA ATGTCTTAAA TGCATCGCTA

2280
         *         *           *           *          *
    ATTAATTAGG CAAACTAGAT GATAGTACGT AGTGTGTGTG TGTGTGTGTA

2340
         *         *           *           *          *
    TTGGATATTT TGGGTTAATA GTTACATCTT AGACAAATGT GTGGTCTTCT

2400
         *         *           *           *          *
    GATAAGCTGA GAAAATATTT GGGTGCAGAC TCTTAGTGGT AATTAATTAT

*         *           *           *          *
    ATCTAGAAAN NCCCANATAC NAATTTAATA CGGCTACTTT TTGGGTGAAT

```
GAATCTACAC TAACCCTAAG CCTAATGATA GCATGGAGAA GGTACTAGAA
                  2520
          *        *         *         *         *
CGCTACGAGA GGTACTCTTA CGCCGAGAAA CAGCTAAAAG CTCCAGACTC
                            2580
          *        *         *         *         *
TCACGTCAAT GTATGTTTAA TGATCTCCAA GACTCTGTCA AACATATATG
                                          2640
          *        *         *         *         *
TACTATATCT TGAATGTGTT TTCTTAATTA ACATAATTGA TGCACTGTTT
                                                    2700
          *        *         *         *         *
ACATAATGAA AATTAATTGT GTAGGCACAA ACGAACTGGT CAATGGAATA
          *        *         *         *         *
TAGCAGGCTT AAGGCTAAGA TTGAGCTTTG GGAGAGGAAC CAAAGGTACT
    2760
    *              *         *         *         *
TATAGAATTT AGGAATTAGC ATGTGTAAAT AATAGTTTAT TGTATTAGTT
                  2820
          *        *         *         *         *
TTTTTTGGTA AAATTATTGT ATTAGTTAAA CACTGGGAAT TAACAAAAAA
                            2880
          *        *         *         *         *
GATGGTGGTA TGGATTAATC ATAGGCATTA TCTGGAGAA GATTTAGAAT
                                          2940
          *        *         *         *         *
CAATCAGCAT AAAGGAGCTA CAGAATCTGG AGCAGCAGCT TGACACTTCT
                                                    3000
          *        *         *         *         *
CTTAAACATA TTCGCTCCAG AAAAGTGTGT AAATAAGCAC ATACAAACGC
          *        *         *         *         *
AAACATCTCT ATCTTATCTT TGAGTTTGTG AAGATATATA TGCCTAATTT
    3060
    *              *         *         *         *
TATATAGAGT TTGTCTCATA TGAATGAATA CAATTTGAAC TCAATTGTAT
              3120
          *    *             *         *         *
GCAGAATCAA CTAATGCACT AGTCCCTCAA CCACCTCCAA AGAAAGGTAC
                        3180
          *        *    *             *         *
GTTAAAACCA TTTCATCTCT CAAGTCGTAC GTGTGTATGT GTGACTTATG
                                          3240
          *        *         *         *         *
TTACCGTTTA AATCTTTCAG TTAAATACAA AACATATGGT TTTACACATG
                                                    3300
          *        *         *         *         *
TTAGACTATT TTGGTGAAGG AAACATTGTA AATGTAAACA AAGGGGTTTT
```

FIG. 15D

```
                  *          *          *          *          *
       TTGGATTGAA TAAAATTTAA CATTCATTCA AAAAAAACAT ATGGTTCATA
       3360
          *          *          *          *          *
       TATATATTCG GTTTATATGA TTATATATAT ATATTTATAT AGGTTAATAT
                       3420
          *          *          *          *          *
       ATTAGTGTTT AATTATATGT GTATACATAT AGATGTAGAA AGAACCTCTA
                                  3480
          *          *          *          *          *
       GAGCGATCCC TGAGAATTGT TTCATTTTGT AAAATTGACA GGAGAAAGAA
                                              3540
          *          *          *          *          *
       ATACTGGAGG AAAACAGCAT GCTTGCCAAA CAGGTAATCA TTGTATGTTG
                                                         3600
          *          *          *          *          *
       CATTTTTTAC TGTTTCACAA CTGTTTTACT ATTTAAACTC CACTGTTCTA
          *          *          *          *          *
       CTCCACTTCA ACCTTAAACT ACCATTGCTC AACTTTCGGC ACCAACTCTT
       3660
          *          *          *          *          *
       TTTTAAAAAG GAAGAATTAG TTGTTTCATG TGATTGGTAT AATCATGAGC
                       3720
          *          *          *          *          *
       ATATGTGCAC ACATGTAGGT GGGCTTTGTC CGTTTAGTAT TAAGGTTGTC
                                  3780
          *          *          *          *          *
       TCCTAGAATT GAACTTGAAC TGTCTTCTCG TAATCATAGT CTATATATAA
                                              3840
          *          *          *          *          *
       CACGCTGCAC ATACAGTAGC CAGTAGGTTT ATTTGAGCAA GATAC-----
                                                         3900
          *          *          *          *          *
       ---TGCTCTT ACTGTAATAC CGTGCCAACA TTGATTGTGA TTCGATACAT
          *          *          *          *          *
       AAATTTAGTT GATCATAACG TTTATCGGTA TTTGAAATTG GTAGATAAAG
       3960
          *          *          *          *          *
       GAGAGGGAGA GTATCCTAAG GACACATCAA AACCAATCAG AGCAGCAAAA
                       4020
          *          *          *          *          *
       CCGCAGCCAC CATGTAGCTC CTCAGCCGCA ACCGCAGTTA AATCCTTACA
                                  4080
          *          *          *          *          *
       TGGCATCATC TCCTTTCCTA AATATGGGGT AACGGTAGTG TTTCATTTTT
                                              4140
                          FIG. 15E
```

```
           *          *          *          *          *
    ATCTTGGTAT ACATATATAC ATATAGATCC GACACTCTTG GTGTTAGTAA
                                                      4200
           *          *          *          *          *
    TTCAGTGTAT GCGATGATGT TGTATGTATG TATGTTCATA TTTAGGGTTT

*          *          *          *          *
    GTGTTAAGTG TGGCGTTAGA GGTTGATGGC TTTGTAACTA CATGTCTAGA
        4260
           *          *          *          *          *
    ACTATACAAT AATTAATAAG ATGGAATGAT ATATATATAT ACATATATTT
                4320
           *          *          *          *          *
    TAATTTGCCA TATGATTGTG ATTTCAGTGG CATGTACCAA GGAGAATATC
                                4380
           *          *          *          *          *
    CAACGGCGGT GAGGAGGAAC CGTCTCGATC TGACTCTTGA ACCCATTTAC
                                                4440
           *          *          *          *          *
    AACTGCAACC TTGGTTACTT TGCCGCATGA ATGGACTCGC CATATATCGA
                                                      4500
           *          *          *          *          *
    CATAAAATAA TTTATATAAG ATCGATTTTT ACGTATAATA ATAGGCAGCA

*          *          *          *          *
    ATGGTTAGCC ACCATATCTA TATACACTGG AAATTCTATT TATC----TT
        4560
           *          *          *          *          *
    ACATTGATTT ATACTACATA AACCCTCCAG ACCAAACTCG TCTCCATGCC
                4620
           *          *          *          *          *
    AACTGATAGA TTTCCTAGAC ATGCTACACA CTCCATGACT CCGACTAATT
                                4680
           *          *          *          *          *
    TTTGGTTTGG CGTTTTCTAT GTTTTTATTA ATTGTTTTGA ATTTTACTCT
                                                4740
           *          *          *          *          *
    TTCACGATAT TTAAAATTTT TCAAACTTAT TTTTGTTGCT CACAGTGAAC
                                                      4800
           *          *          *          *          *
    AAATCTTCTG TGAAGAAGTG GTATATATTC TGTGGAGCCA CTTCCCCAAT

*
    GTTCTTTGGT GGATCC
```

FIG. 15F

```
  T   K   K   I   K   G   I   Q   Q   A   T   A   G   V   Q   D   T   S   E   N   P   N   K   T   I   V   P
ACA AAG AAA ATC AAA GGG ATT CAG CAA GCC ACT GCA GGA GTC CAA GAC ACT TCG GAA AAT CCT AAC AAA ACA ATA GTT CCT 540

A   A   L   P   Q   L   T   P   T   L   V   L   E   V   E   P   E   L   Y   A   G   Y   D   S   V
GCA GCA TTA CCA CAG CTC ACC CCT ACC CTC GTG TCA GAA GTG GAG CCC GAG TTG TAT GCA GGA TAT GAT AGC TCT GTT 570

P   D   S   A   A   I   R   M   T   T   L   N   M   A   A   V   K   W   A   K   A   L   C   I   A   L
CCA GAT TCA GCA GCA ATT AGA ATG ACC ACA CTC AAC ATG GCA GCA GTG AAA TGG GCA AAA GCA TAT GAT AGC ATA CTA 600

G   L   R   N   L   H   L   D   Q   M   T   L   L   Q   M   F   L   M   A   F   L   G   M   Y   R   S
GGC TTG AGA AAC CAC ATG GAT CAA CAG CTA CTG CTA CAG ATG TTT CTC GCA TTT CTT GGT TGG AGA TCA 630

Y   R   Q   S   S   G   N   E   I   I   N   E   Q   E   Y   L   C   M   Y   L   D   Q
TAC AGA CAA TCA AGC GGA AAC GAA ATT ATT AAT GAG CAG GAG TAT TTA CTC ATG TAT GAC CAA 660

C   K   H   M   L   F   V   S   S   Y   V   S   Q   L   Q   R   L   Q   M   T   L   L   L   L
TGT AAA CAC ATG CTG TTT GTC TCC TCT TAT GTA TCC CAG TTA CAA AGA TTG CAG ATG ACC TTA CTC CTT CTC 690

S   V   P   K   E   G   S   S   L   K   Q   E   I   F   D   E   I   R   M   T   Y   I   K   A   I   V
TCC TCA GTT CCT AAG GAA GGT AGT TCC AGT CTG AAG CAA GAG ATT TTT GAT GAG ATT CGA ATG ACT TAT ATC AAA GCC ATC GTC 720

K   R   E   G   N   S   Q   N   W   D   K   T   M   S   I   E   P   L   K   S   M   H   E   V   E   N   L
AAA AGG GAA GGG AAC TCC AGT CAG AAC TGG GAT AAG ACC ATG AGT ATT GAA CCA CTG AAA AGC ATG CAT GAG GTT GAA AAT CTC 750

L   Y   S   N   I   K   L   F   Q   T   F   L   D   K   I   E   F   P   E   M   A   E   I   I   T   N   Q   I   P
CTT ACC TAC TCA AAT ATC AAA AAG CTT TTC CAG ACA TTT TTG GAT AAG ATT GAA TTT CCA GAG ATG GCT GAG ATC ATC ACT AAT CAG ATA CCA 780

K   Y   S   N   G   N   I   K   L   F   H   Q   K stop
AAA TAT TCA AAT GGA AAT ATC AAA AAG CTT CTG TTT CAT CAA AAA TGA
```

Figure 16

CAULIFLOWER FLORAL MERISTEM IDENTITY GENES AND METHODS OF USING SAME

This application is a divisional of application U.S. Ser. No. 08/592,214, filed Jan. 26, 1996 U.S. Pat. No. 5,811,536.

This work was supported by grant DCB-9018749 awarded by the National Science Foundation. The United States Government has certain rights in this invention.

BACKGROUND OF THE INVENTION

1. Field of the Invention

This invention relates generally to the field of plant flowering and more specifically to genes involved in the regulation of flowering.

2. Background Information

A flower is the reproductive structure of a flowering plant. Following fertilization, the ovary of the flower becomes a fruit and bears seeds. As a practical consequence, production of fruit and seed-derived crops such as grapes, beans, corn, wheat and rice is dependent upon flowering.

Early in the plant life cycle, vegetative growth occurs, and roots, stems and leaves are formed. During the later period of reproductive growth, flowers as well as new shoots or branches develop. However, the factors responsible for the transition from vegetative to reproductive growth, and the onset of flowering, are poorly understood.

A variety of external signals, such as length of daylight and temperature, affect the time of flowering. The time of flowering also is subject to genetic controls that prevent young plants from flowering prematurely. Thus, the pattern of genes expressed in a plant is an important determinant of the time of flowering.

Given these external signals and genetic controls, a relatively fixed period of vegetative growth precedes flowering in a particular plant species. The length of time required for a crop to mature to flowering limits the geographic location in which it can be grown and can be an important determinant of yield. In addition, since the time of flowering determines when a plant is reproductively mature, the pace of a plant breeding program also depends upon the length of time required for a plant to flower.

Traditionally, plant breeding involves generating hybrids of existing plants, which are examined for improved yield or quality. The improvement of existing plant crops through plant breeding is central to increasing the amount of food grown in the world since the amount of land suitable for agriculture is limited. For example, the development of new strains of wheat, corn and rice through plant breeding has increased the yield of these crops grown in underdeveloped countries such as Mexico, India and Pakistan. Unfortunately, plant breeding is inherently a slow process since plants must be reproductively mature before selective breeding can proceed.

For some plant species, the length of time needed to mature to flowering is so long that selective breeding, which requires several rounds of backcrossing progeny plants with their parents, is impractical. For example, perennial trees such as walnut, hickory, oak, maple and cherry do not flower for several years after planting. As a result, breeding of such plant species for insect or disease-resistance or to produce improved wood or fruit, for example, would require many years, even if only a few rounds of selection were performed.

Methods of promoting early flowering can make breeding of long generation plants such as trees practical for the first time. Methods of promoting early flowering also would be useful for shortening growth periods, thereby broadening the geographic range in which a crop such as rice, corn or coffee can be grown. Unfortunately, methods for promoting early flowering in a plant have not yet been described. Thus, there is a need for methods that promote early flowering. The present invention satisfies this need and provides related advantages as well.

SUMMARY OF THE INVENTION

The present invention provides a nucleic acid molecule encoding a CAULIFLOWER (CAL) gene product. For example, the invention provides a nucleic acid molecule encoding *Arabidopsis thaliana* CAL and a nucleic acid molecule encoding *Brassica oleracea* CAL.

The invention also provides a nucleic acid molecule encoding a truncated CAL gene product. For example, the invention provides a nucleic acid molecule encoding the truncated *Brassica oleracea* var. *botrytis* CAL gene product. The invention also provides a nucleotide sequence that hybridizes under relatively stringent conditions to a nucleic acid molecule encoding a CAL gene product, a truncated CAL gene product, or a complementary sequence thereto.

The invention further provides the *Arabidopsis thaliana* CAL gene, *Brassica oleracea* CAL gene and *Brassica oleracea* var. *botrytis* CAL gene. In addition, the invention provides a nucleotide sequence that hybridizes under relatively stringent conditions to the *Arabidopsis thaliana* CAL gene, *Brassica oleracea* CAL gene or *Brassica oleracea* var. *botrytis* CAL gene, or a complementary sequence thereto.

The invention also provides vectors, including expression vectors, containing a nucleic acid molecule encoding a CAL gene product. The invention further provides a kit for converting shoot meristem to floral meristem in an angiosperm and a kit for promoting early flowering in an angiosperm.

In addition, the invention provides a CAL polypeptide, such as the *Arabidopsis thaliana* CAL polypeptide or the *Brassica oleracea* CAL polypeptide, as well as an antibody that specifically binds a CAL polypeptide. The invention further provides the truncated *Brassica oleracea* var. *botrytis* CAL polypeptide and an antibody that specifically binds the truncated *Brassica oleracea* var. *botrytis* CAL polypeptide.

The invention further provides a method of identifying a Brassica having a modified CAL allele by detecting a polymorphism associated with a CAL locus, where the CAL locus comprises a modified CAL allele that does not encode an active CAL gene product. For example, the polymorphism can be a restriction fragment length polymorphism and the modified CAL allele can be the *Brassica oleracea* var. *botrytis* CAL allele.

BRIEF DESCRIPTION OF THE DRAWINGS

FIGS. 1A and 1B illustrates the nucleotide (SEQ ID NO: 1) and amino acid (SEQ ID NO: 2) sequence of the *Arabidopsis thaliana* AP1 cDNA.

FIGS. 2A and 2B illustrates the nucleotide (SEQ ID NO: 3) and amino acid (SEQ ID NO: 4) sequence of the *Brassica oleracea* AP1 cDNA.

FIGS. 3A and 3B illustrates the nucleotide (SEQ ID NO: 5) and amino acid (SEQ ID NO: 6) sequence of the *Brassica oleracea* var. *botrytis* AP1 cDNA.

FIGS. 4A and 4B illustrates the nucleotide (SEQ ID NO: 7) and amino acid (SEQ ID NO: 8) sequence of the *Zea mays* AP1 cDNA. The GenBank accession number is L46400.

FIGS. 5A and 5B illustrates the nucleotide (SEQ ID NO: 9) and amino acid (SEQ ID NO: 10) sequence of the *Arabidopsis thaliana* CAL cDNA.

FIGS. 6A and 6B illustrates the nucleotide (SEQ ID NO: 11) and amino acid (SEQ ID NO: 12) sequence of the *Brassica oleracea* CAL cDNA.

FIG. 7 illustrates the nucleotide (SEQ ID NO: 13) and amino acid (SEQ ID NO: 14) sequence of the *Brassica oleracea* var. *botrytis* CAL cDNA.

FIG. 8 illustrates CAL gene structure and provides a comparison of various CAL amino acid sequences.

FIG. 8A. Exon-intron structure of Arabidopsis CAL gene. Exons are shown as boxes and introns as a solid line. Sizes (in base pairs) are indicated above. Locations of changes resulting in mutant alleles are indicated by arrows. MADS and K domains are hatched.

FIG. 8B. An alignment of three deduced amino acid sequences of CAL cDNAs. The complete *Arabidopsis thaliana* CAL amino acid sequence is displayed. The *Brassica oleracea* CAL (BoCAL) and *Brassica oleracea* var. *botrytis* CAL (BobCAL) amino acid sequences are shown directly below the Arabidopsis sequence where the sequences differ. The AP1 amino acid sequence is shown for comparison. The MADS domain is indicated in bold and the K domain is underlined. GenBank accession numbers are as follows: *Arabidopsis thaliana* CAL (L36925); *Brassica oleracea* CAL (L36926) and *Brassica oleracea* var. *botrytis* CAL (L36927).

FIGS. 9A and 9B illustrates the nucleotide (SEQ ID NO: 15) and amino acid (SEQ ID NO: 16) sequence of the *Arabidopsis thaliana* LEAFY (LFY) cDNA.

FIGS. 10A to 10F illustrates the genomic sequence of *Arabidopsis thaliana* AP1 (SEQ ID NO: 17).

FIGS. 11A to 11C illustrates the genomic sequence of *Brassica oleracea* AP1 (SEQ ID NO: 18).

FIGS. 12A to 12C illustrates the genomic sequence of *Brassica oleracea* var. *botrytis* AP1 (SEQ ID NO: 19).

FIGS. 13A to 13G illustrates the genomic sequence of *Arabidopsis thaliana* CAL (SEQ ID NO: 20).

FIGS. 14A and 14B illustrates the genomic sequence of *Brassica oleracea* CAL (SEQ ID NO: 21).

FIGS. 15A to 15F illustrates the genomic sequence of *Brassica oleracea* var. *botrytis* CAL (SEQ ID NO: 22).

FIG. 16 illustrates the nucleotide (SEQ ID NO: 23) and amino acid (SEQ ID NO: 24) sequence of the rat glucocorticoid receptor ligand binding domain.

DETAILED DESCRIPTION OF THE INVENTION

The present invention provides a nucleic acid molecule encoding a CAULIFLOWER (CAL) gene product, which is a floral meristem identity gene product involved in the conversion of shoot meristem to floral meristem. For example, the invention provides a nucleic acid molecule encoding *Arabidopsis thaliana* CAL and a nucleic acid molecule encoding *Brassica oleracea* CAL (BoCAL) (Kempin et al., *Science*, 267:522–525 (1995), which is incorporated herein by reference). As disclosed herein, a CAL gene product can be expressed in an angiosperm, thereby converting shoot meristem to floral meristem in the angiosperm or promoting early flowering in the angiosperm.

The invention also provides a nucleic acid molecule encoding a truncated CAL gene product such as a nucleic acid molecule encoding *Brassica oleracea* var. *botrytis* CAL (BobCAL). The invention also provides a nucleic acid molecule containing the *Arabidopsis thaliana* CAL gene, a nucleic acid molecule containing the *Brassica oleracea* CAL gene and a nucleic acid molecule containing the *Brassica oleracea* var. *botrytis* CAL gene. The invention further provides a kit for converting shoot meristem to floral meristem and a kit for promoting early flowering in an angiosperm. The invention provides a CAL polypeptide and an antibody that specifically binds CAL polypeptide. In addition, the invention provides the truncated BobCAL polypeptide and an antibody that specifically binds the truncated BobCAL polypeptide. The invention further provides a method of identifying a Brassica having a modified CAL allele by detecting a polymorphism associated with a CAL locus, where the CAL locus comprises a modified CAL allele that does not encode an active CAL gene product.

The present invention provides a non-naturally occurring angiosperm containing a first ectopically expressible nucleic acid molecule encoding a first floral meristem identity gene product. For example, the invention provides a transgenic angiosperm containing a first ectopically expressible floral meristem identity gene product such as APETALA1 (AP1), CAULIFLOWER (CAL) or LEAFY (LFY). Such a transgenic angiosperm can be, for example, a cereal plant, leguminous plant, oilseed plant, tree, fruit-bearing plant or ornamental flower.

A flower, like a leaf or shoot, is derived from the shoot apical meristem, which is a collection of undifferentiated cells set aside during embryogenesis. The production of vegetative structures, such as leaves or shoots, and of reproductive structures, such as flowers, is temporally segregated, such that a leaf or shoot arises early in a plant life cycle, while a flower develops later. The transition from vegetative to reproductive development is the consequence of a process termed floral induction (Yanofsky, *Ann. Rev. Plant Physiol. Plant Mol. Biol.* 46:167–188 (1995)).

Once induced, shoot apical meristem either persists and produces floral meristem, which gives rise to flowers, and lateral meristem, which gives rise to branches, or is itself converted to floral meristem. The fate of floral meristem is to differentiate into a single flower having a fixed number of floral organs in a whorled arrangement. Dicots, for example, contain four whorls (concentric rings) in which sepals (first whorl) and petals (second whorl) surround stamens (third whorl) and carpels (fourth whorl).

Although shoot meristem and floral meristem both consist of meristemic tissue, shoot meristem is distinguishable from the more specialized floral meristem. Shoot meristem generally is indeterminate and gives rise to an unspecified number of floral and lateral meristems. In contrast, floral meristem is determinate and gives rise to the fixed number of floral organs that comprise a flower.

By convention herein, a wild-type gene sequence is represented in upper case italic letters (for example, APETALA1), and a wild-type gene product is represented in upper case non-italic letters (APETALA1). Further, a mutant gene allele is represented in lower case italic letters (ap1), and a mutant gene product is represented in lower case non-italic letters (ap1).

Genetic studies have identified a number of genes involved in regulating flower development. These genes can be classified into different groups depending on their function. Flowering time genes, for example, are involved in floral induction and regulate the transition from vegetative to reproductive growth. In comparison, the floral meristem identity genes, which are the subject matter of the present invention as disclosed herein, encode proteins that promote the conversion of shoot meristem to floral meristem. In addition, floral organ identity genes encode proteins that determine whether sepals, petals, stamens or carpels are formed (Yanofsky, supra, 1995; Weigel, *Ann. Rev. Genetics* 29:19–39 (1995)). Some of the floral meristem identity gene products also have a role in specifying organ identity.

Floral meristem identity genes have been identified by characterizing genetic mutations that prevent or alter floral meristem formation. Among floral meristem identity gene mutations in *Arabidopsis thaliana*, those in the gene LEAFY (LFY) generally have the strongest effect on floral meristem identity. Mutations in LFY completely transform the basal-most flowers into secondary shoots and have variable effects on later-arising (apical) flowers. In comparison, mutations in the floral meristem identity gene APETALA1 (AP1) result in replacement of a few basal flowers by inflorescence shoots that are not subtended by leaves. An apical flower produced in an ap1 mutant has an indeterminate structure in which a flower arises within a flower. These mutant phenotypes indicate that both AP1 and LFY contribute to establishing the identity of the floral meristem although neither gene is absolutely required. The phenotype of lfy ap1 double mutants, in which structures with flower-like characteristics are very rare, indicates that LFY and AP1 encode partially redundant activities.

In addition to the LFY and AP1 genes, a third locus that greatly enhances the ap1 mutant phenotype has been identified in Arabidopsis. This locus, designated CAULIFLOWER (CAL), derives its name from the resulting "cauliflower" phenotype, which is strikingly similar to the common garden variety of cauliflower. In an ap1 cal double mutant, floral meristem that develops behaves as shoot meristem in that there is a massive proliferation of meristems in the position that normally would be occupied by a single flower. However, a plant homozygous for a particular cal mutation (cal-1) has a normal phenotype, indicating that AP1 can substitute for the loss of CAL in these plants. In addition, because floral meristem that forms in an ap1 mutant behaves as shoot meristem in an ap1 cal double mutant, CAL can largely substitute for AP1 in specifying floral meristem. These genetic data indicate that CAL and AP1 encode activities that are partially redundant in converting shoot meristem to floral meristem.

Other genetic loci play at least minor roles in specifying floral meristem identity. For example, although a mutation in APETALA2 (AP2) alone does not result in altered inflorescence characteristics, ap2 ap1 double mutants have indeterminate flowers (flowers with shoot-like characteristics) (Bowman et al., *Development* 119:721–743 (1993)). Also, mutations in the CLAVATA1 (CLV1) gene result in an enlarged meristem and lead to a variety of phenotypes (Clark et al., *Development* 119:397–418 (1993)). In a clv1 ap1 double mutant, formation of flowers is initiated, but the center of each flower often develops as an indeterminate inflorescence. Thus, mutations in CLAVATA1 result in the loss of floral meristem identity in the center of wild-type flowers. Genetic evidence also indicates that the gene product of UNUSUAL FLORAL ORGANS (UFO) plays a role in determining the identity of floral meristem. Additional floral meristem identity genes associated with altered floral meristem formation remain to be isolated.

Mutations in another locus, designated TERMINAL FLOWER (TFL), produce phenotypes that generally are reversed as compared to mutations in the floral meristem identity genes. For example, tfl mutants flower early, and the indeterminate apical and lateral meristems develop as determinate floral meristems (Alvarez et al., *Plant J.* 2:103–116 (1992)). These characteristics indicate that the TFL promotes maintenance of shoot meristem. TFL also acts directly or indirectly to negatively regulate AP1 and LFY expression in shoot meristem since AP1 and LFY are ectopically expressed in the shoot meristem of tfl mutants (Gustafson-Brown et al., *Cell* 76:131–143 (1994); Weigel et al., *Cell* 69:843–859 (1992)). It is recognized that a plant having a mutation in TFL can have a phenotype similar to a non-naturally occurring angiosperm of the invention. Such tfl mutants, however, are explicitly excluded from the scope of the present invention.

The results of such genetic studies indicate that several floral meristem identity gene products, including AP1, CAL and LFY, act redundantly to convert shoot meristem to floral meristem and that TFL acts directly or indirectly to negatively regulate expression of the floral meristem identity genes. As disclosed herein, ectopic expression of a single floral meristem identity gene product such as AP1, CAL or LFY is sufficient to convert shoot meristem to floral meristem. Thus, the present invention provides a non-naturally occurring angiosperm that contains an ectopically expressible nucleic acid molecule encoding a floral meristem identity gene product, provided that such ectopic expression is not due to a mutation in an endogenous TERMINAL FLOWER gene.

As disclosed herein, an ectopically expressible nucleic acid molecule encoding a floral meristem identity gene product can be, for example, a transgene encoding a floral meristem identity gene product under control of a heterologous gene regulatory element. In addition, such an ectopically expressible nucleic acid molecule can be an endogenous floral meristem identity gene coding sequence that is placed under control of a heterologous gene regulatory element. The ectopically expressible nucleic acid molecule also can be, for example, an endogenous floral meristem identity gene having a modified gene regulatory element such that the endogenous floral meristem identity gene is no longer subject to negative regulation by TFL.

The term "ectopically expressible" is used herein to refer to a gene transcript or gene product that can be expressed in a tissue other than a tissue in which it normally is produced. The actual ectopic expression thereof is dependent on various factors and can be constitutive or inducible expression. As disclosed herein, AP1, which normally is expressed in floral meristem, is ectopically expressible in shoot meristem. As disclosed herein, when a floral meristem identity gene product such as AP1, CAL or LFY is ectopically expressed in shoot meristem, the shoot meristem is converted to floral meristem and early flowering can occur (see Examples II, IV and V).

In particular, an ectopically expressible nucleic acid molecule encoding a floral meristem identity gene product can be expressed prior to the developmental time at which the corresponding endogenous gene normally is expressed. For example, an Arabidopsis plant grown under continuous light conditions expresses AP1 just prior to day 18, when normal flowering begins. However, as disclosed herein, AP1 can be ectopically expressed in shoot meristem earlier than day 18, resulting in early conversion of shoot meristem to floral meristem and early flowering. As shown in Example IID, a transgenic Arabidopsis plant that ectopically expresses AP1 in shoot meristem under control of a constitutive promoter flowers earlier than the corresponding non-transgenic plant (day 10 as compared to day 18).

As used herein, the term "floral meristem identity gene product" means a gene product that promotes conversion of shoot meristem to floral meristem. As disclosed herein, expression of a floral meristem identity gene product such as AP1, CAL or LFY in shoot meristem can convert shoot meristem to floral meristem. Furthermore, expression of a floral meristem identity gene product in shoot meristem also can promote early flowering (Examples IID, IVA and V). A floral meristem identity gene product is distinguishable from a late flowering gene product or an early flowering gene product, which are not encompassed within the present invention. In addition, reference is made herein to an "inactive" floral meristem identity gene product, as exemplified by BobCAL (see below). Expression of an inactive floral meristem identity gene product in an angiosperm does not result in the conversion of shoot meristem to floral meristem in the angiosperm.

A floral meristem identity gene product can be, for example, an AP1 gene product such as Arabidopsis AP1, which is a 256 amino acid gene product encoded by the AP1 cDNA sequence isolated from *Arabidopsis thaliana* (FIGS. 5A and 5B, SEQ ID NO: 2). The Arabidopsis AP1 cDNA encodes a highly conserved MADS domain, which can function as a DNA-binding domain, and a K domain, which is structurally similar to the coiled-coil domain of keratins and can be involved in protein-protein interactions.

In Arabidopsis, AP1 RNA is expressed in flowers but is not detectable in roots, stems or leaves (Mandel et al., Nature 360:273–277 (1992), which is incorporated herein by reference). The earliest detectable expression of AP1 RNA is in young floral meristem at the time it initially forms on the flanks of shoot meristem. Expression of AP1 increases as the floral meristem increases in size; no AP1 expression is detectable in shoot meristem. In later stages of development, AP1 expression ceases in cells that will give rise to reproductive organs (stamens and carpels), but is maintained in cells that will give rise to non-reproductive organs (sepals and petals; Mandel, supra, 1992).

As used herein, the term "APETALA1" or "AP1" means a floral meristem identity gene product that is characterized, in part, by having an amino acid sequence that is related to the Arabidopsis AP1 amino acid sequence shown in FIGS. 1A and 1B (SEQ ID NO: 2) or to the *Zea mays* AP1 amino acid sequence shown in FIGS. 4A and 4B (SEQ ID NO: 8). In nature, AP1 is expressed in floral meristem.

CAULIFLOWER (CAL) is another example of a floral meristem identity gene product. As used herein, the term "CAULIFLOWER" or "CAL" means a floral meristem identity gene product that is characterized in part by having an amino acid sequence that has at least about 70 percent identity with the amino acid sequence shown in FIGS. 5A and 5B (SEQ ID NO: 10) in the region from amino acid 1 to amino acid 160 or with the amino acid sequence shown in FIGS. 6A and 6B (SEQ ID NO: 12) in the region from amino acid 1 to amino acid 160. In nature, CAL is expressed in floral meristem.

The present invention provides a nucleic acid molecule encoding a CAL, including, for example, the Arabidopsis CAL cDNA sequence shown in FIGS. 5A and 5B (SEQ ID NO: 9). As disclosed herein, CAL, like AP1, contains a MADS domain and a K domain. The MADS domains of CAL and AP1 differ in only five of 56 amino acid residues, where four of the five differences represent conservative amino acid replacements. Over the entire sequence, the Arabidopsis CAL and Arabidopsis AP1 sequences (SEQ ID NOS: 10 and 2) are 76% identical and are 88% similar if conservative amino acid substitutions are allowed.

Similar to the expression pattern of AP1, CAL RNA is expressed in young floral meristem in Arabidopsis. However, in contrast to AP1 expression, which is high throughout sepal and petal development, CAL expression is low in these organs.

LEAFY (LFY) is yet another example of a floral meristem identity gene product. As used herein, the term "LEAFY" or "LFY" means a floral meristem identity gene product that is characterized in part by having an amino acid sequence that is related to the amino acid sequence shown in FIGS. 9A and 9B (SEQ ID NO: 16) In nature, LFY is expressed in floral meristem as well as during vegetative development. As disclosed herein, ectopic expression of floral meristem identity gene products, which normally are expressed in floral meristem, such as AP1 or CAL or LFY or combinations thereof, in shoot meristem can convert shoot meristem to floral meristem and promote early flowering.

Flower development in Arabidopsis is recognized in the art as a model for flower development in angiosperms in general. Gene orthologs corresponding to the Arabidopsis genes involved in the early steps of flower formation have been identified in distantly related plant species, and these gene orthologs show remarkably similar RNA expression patterns. Mutations in these genes also result in phenotypes that correspond to the phenotype produced by a similar mutation in Arabidopsis. For example, orthologs of the *Arabidopsis floral meristem identity genes AP1* and LFY and the Arabidopsis organ identity genes AGAMOUS, APETALA3 and PISTILLATA have been isolated from monocots such as maize and, where characterized, reveal the anticipated RNA expression patterns and related mutant phenotypes. (Schmidt et al., *Plant Cell* 5:729–737 (1993); and Veit et al., *Plant Cell* 5:1205–1215 (1993), each of which is incorporated herein by reference). Furthermore, a gene ortholog can be functionally interchangeable in that it can function across distantly related species boundaries (Mandel et al., *Cell* 71:133–143 (1992), which is incorporated herein by reference). Taken together, these data suggest that the underlying mechanisms controlling the initiation and proper development of flowers are conserved across distantly related dicot and monocot boundaries. Therefore, results obtained using Arabidopsis can be predictive of results that can be expected in other angiosperms.

Floral meristem identity genes in particular are conserved throughout the plant kingdom. For example, a gene ortholog of Arabidopsis AP1 has been isolated from *Antirrhinum majus* (snapdragon; Huijser et al., *EMBO J*. 11:1239–1249 (1992), which is herein incorporated by reference). As disclosed herein, an ortholog of Arabidopsis AP1 also has been isolated from *Zea Mays* (maize; see Example IA). Similarly, gene orthologs of Arabidopsis LFY have been isolated from *Antirrhinum majus*, tobacco and poplar tree (Coen et al., *Cell*, 63:1311–1322 (1990); Kelly et al., *Plant Cell* 7:225–234 (1995); and Strauss et al., *Molec. Breed* 1:5–26 (1995), each of which is incorporated herein by reference). In addition, a mutation in the Antirrhinum AP1 ortholog results in a phenotype similar to the Arabidopsis ap1 mutant phenotype described above (Huijser et al., supra, 1992). Similarly, a mutation in the Antirrhinum LFY ortholog results in a phenotype similar to the Arabidopsis lfy mutant phenotype (Coen et al., supra, 1995). These studies indicate that AP1 and LFY function similarly in distantly related angiosperms.

A floral meristem identity gene product also can function across species boundaries. For example, Arabidopsis LFY can convert shoot meristem to floral meristem when expressed in aspen trees (Weigel and Nilsson, *Nature*

377:495–500 (1995), which is incorporated herein by reference). As disclosed herein, a nucleic acid molecule encoding an Arabidopsis AP1 or CAL gene product (SEQ ID NOS: 1 and 9), for example, also can be used to convert shoot meristem to floral meristem in an angiosperm. Thus, a nucleic acid molecule encoding an Arabidopsis AP1 gene product (SEQ ID NO: 1) or an Arabidopsis CAL gene product (SEQ ID NO: 9) can be introduced into an angiosperm such as corn, wheat or rice and, upon expression, can convert shoot meristem to floral meristem in the transgenic angiosperm. Furthermore, as disclosed herein, the conserved nature of an AP1 or CAL or LFY gene among diverse angiosperms, allows a nucleic acid molecule encoding a floral meristem identity gene product from essentially any angiosperm to be introduced into essentially any other angiosperm, wherein the expression of the nucleic acid molecule in shoot meristem can convert shoot meristem to floral meristem.

If desired, a novel AP1, CAL or LFY sequence can be isolated from an angiosperm using a nucleotide sequence as a probe and methods well known in the art of molecular biology (Sambrook et al. (eds.), *Molecular Cloning: A Laboratory Manual* (*Second Edition*), Plainview, N.Y.: Cold Spring Harbor Laboratory Press (1989), which is herein incorporated by reference). As exemplified herein and discussed in detail below (see Example IA), the AP1 ortholog from *Zea Mays* (maize; SEQ ID NO: 7) was isolated using the Arabidopsis AP1 cDNA as a probe (SEQ ID NO: 1).

In one embodiment, the invention provides a non-naturally occurring angiosperm that contains an ectopically expressible nucleic acid molecule encoding a floral meristem identity gene product and that is characterized by early flowering. As used herein, the term "characterized by early flowering," when used in reference to a non-naturally occurring angiosperm of the invention, means a non-naturally occurring angiosperm that forms flowers sooner than flowers would form on a corresponding naturally occurring angiosperm that does not ectopically express a floral meristem identity gene product, grown under the same conditions. Flowering times for naturally occurring angiosperms are well known in the art and depend, in part, on genetic factors and on the environmental conditions, such as day length. Thus, given a defined set of environmental conditions, a naturally occurring plant will flower at a relatively predictable time.

It is recognized that various transgenic plants that are characterized by early flowering have been described. Such transgenic plants are described herein and are readily distinguishable or explicitly excluded from the present invention. For example, a product of a "late-flowering gene" can promote early flowering but does not specify the conversion of shoot meristem to floral meristem. Therefore, a transgenic plant expressing a late-flowering gene product is distinguishable from a non-naturally occurring angiosperm of the invention. For example, a transgenic plant expressing the late-flowering gene, CONSTANS (CO), flowers earlier than a corresponding wild type plant (Putterill et al., *Cell* 80:847–857 (1995)). However, expression of exogenous CONSTANS does not convert shoot meristem to floral meristem.

Early flowering also has been observed in a transgenic tobacco plant expressing an exogenous rice MADS domain gene. Although the product of this gene promotes early flowering, it does not specify the identity of floral meristem and, thus, cannot convert shoot meristem to floral meristem (Chung et al., Plant Mol. Biol. 26:657–665 (1994)). Therefore, the early-flowering CO and rice MADS domain gene transgenic plants are distinguishable from the early-flowering non-naturally occurring angiosperms of the invention.

Mutations in a class of genes known as "early-flowering genes" also result in plants that flower prematurely. Such early flowering genes include, for example, EARLY FLOWERING 1–3 (ELF1, ELF2, ELF3); EMBRYONIC FLOWER 1,2 (EMF1, EMF2); LONG HYPOCOTYL 1,2 (HY1, HY2); PHYTOCHROME B (PHYB), SPINDLY (SPY) and TERMINAL FLOWER (TFL) (Weigel, supra, 1995). However, the wild type product of an early flowering gene retards flowering and is distinguishable from a floral meristem identity gene product in that it does not promote conversion of shoot meristem to floral meristem.

An Arabidopsis plant having a mutation in the TERMINAL FLOWER (TFL) gene flowers early and is characterized by the conversion of shoots to flowers (Alvarez et al., *Plant J.* 2:103–116 (1992), which is incorporated herein by reference). However, TFL is not a floral meristem identity gene product, as defined herein. Specifically, it is the loss of TFL that promotes conversion of shoot meristem to floral meristem. Since the function of TFL is to antagonize formation of floral meristem, a tfl mutant, which has lost this antagonist function, permits conversion of shoot meristem to floral meristem. Although TFL is not a floral meristem identity gene product and does not itself convert shoot meristem to floral meristem, the loss of TFL can result in a plant with an ectopically expressed floral meristem identity gene product. Such tfl mutants, in which a mutation in TFL results in conversion of shoot meristem to floral meristem, are explicitly excluded from the present invention.

As used herein, the term "non-naturally occurring angiosperm" means an angiosperm that contains a genome that has been modified by man. A transgenic angiosperm, for example, contains an exogenous nucleic acid molecule and, therefore, contains a genome that has been modified by man. Furthermore, an angiosperm that contains, for example, a mutation in an endogenous floral meristem identity gene regulatory element as a result of exposure to a mutagenic agent by man also contains a genome that has been modified by man. In contrast, a plant containing a spontaneous or naturally occurring mutation is not a "non-naturally occurring angiosperm" and, therefore, is not encompassed within the invention.

As used herein, the term "transgenic" refers to an angiosperm that contains in its genome an exogenous nucleic acid molecule, which can be derived from the same or a different species. The exogenous nucleic acid molecule that is introduced into the angiosperm can be a gene regulatory element such as a promoter or other regulatory element or can be a coding sequence, which can be linked to a heterologous gene regulatory element.

As used herein, the term "angiosperm" means a flowering plant. Angiosperms are well known and produce a variety of useful products including materials such as lumber, rubber, and paper; fibers such as cotton and linen; herbs and medicines such as quinine and vinblastine; ornamental flowers such as roses and orchids; and foodstuffs such as grains, oils, fruits and vegetables.

Angiosperms are divided into two broad classes based on the number of cotyledons, which are seed leaves that generally store or absorb food. Thus, a monocotyledonous angiosperm is an angiosperm having a single cotyledon, and a dicotyledonous angiosperm is an angiosperm having two cotyledons.

Angiosperms encompass a variety of flowering plants, including, for example, cereal plants, leguminous plants, oilseed plants, trees, fruit-bearing plants and ornamental flowers, which general classes are not necessarily exclusive. Such angiosperms include for example, a cereal plant, which produces an edible grain cereal. Such cereal plants include, for example, corn, rice, wheat, barley, oat, rye, orchardgrass, guinea grass, sorghum and turfgrass. In addition, a leguminous plant is an angiosperm that is a member of the pea family (Fabaceae) and produces a characteristic fruit known as a legume. Examples of leguminous plants include, for example, soybean, pea, chickpea, moth bean, broad bean, kidney bean, lima bean, lentil, cowpea, dry bean, and peanut. Examples of legumes further also include alfalfa, birdsfoot trefoil, clover and sainfoin. Furthermore, an oilseed plant is an angiosperm that has seeds useful as a source of oil. Examples of oilseed plants include soybean, sunflower, rapeseed and cottonseed.

A tree is an angiosperm and is a perennial woody plant, generally with a single stem (trunk). Examples of trees include alder, ash, aspen, basswood (linden), beech, birch, cherry, cottonwood, elm, eucalyptus, hickory, locust, maple, oak, persimmon, poplar, sycamore, walnut and willows. Such trees are used for pulp, paper, and structural material, as well as providing a major source of fuel.

A fruit-bearing plant also is an angiosperm and produces a mature, ripened ovary (usually containing seeds) that is suitable for human or animal consumption. Examples of fruit-bearing plants include grape, orange, lemon, grapefruit, avocado, date, peach, cherry, olive, plum, coconut, apple and pear trees and blackberry, blueberry, raspberry, strawberry, pineapple, tomato, cucumber and eggplant plants. An ornamental flower is an angiosperm cultivated for its decorative flower. Examples of ornamental flowers include rose, orchid, lily, tulip and chrysanthemum, snapdragon, camelia, carnation and petunia. The skilled artisan will recognize that the invention can be practiced on these or other angiosperms, as desired.

In various embodiments, the present invention provides a non-naturally occurring angiosperm having an ectopically expressible first nucleic acid molecule encoding a first floral meristem identity gene product, provided the first nucleic acid molecule is not ectopically expressed due to a mutation in an endogenous TFL gene. If desired, a non-naturally occurring angiosperm of the invention can contain an ectopically expressible second nucleic acid molecule encoding a second floral meristem identity gene product, which is different from the first floral meristem identity gene product.

An ectopically expressible nucleic acid molecule can be expressed, as desired, either constitutively or inducibly. Such an ectopically expressible nucleic acid molecule can be an endogenous nucleic acid molecule and can contain, for example, a mutation in its endogenous gene regulatory element or can contain an exogenous, heterologous gene regulatory element that is linked to and directs expression of the endogenous nucleic acid molecule. In addition, an ectopically expressible nucleic acid molecule encoding a floral meristem identity gene product can be an exogenous nucleic acid molecule encoding a floral meristem identity gene product and containing a heterologous gene regulatory element.

The invention provides, for example, a non-naturally occurring angiosperm containing a first ectopically expressible nucleic acid molecule encoding a first floral meristem identity gene product. If desired, a non-naturally occurring angiosperm of the invention can contain a floral meristem identity gene having a modified gene regulatory element and also can contain a second ectopically expressible nucleic acid molecule encoding a second floral meristem identity gene product, provided that neither the first nor second ectopically expressible nucleic acid molecule is ectopically expressed due to a mutation in an endogenous TERMINAL FLOWER gene.

As used herein, the term "modified gene regulatory element" means a regulatory element having a mutation that results in ectopic expression in shoot meristem of the floral meristem identity gene regulated by the gene regulatory element. Such a gene regulatory element can be, for example, a promoter or enhancer element and can be positioned 5' or 3' to the coding sequence or within an intronic sequence of the floral meristem identity gene. Such a modification can be, for example, a nucleotide insertion, deletion or substitution and can be produced by chemical mutagenesis using a mutagen such as ethylmethane sulfonate (see Example IIIA) or by insertional mutagenesis using a transposable element. For example, a modified gene regulatory element can be a functionally inactivated binding site for TFL or a gene product regulated by TFL, such that modification of the gene regulatory element results in ectopic expression of the floral meristem identity gene product in shoot meristem.

The invention also provides a transgenic angiosperm containing a first exogenous gene promoter that regulates a first ectopically expressible nucleic acid molecule encoding a first floral meristem identity gene product and a second exogenous gene promoter that regulates a second ectopically expressible nucleic acid molecule encoding a second floral meristem identity gene product.

The invention also provides a transgenic angiosperm containing a first exogenous ectopically expressible nucleic acid molecule encoding a first floral meristem identity gene product and a second exogenous gene promoter that regulates a second ectopically expressible nucleic acid molecule encoding a second floral meristem identity gene product, provided that the first nucleic acid molecule is not ectopically expressed due to a mutation in an endogenous TERMINAL FLOWER gene.

The invention also provides a transgenic angiosperm containing a first exogenous ectopically expressible nucleic acid molecule encoding a first floral meristem identity gene product and a second exogenous ectopically expressible nucleic acid molecule encoding a second floral meristem identity gene product, where the first floral meristem identity gene product is different from the second floral meristem identity gene product and provided that neither nucleic acid molecule is ectopically expressed due to a mutation in an endogenous TERMINAL FLOWER gene.

The ectopic expression of first and second floral meristem identity gene products can be particularly useful. For example, ectopic expression of AP1 and LFY in a plant promotes flowering earlier than ectopic expression of AP1 alone or ectopic expression of LFY alone. Thus, plant breeding, for example, can be further accelerated, if desired.

First and second floral meristem identity gene products can be, for example, AP1 and CAL, or can be AP1 and LFY or can be CAL and LFY. It should be recognized that where a transgenic angiosperm of the invention contains two exogenous nucleic acid molecules, the order of introducing such a first and a second nucleic acid molecule is not important for purposes of the present invention. Thus, a transgenic angiosperm of the invention having, for example, AP1 as the first floral meristem identity gene product and CAL as the second floral meristem identity gene product is equivalent to a transgenic angiosperm having CAL as the first floral meristem identity gene product and AP1 as the second floral meristem identity gene product.

The invention also provides methods of converting shoot meristem to floral meristem in an angiosperm by ectopically expressing an ectopically expressible nucleic acid molecule encoding a floral meristem identity gene product in the angiosperm. Thus, the invention provides, for example, methods of converting shoot meristem to floral meristem in an angiosperm by introducing an exogenous ectopically expressible nucleic acid molecule encoding a floral meristem identity gene product into the angiosperm, thereby producing a transgenic angiosperm. A floral meristem identity gene product such as AP1, CAL or LFY, or a chimeric protein containing, in part, a floral meristem identity gene product (see below) is useful in the methods of the invention.

As used herein, the term "introducing," when used in reference to an angiosperm, means transferring an exogenous nucleic acid molecule into the angiosperm. For example, an exogenous nucleic acid molecule can be introduced into an angiosperm by methods such as Agrobacterium-mediated transformation or direct gene transfer methods including microprojectile-mediated transformation (Klein et al., Nature 327:70–73 (1987), which is incorporated herein by reference). These and other methods of introducing a nucleic acid molecule into an angiosperm are well known in the art (Bowman et al. (ed.), *Arabidopsis: An Atlas of Morphology and Development*, New York: Springer (1994); Valvekens et al., Proc. Natl. Acad. Sci., USA 85:5536–5540 (1988); and Wang et al., *Transformation of Plants and Soil Microorganisms*, Cambridge, UK: University Press (1995), each of which is incorporated herein by reference).

As used herein, the term "converting shoot meristem to floral meristem" means promoting the formation of flower progenitor tissue where shoot progenitor tissue would normally be formed. As a result of the conversion of shoot meristem to floral meristem, flowers form in an angiosperm where shoots normally would form. The conversion of shoot meristem to floral meristem can be identified using well known methods, such as scanning electron microscopy, light microscopy or visual inspection.

The invention also provides methods of converting shoot meristem to floral meristem in an angiosperm by introducing a first ectopically expressible nucleic acid molecule encoding a first floral meristem identity gene product and a second ectopically expressible nucleic acid molecule encoding a second floral meristem identity gene product into the angiosperm. As discussed above, first and second floral meristem identity gene products useful in the invention can be, for example, AP1 and CAL or AP1 and LFY or CAL and LFY.

The invention also provides methods of promoting early flowering in an angiosperm by ectopically expressing a nucleic acid molecule encoding a floral meristem identity gene product in the angiosperm, provided that the nucleic acid molecule is not ectopically expressed due to a mutation in an endogenous TERMINAL FLOWER gene. For example, the invention provides methods of promoting early flowering in an angiosperm by introducing an ectopically expressible nucleic acid molecule encoding a floral meristem identity gene product into the angiosperm, thus producing a transgenic angiosperm. A floral meristem identity gene product such as AP1, CAL or LFY, or a chimeric protein containing, in part, a floral meristem identity gene product (see below) is useful in methods of promoting early flowering.

The present invention further provides nucleic acid molecules encoding floral meristem identity gene products. For example, the invention provides a nucleic acid molecule encoding CAL, having at least about 70 percent amino acid identity with amino acids 1 to 160 of SEQ ID NO: 10 or SEQ ID NO: 11. The invention also provides a nucleic acid molecule encoding *Arabidopsis thaliana* CAL having the amino acid sequence shown in FIGS. 5A and 5B (SEQ ID NO: 10) and a nucleic acid molecule encoding *Brassica oleracea* CAL having the amino acid sequence shown in FIGS. 6A and 6B (SEQ ID NO: 12). In addition, the invention provides a nucleic acid molecule encoding *Brassica oleracea* AP1 having the amino acid sequence shown in FIGS. 2A and 2B (SEQ ID NO: 4) and a nucleic acid molecule encoding *Brassica oleracea* var. *botrytis* AP1 having the amino acid sequence shown in FIGS. 3A and 3B (SEQ ID NO: 6). The invention also provides a nucleic acid molecule encoding *Zea mays* AP1 having the amino acid sequence shown in FIGS. 4A and 4B (SEQ ID NO: 8).

As disclosed herein, CAL is highly conserved among different angiosperms. For example, Arabidopsis CAL (SEQ ID NO: 10) and *Brassica oleracea* CAL (SEQ ID NO: 12) share about 80 percent amino acid identity. In the region from amino acid 1 to amino acid 160, Arabidopsis CAL and *Brassica oleracea* CAL are about 89 percent identical at the amino acid level. Using a nucleotide sequence derived from a conserved region of SEQ ID NO: 9 or SEQ ID NO: 11, a nucleic acid molecule encoding a novel CAL ortholog can be isolated from other angiosperms. Using methods such as those described by Purugganan et al. (*Genetics* 40: 345–356 (1995)), one can readily confirm that the newly isolated molecule is a CAL ortholog. Thus, a nucleic acid molecule encoding CAL, which has at least about 70 percent amino acid identity with Arabidopsis CAL (SEQ ID NO: 10) or *Brassica oleracea* CAL (SEQ ID NO: 12), can be isolated and identified using well known methods.

The invention also provides a nucleic acid molecule encoding a truncated CAL gene product. For example, the invention provides a nucleic acid molecule encoding the *Brassica oleracea* var. *botrytis* CAL gene product (BobCAL). BobCAL contains 150 amino acids of the approximately 255 amino acids encoded by a full-length CAL cDNA (see FIG. 7; SEQ ID NO: 14; see, also, FIG. 8B).

The invention also provides a nucleic acid containing the *Arabidopsis thaliana* AP1 gene (FIGS. 10A to 10F; SEQ ID NO: 17), a nucleic acid molecule containing the *Brassica oleracea* AP1 gene (FIGS. 11A to 11C; SEQ ID NO: 18) and a nucleic acid molecule containing the *Brassica oleracea* var. *botrytis* AP1 gene (FIGS. 12A to 12C; SEQ ID NO: 19). In addition, the invention also provides a nucleic acid containing the *Arabidopsis thaliana* CAL gene (FIGS. 13A to 13G; SEQ ID NO: 20) and a nucleic acid molecule containing the *Brassica oleracea* CAL gene (FIGS. 11A to 11C; SEQ ID NO: 21). In addition, the invention provides a nucleic acid molecule containing the *Brassica oleracea* var. *botrytis* CAL gene (FIG. 15; SEQ ID NO: 22).

The invention further provides a nucleotide sequence that hybridizes under relatively stringent conditions to a nucleic acid molecule encoding a CAL, or a complementary sequence thereof. In particular, such a nucleotide sequence can hybridize under relatively stringent conditions to a nucleic acid molecule encoding Arabidopsis CAL (SEQ ID NO: 9) or *Brassica oleracea* CAL (SEQ ID NO: 11), or a complementary sequence thereof. Similarly, the present invention provides a nucleotide sequence that hybridizes under relatively stringent conditions to a nucleic acid molecule encoding *Zea mays* AP1 (SEQ ID NO: 7), or a complementary sequence thereof.

In general, a nucleotide sequence that hybridizes under relatively stringent conditions to a nucleic acid molecule is a single-stranded nucleic acid sequence that can range in size from about 10 nucleotides to the full-length of a gene or a cDNA. Such a nucleotide sequence can be chemically synthesized, using routine methods or can be purchased from a commercial source. In addition, such nucleotide sequences can be obtained by enzymatic methods such as random priming methods, the polymerase chain reaction (PCR) or by standard restriction endonuclease digestion, followed by denaturation (Sambrook et al., supra, 1989).

A nucleotide sequence that hybridizes under relatively stringent conditions to a nucleic acid molecule can be used, for example, as a primer for PCR (Innis et al. (ed.) *PCR Protocols: A Guide to Methods and Applications*, San Diego, Calif.: Academic Press, Inc. (1990)). Such a nucleotide sequence generally contains about 10 to about 50 nucleotides.

A nucleotide sequence that hybridizes under relatively stringent conditions to a nucleic acid molecule also can be used to screen a cDNA or genomic library to obtain a related nucleotide sequence. For example, a cDNA library that is prepared from rice or wheat can be screened with a nucleotide sequence derived from the *Zea mays* AP1 sequence in order to isolate a rice or wheat ortholog of AP1. Generally, such a nucleotide sequence contains at least about 14–16 nucleotides depending, for example, on the hybridization conditions to be used.

A nucleotide sequence derived from a nucleic acid molecule encoding *Zea mays* AP1 (SEQ ID NO: 7) also can be used to screen a *Zea mays* cDNA library to isolate a sequence that is related to but distinct from AP1. Furthermore, such a hybridizing nucleotide sequence can be used to analyze RNA levels or patterns of expression, as by northern blotting or by in situ hybridization to a tissue section. Such a nucleotide sequence also can be used in Southern blot analysis to evaluate gene structure and identify the presence of related gene sequences.

One skilled in the art would select a particular nucleotide sequence that hybridizes under relatively stringent conditions to a nucleic acid molecule encoding a floral meristem identity gene product based on the application for which the sequence will be used. For example, in order to isolate an ortholog of AP1, one can choose a region of AP1 that is highly conserved among known AP1 sequences such as Arabidopsis AP1 (SEQ ID NO: 1) and *Zea mays* AP1 (GenBank accession number L46400; SEQ ID NO: 7). Similarly, in order to isolate an ortholog of CAL, one can choose a region of CAL that is highly conserved among known CAL cDNAs, such as Arabidopsis CAL (SEQ ID NO: 9) and Brassica CAL (SEQ ID NO: 11). It further would be recognized, for example, that the region encoding the MADS domain, which is common to a number of genes, can be excluded from the nucleotide sequence. In addition, one can use a full-length Arabidopsis AP1 or CAL cDNA nucleotide sequence (SEQ ID NO: 1 or SEQ ID NO: 9) to isolate an ortholog of AP1 or CAL.

For example, the Arabidopsis AP1 cDNA shown in FIGS. 1A and 1B (SEQ ID NO: 1) can be used as a probe to identify and isolate a novel AP1 ortholog. Similarly, the Arabidopsis CAL cDNA shown in FIGS. 5A and 5B (SEQ ID NO: 9) can be used to identify and isolate a novel CAL ortholog (see Examples IA and IIIC, respectively). In order to identify related MADS domain genes, a nucleotide sequence derived from the MADS domain of AP1 or CAL, for example, also can be useful to isolate a related gene sequence encoding this DNA-binding motif.

Hybridization utilizing a nucleotide sequence of the invention requires that hybridization be performed under relatively stringent conditions such that non-specific hybridization is minimized. Appropriate hybridization conditions can be determined empirically, or can be estimated based, for example, on the relative G+C content of the probe and the number of mismatches between the probe and target sequence, if known. Hybridization conditions can be adjusted as desired by varying, for example, the temperature of hybridizing or the salt concentration (Sambrook, supra, 1989).

The invention also provides a vector containing a nucleic acid molecule encoding a CAL gene product. In addition, the invention provides a vector containing a nucleic acid molecule encoding the *Zea mays* AP1 gene product. A vector can be a cloning vector or an expression vector and provides a means to transfer an exogenous nucleic acid molecule into a host cell, which can be a prokaryotic or eukaryotic cell. Such vectors are well known and include plasmids, phage vectors and viral vectors. Various vectors and methods for introducing such vectors into a cell are described, for example, by Sambrook et al., supra, 1989, and by Glick and Thompson (eds.), *Methods in Plant Molecular Biology and Biotechnology*, Boca Raton, Fla.: CRC Press (1993), which is incorporated herein by reference.

The invention also provides an expression vector containing a nucleic acid molecule encoding a floral meristem identity gene product such as CAL, AP1 or LFY. Expression vectors are well known in the art and provide a means to transfer and express an exogenous nucleic acid molecule into a host cell. Thus, an expression vector contains, for example, transcription start and stop sites such as a TATA sequence and a poly-A signal sequence, as well as a translation start site such as a ribosome binding site and a stop codon, if not present in the coding sequence.

An expression vector can contain, for example, a constitutive regulatory element useful for promoting expression of an exogenous nucleic acid molecule in a plant cell. The use of a constitutive regulatory element can be particularly advantageous because expression from the element is relatively independent of developmentally regulated or tissue-specific factors. For example, the cauliflower mosaic virus 35S promoter (CaMV35S) is a well-characterized constitutive regulatory element that produces a high level of expression in all plant tissues (Odell et al., *Nature* 313:810–812 (1985), which is incorporated herein by reference). The CaMV35S promoter is particularly useful because it is active in numerous different angiosperms (Benfey and Chua, *Science* 250:959–966 (1990), which is incorporated herein by reference; Odell et al., supra, 1985). Other constitutive regulatory elements useful for expression in an angiosperm include, for example, the nopaline synthase (nos) gene promoter (An, *Plant Physiol.* 81:86 (1986), which is herein incorporated by reference).

In addition, an expression vector of the invention can contain a regulated gene regulatory element such as a promoter or enhancer element. A particularly useful regulated promoter is a tissue-specific promoter such as the shoot meristem-specific CDC2 promoter (Hemerly et al., *Plant Cell* 5:1711–1723 (1993), which is incorporated herein by reference), or the AGL8 promoter, which is active in the apical shoot meristem immediately after the transition to flowering (Mandel and Yanofsky, *Plant Cell* 7:1763–1771 (1995), which is incorporated herein by reference).

An expression vector of the invention also can contain an inducible regulatory element, which has conditional activity dependent upon the presence of a particular regulatory factor. Useful inducible regulatory elements include, for example, a heat-shock promoter (Ainley and Key, *Plant Mol. Biol.* 14:949 (1990), which is herein incorporated by reference) or a nitrate-inducible promoter derived from the spinach nitrite reductase gene (Back et al., *Plant Mol. Biol.* 17:9 (1991), which is herein incorporated by reference). A hormone-inducible element (Yamaguchi-Shinozaki et al., *Plant Mol. Biol.* 15:905 (1990) and Kares et al., *Plant Mol. Biol.* 15:225 (1990), which are herein incorporated by reference) or a light-inducible promoter, such as that associated with the small subunit of RUBP carboxylase or the LHCP gene families (Feinbaum et al., *Mol. Gen. Genet.* 226:449 (1991) and Lam and Chua, *Science* 248:471 (1990), which are herein incorporated by reference) also can be useful in an expression vector of the invention. A human glucocorticoid response element also can be used to achieve steroid hormone-dependent gene expression in plants (Schena et al., *Proc. Natl. Acad. Sci. USA* 88:10421 (1991), which is herein incorporated by reference).

An appropriate gene regulatory element such as a promotor is selected depending on the desired pattern or level of expression of a nucleic acid molecule linked thereto. For example, a constitutive promoter, which is active in all tissues, would be appropriate to express a desired gene product in all cells containing the vector. In addition, it can be desirable to restrict expression of a nucleic acid molecule to a particular tissue or during a particular stage of development. A developmentally regulated or tissue-specific expression can be useful for this purpose and can avoid potential undesirable side-effects that can accompany unregulated expression. Inducible expression also can be particularly useful to manipulate the timing of gene expression such that, for example, a population of transgenic angiosperms of the invention that contain an expression vector comprising a floral meristem identity gene linked to an inducible promoter can be induced to flower essentially at the same time. Such timing of flowering can be useful, for example, for manipulating the time of crop harvest.

The invention also provides a kit containing an expression vector having a nucleic acid molecule encoding a floral meristem identity gene product. Such a kit is useful for converting shoot meristem to floral meristem in an angiosperm or for promoting early flowering in an angiosperm. If desired, such a kit can contain appropriate reagents, which can allow relatively high efficiency of transformation of an angiosperm with the vector. Furthermore, a control plasmid lacking the floral meristem identity gene can be included in the kit to determine, for example, the efficiency of transformation.

The invention further provides a host cell containing a vector comprising a nucleic acid molecule encoding CAL. A host cell can be prokaryotic or eukaryotic and can be, for example, a bacterial cell, yeast cell, insect cell, xenopus cell, mammalian cell or plant cell.

The invention also provides a transgenic garden variety cauliflower plant containing an exogenous nucleic acid molecule selected from the group consisting of a nucleic acid molecule encoding a CAL gene product and a nucleic acid molecule encoding an AP1 gene product. Such a transgenic cauliflower plant can produce an edible flower in place of the typical cauliflower vegetable.

A nucleic acid encoding CAL has been isolated from a *Brassica oleracea* line that produces wild-type flowers (BoCAL) and from the common garden variety of cauliflower, *Brassica oleracea* var. *botrytis* (BobCAL), which lacks flowers. The *Brassica oleracea* CAL cDNA (SEQ ID NO: 10) is highly similar to the Arabidopsis CAL cDNA (SEQ ID NO: 12; and see FIGS. 8A and 8B). In contrast, the *Brassica oleracea* var. *botrytis* CAL cDNA contains a stop codon, predicting that the BobCAL protein will be truncated after amino acid 150 (SEQ ID NO: 14 and see FIGS. 8A and 8B). The correlation of full-length Arabidopsis and *Brassica oleracea* CAL gene products with a flowering phenotype indicates that transformation of non-flowering garden varieties of cauliflower such as *Brassica oleracea* var. *botrytis* with a full-length CAL cDNA can induce flowering in the transgenic cauliflower plant.

As used herein, the term "CAL gene product" means a full-length CAL gene product that does not terminate substantially before amino acid 255 and that, when ectopically expressed in shoot meristem, converts shoot meristem to floral meristem. A nucleic acid molecule encoding a CAULIFLOWER gene product can be, for example, a nucleic acid molecule encoding Arabidopsis CAL shown in FIG. 5 (SEQ ID NO: 9) or a nucleic acid molecule encoding *Brassica oleracea* CAL shown in FIGS. 6A and 6B (SEQ ID NO: 11). In comparison, a nucleic acid molecule encoding a truncated CAL gene product that terminates substantially before amino acid 255, such as the encoded truncated BobCAL gene product (SEQ ID NO: 13), is not a nucleic acid molecule encoding a CAL gene product as defined herein. Furthermore, ectopic expression of BobCAL in an angiosperm does not result in conversion of shoot meristem to floral meristem.

As used herein, the term "AP1 gene product" means a full-length AP1 gene product that does not terminate substantially before amino acid 256. A nucleic acid molecule encoding an AP1 gene product can be, for example, a nucleic acid molecule encoding Arabidopsis AP1 shown in FIGS. 1A and 1B (SEQ ID NO: 1), *Brassica oleracea* AP1 shown in FIGS. 2A and 2B , (SEQ ID NO: 3), *Brassica oleracea* var. *botrytis* AP1 shown in FIGS. 3A and 3B (SEQ ID NO: 5) or *Zea mays* AP1 shown in FIGS. 4A and 4B (SEQ ID NO: 7).

The invention provides a CAL polypeptide having at least about 70 percent amino acid identity with amino acids 1 to 160 of SEQ ID NO: 10 or SEQ ID NO: 12. For example, the *Arabidopsis thaliana* CAL polypeptide, having the amino acid sequence shown as amino acids 1 to 255 in FIGS. 5A and 5B (SEQ ID NO: 10), and the *Brassica oleracea* CAL polypeptide, having the amino acid sequence shown as amino acids 1 to 255 in FIGS. 6A and 6B (SEQ ID NO: 12) are provided by the invention.

The invention also provides the truncated *Brassica oleracea* var. *botrytis* CAL polypeptide having the amino acid sequence shown as amino acids 1 to 150 in FIG. 7 (SEQ ID NO: 14). The BobCAL polypeptide can be useful as an immunogen to produce an antibody that specifically binds the truncated BoCAL polypeptide, but does not bind a full length CAL gene product. Such an antibody can be useful to distinguish between a full length CAL and truncated CAL.

The invention provides also provides a *Zea mays* AP1 polypeptide. As used herein, the term "polypeptide" is used in its broadest sense to include proteins, polypeptides and peptides, which are related in that each consists of a sequence of amino acids joined by peptide bonds. For convenience, the terms "polypeptide," "protein" and "gene product" are used interchangeably. While no specific attempt is made to distinguish the size limitations of a protein and a peptide, one skilled in the art would understand that proteins generally consist of at least about 50 to 100 amino acids and that peptides generally consist of at least two amino acids up to a few dozen amino acids. The term polypeptide is used generally herein to include any such amino acid sequence.

The term polypeptide also includes an active fragment of a floral meristem identity gene product. As used herein, the term "active fragment," means a polypeptide portion of a floral meristem identity gene product that can convert shoot meristem to floral meristem or can provide early flowering. For example, an active fragment of a CAL polypeptide can consist of an amino acid sequence derived from a CAL protein as shown in FIGS. 5A and 5B or 6A and 6B (SEQ ID NOS: 10 and 12) and that has an activity of a CAL. An active fragment can be, for example, an amino terminal or carboxyl terminal truncated form of *Arabidopsis thaliana* CAL or *Brassica oleracea* CAL (SEQ ID NOS: 10 or 12, respectively). Such an active fragment can be produced using well known recombinant DNA methods (Sambrook et al., supra, 1989). The product of the BobCAL gene, which is truncated at amino acid 150, lacks activity in converting shoot meristem to floral meristem and, therefore, is an example of a polypeptide portion of a CAL floral meristem identity gene product that is not an "active fragment."

An active fragment of a floral meristem identity gene product can convert shoot meristem to floral meristem and is readily identified using the methods described in Example II, below). Briefly, Arabidopsis can be transformed with a nucleic acid molecule encoding a portion of a floral meristem identity gene product, in order to determine whether the fragment can convert shoot meristem to floral meristem or promote early flowering and, therefore, has an activity of a floral meristem identity gene product.

The invention further provides an antibody that specifically binds a CAL polypeptide, an antibody that specifically binds the truncated *Brassica oleracea* var. *botrytis* CAL polypeptide, and an antibody that specifically binds the *Zea mays* AP1 polypeptide. As used herein, the term "antibody" is used in its broadest sense to include polyclonal and monoclonal antibodies, as well as polypeptide fragments of antibodies that retain a specific binding activity for CAL protein of at least about $1 \times 10^5$ $M^{-1}$. One skilled in the art would know that anti-CAL antibody fragments such as Fab, F(ab')$_2$ and Fv fragments can retain specific binding activity for CAL and, thus, are included within the definition of an antibody. In addition, the term "antibody" as used herein includes naturally occurring antibodies as well as non-naturally occurring antibodies and fragments that have binding activity such as chimeric antibodies or humanized antibodies. Such non-naturally occurring antibodies can be constructed using solid phase peptide synthesis, produced recombinantly or obtained, for example, by screening combinatorial libraries consisting of variable heavy chains and variable light chains as described by Huse et al., *Science* 246:1275–1281 (1989), which is incorporated herein by reference.

An antibody "specific for" a polypeptide, or that "specifically binds" a polypeptide, binds with substantially higher affinity to that polypeptide than to an unrelated polypeptide. An antibody specific for a polypeptide also can have specificity for a related polypeptide. For example, an antibody specific for Arabidopsis CAL also can have specificity for *Brassica oleracea* CAL.

An anti-CAL antibody, for example, can be prepared using a CAL fusion protein or a synthetic peptide encoding a portion of Arabidopsis CAL or of *Brassica oleracea* CAL as an immunogen. One skilled in the art would know that purified CAL protein, which can be prepared from natural sources or produced recombinantly, or fragments of CAL, including a peptide portion of CAL such as a synthetic peptide, can be used as an immunogen. Non-immunogenic fragments or synthetic peptides of CAL can be made immunogenic by coupling the hapten to a carrier molecule such as bovine serum albumin (BSA) or keyhole limpet hemocyanin (KLH). In addition, various other carrier molecules and methods for coupling a hapten to a carrier molecule are well known in the art and described, for example, by Harlow and Lane, *Antibodies: A laboratory manual* (Cold Spring Harbor Laboratory Press, 1988), which is incorporated herein by reference. An antibody that specifically binds the truncated Bob CAL polypeptide or an antibody that specifically binds the *Zea mays* AP1 polypeptide similarly can be produced using such methods. An antibody that specifically binds the truncated *Brassica oleracea* var. *botrytis* CAL polypeptide can be particularly useful to distinguish between full-length CAL polypeptide and truncated CAL polypeptide.

The invention provides a method of identifying a Brassica having a modified CAL allele by detecting a polymorphism associated with a CAL locus, where the CAL locus comprises a modified CAL allele that does not encode an active CAL gene product. Such a method is useful for the genetic improvement of Brassica plants, a genus of great economic value.

Brassica plants are a highly diverse group of crop plants useful as vegetables and as sources of condiment mustard, edible and industrial oil, animal fodder and green manure. Brassica crops encompass a variety of well known vegetables including cabbage, cauliflower, broccoli, collard, kale, mustard greens, Chinese cabbage and turnip, which can be interbred for crop improvement (see, for example, King, *Euphytica* 50:97–112 (1990) and Crisp and Tapsell, *Genetic improvement of vegetable crops* pp. 157–178 (1993), each of which is herein incorporated by reference).

Breeding of Brassica crops is useful, for example, for improving the quality and early development of vegetables. In addition, such breeding can be useful to increase disease resistance, such as resistance, of a Brassica to clubroot disease or mildew; viral resistance, such as resistance to turnip mosaic virus and cauliflower mosaic virus; or pest resistance (King, supra, 1990).

The use of polymorphic molecular markers in the breeding of Brassicae is well recognized in the art (Crisp and Tapsell, supra, 1993). Identification of a polymorphic molecular marker that is associated with a desirable trait can vastly accelerate the time required to breed the desirable trait into a new Brassica species or variant. In particular, since many rounds of backcrossing are required to breed a new trait into a different genetic background, early detection of a desirable trait by molecular methods can be performed prior to the time a plant is fully mature, thus accelerating the rate of crop breeding (see, for example, Figidore et al., *Euphytica* 69: 33–44 (1993), which is herein incorporated by reference).

A polymorphism associated with a CAL locus comprising a modified CAL allele that does not encode an active CAL gene product, is disclosed herein. FIGS. 6A and 6B shows the nucleotide (SEQ ID NO: 11) and amino acid (SEQ ID NO: 12) sequence of *Brassica oleracea* CAL (BoCAL), and FIG. 7 shows the nucleotide (SEQ ID NO: 13) and amino acid (SEQ ID NO: 14) sequence of *Brassica oleracea* var. *botrytis* CAL (BobCAL). At amino acid 150, which is glutamic acid (Glu) in BoCAL, a stop codon is present in BobCAL. This polymorphism results in a truncated Bob-CAL gene product that is not active as a floral meristem identity gene product. The BoCAL nucleic acid sequence (ACGAGT) can be readily distinguished from the BobCAL nucleic acid sequence (ACTAGT) using well known molecular methods. For example, the polymorphic ACT-AGT BobCAL sequence is recognized by a SpeI restriction endonuclease site, whereas the ACGAGT BoCAL sequence is not recognized by SpeI. Thus, a restriction fragment length polymorphism (RFLP) in BobCAL provides a simple means for identifying a modified CAL allele (BobCAL) and, therefore, can serve as a marker to predict the inheritance of the "cauliflower" phenotype.

A modified CAL allele encoding a truncated CAL gene product also can serve as a marker to predict the "cauliflower" phenotype in other cauliflower variants. For example, nine romanesco variants of Brassica oleracea var. botrytis, which each have the "cauliflower" phenotype, were examined for the presence of a stop codon at position 151 of the CAL coding sequence. All nine of the romanesco variants contained the SpeI site that indicates a stop codon and, thus, a truncated CAL gene product. In contrast, Brassica oleracea variants that lack the "cauliflower" phenotype (broccoli and brussels sprouts) were examined for the SpeI site. In every case, the broccoli and brussel sprout variants had a full-length CAL coding sequence, as indicated by the absence of the distinguishing SpeI site. Thus, a truncated CAL gene product can be involved in the "cauliflower phenotype" in numerous different Brassica variants.

As used herein, the term "modified CAL allele" means a CAL allele that does not encode a CAL gene product active in converting shoot meristem to floral meristem. A modified CAL allele can have a modification within a gene regulatory element such that a CAL gene product is not produced. In addition, a modified CAL allele can have a modification such as a mutation, deletion or insertion in a CAL coding sequence which results in an inactive CAL gene product. For example, an inactive CAL gene product can result from a mutation creating a stop codon, such that a truncated, inactive CAL gene product lacking the ability to convert shoot meristem to floral meristem is produced.

As used herein, the term "associated" means closely linked and describes the tendency of two genetic loci to be inherited together as a result of their proximity. If two genetic loci are associated and are polymorphic, one locus can serve as a marker for the inheritance of the second locus. Thus, a polymorphism associated with a CAL locus comprising a modified CAL allele can serve as a marker for inheritance of the modified CAL allele. An associated polymorphism can be located in proximity to a CAL gene or can be located within a CAL gene.

A polymorphism in a nucleic acid sequence can be detected by a variety of methods. For example, if the polymorphism occurs in a particular restriction endonuclease site, the polymorphism can be detected by a difference in restriction fragment length observed following restriction with the particular restriction endonuclease and hybridization with a nucleotide sequence that is complementary to a nucleic acid sequence including a polymorphism.

The use of restriction fragment length polymorphism as an aid to breeding Brassicae is well known in the art (see, for example, Slocum et al., Theor. Appl. Genet. 80:57–64 (1990); Kennard et al., Theor. Appl. Genet. 87:721–732 (1994); and Figidore et al., supra, 1993, each of which is herein incorporated by reference). A restriction endonuclease such as SpeI, which is useful for identifying the presence of a BobCAL allele in an angiosperm, is readily available and can be purchased from a commercial source. Furthermore, a nucleotide sequence that is complementary to a nucleic acid sequence having a polymorphism associated with a CAL locus comprising a modified CAL allele can be derived, for example, from the nucleic acid molecule encoding Brassica oleracea var. botrytis CAL shown in FIG. 7 (SEQ ID NO: 13) or from the nucleic acid molecule encoding Brassica oleracea CAL shown in FIGS. 6A and 6B (SEQ ID NO: 11).

In some cases, a polymorphism is not distinguishable by a RFLP, but nevertheless can be used to identify a Brassica having a modified CAL allele. For example, the polymerase chain reaction (PCR) can be used to detect a polymorphism associated with a CAL locus comprising a modified CAL allele. Specifically, a polymorphic region of a modified allele can be selectively amplified by using a primer that matches the nucleotide sequence of one allele of a polymorphic locus, but does not match the sequence of the second allele (Sobral and Honeycutt, The Polymerase Chain Reaction, pp. 304–319 (1994), which is herein incorporated by reference). Other well-known approaches for analyzing a polymorphism using PCR include discriminant hybridization of PCR-amplified DNA to allele-specific oligonucleotides and denaturing gradient gel electrophoresis (see Innis et al., supra, 1990).

The invention further provides a nucleic acid molecule encoding a chimeric protein, comprising a nucleic acid molecule encoding a floral meristem identity gene product such as AP1, LFY or CAL operably linked to a nucleic acid molecule encoding a ligand binding domain. Expression of a chimeric protein of the invention in an angiosperm is particularly useful because the ligand binding domain confers regulatable activity on a gene product such as a floral meristem identity gene product to which it is fused. Specifically, the floral meristem identity gene product component of the chimeric protein is inactive in the absence of the particular ligand, whereas, in the presence of ligand, the ligand binds the ligand binding domain, resulting in floral meristem identity gene product activity.

A nucleic acid molecule encoding a chimeric protein of the invention contains a nucleic acid molecule encoding a floral meristem identity gene product, such as a nucleic acid molecule encoding the amino acid sequence shown in FIGS. 1A and 1B (SEQ ID NO: 2), in FIGS. 5A and 5B (SEQ ID NO: 10), or in FIGS. 9A and 9B (SEQ ID NO: 10), either of which is operably linked to a nucleic acid molecule encoding a ligand binding domain. The expression of such a nucleic acid molecule results in the production of a chimeric protein comprising a floral meristem identity gene product fused to a ligand binding domain. Thus, the invention also provides a chimeric protein comprising a floral meristem identity gene product fused to a ligand binding domain.

A ligand binding domain useful in a chimeric protein of the invention can be a steroid binding domain such as the ligand binding domain of a glucocorticoid receptor, estrogen receptor, progesterone receptor, androgen receptor, thyroid receptor, vitamin D receptor or retinoic acid receptor. A particularly useful ligand binding domain is a glucocorticoid receptor ligand binding domain, encompassed, for example, within amino acids 512 to 795 of the rat glucocorticoid receptor as shown in FIG. 16 (SEQ ID NO: 24; Miesfeld et al., Cell 46:389–399 (1986), which is incorporated herein by reference).

A chimeric protein containing a ligand binding domain, such as the rat glucocorticoid receptor ligand binding domain, confers glucocorticoid-dependent activity on the chimeric protein. For example, the activity of chimeric proteins consisting of adenovirus E1A, c-myc, c-fos, the HIV-1 Rev transactivator, MyoD or maize regulatory factor R fused to the rat glucocorticoid receptor ligand binding domain is regulated by glucocorticoid hormone (Eilers et al., Nature 340:66 (1989); Superti-Furga et al., Proc. Natl. Acad. Sci., U.S.A. 88:5114 (1991); Hope et al., Proc. Natl. Acad. Sci,. U.S.A. 87:7787 (1990); Hollenberg et al., Proc. Natl. Acad. Sci., U.S.A. 90:8028 (1993), each of which is incorporated herein by reference).

Such a chimeric protein also can be regulated in plants. For example, a chimeric protein containing a heterologous protein fused to a rat glucocorticoid receptor ligand binding domain (amino acids 512 to 795) was expressed under the control of the constitutive cauliflower mosaic virus 35S promoter in Arabidopsis. The activity of the chimeric protein was inducible; the chimeric protein was inactive in the absence of ligand, and became active upon treatment of transformed plants with a synthetic glucocorticoid, dexamethasone (Lloyd et al., Science 266:436–439 (1994), which is incorporated herein by reference). As disclosed herein, a ligand binding domain fused to a floral meristem identity gene product can confer ligand inducibility on the activity of a fused floral meristem identity gene product in plants such that, upon exposure to a particular ligand, the floral meristem identity gene product is active.

Methods for constructing a nucleic acid molecule encoding a chimeric protein are routine and well known in the art (Sambrook et al., supra, 1989). For example, the skilled artisan would recognize that a stop codon in the 5' nucleic acid molecule must be removed and that the two nucleic acid molecules must be linked such that the reading frame of the 3' nucleic acid molecule is preserved. Methods of transforming plants with nucleic acid molecules also are well known in the art (see, for example, Mohoney et al., U.S. Pat. No. 5,463,174, and Barry et al., U.S. Pat. No. 5,463,175, each of which is incorporated herein by reference).

As used herein, the term "operably linked," when used in reference to two nucleic acid molecules comprising a nucleic acid molecule encoding a chimeric protein, means that the two nucleic acid molecules are linked in frame such that a full-length chimeric protein can be expressed. In particular, the 5' nucleic acid molecule, which encodes the amino-terminal portion of the chimeric protein, must be linked to the 3' nucleic acid molecule, which encodes the carboxyl-terminal portion of the chimeric protein, such that the carboxyl-terminal portion of the chimeric protein is produced in the correct reading frame.

The invention further provides a transgenic angiosperm containing a nucleic acid molecule encoding a chimeric protein, comprising a nucleic acid molecule encoding a floral meristem identity gene product such as AP1, CAL or LFY linked to a nucleic acid molecule encoding a ligand binding domain. Such a transgenic angiosperm is particularly useful because the angiosperm can be induced to flower by contacting the angiosperm with a ligand that binds the ligand binding domain. Thus, the invention provides a method of promoting early flowering or of converting shoot meristem to floral meristem in a transgenic angiosperm containing a nucleic acid molecule encoding a chimeric protein of the invention, comprising expressing the nucleic acid molecule encoding the chimeric protein in the angiosperm, and contacting the angiosperm with a ligand that binds the ligand binding domain, wherein binding of the ligand to the ligand binding domain activates the floral meristem identity gene product. In particular, the invention provides methods of promoting early flowering or of converting shoot meristem to floral meristem in a transgenic angiosperm containing a nucleic acid molecule encoding a chimeric protein that consists of a nucleic acid molecule encoding AP1 or CAL or LFY linked to a nucleic acid molecule encoding a glucocorticoid receptor ligand binding domain by contacting the transgenic angiosperm with a glucocorticoid such as dexamethasone.

As used herein, the term "ligand" means a naturally occurring or synthetic chemical or biological molecule such as a simple or complex organic molecule, a peptide, a protein or an oligonucleotide that specifically binds a ligand binding domain. A ligand of the invention can be used, alone, in solution or can be used in conjunction with an acceptable carrier that can serve to stabilize the ligand or promote absorption of the ligand by an angiosperm.

One skilled in the art can readily determine the optimum concentration of ligand needed to bind a ligand binding domain and render a floral meristem identity gene product active. Generally, a concentration of about 1 nM to 1 $\mu$M dexamethasone is useful for activating floral meristem identity gene product activity in a chimeric protein comprising a floral meristem identity gene product and a glucocorticoid receptor ligand binding domain (Lloyd et al., supra, 1994).

A transgenic angiosperm expressing a chimeric protein of the invention can be contacted with ligand in a variety of manners including, for example, by spraying, injecting or immersing the angiosperm. Further, a plant may be contacted with a ligand by adding the ligand to the plant's water supply or to the soil, whereby the ligand is absorbed into the angiosperm.

The following examples are intended to illustrate but not limit the present invention.

EXAMPLE I

Identification and Characterization of the Zea mays APETALA1 cDNA

This example describes the isolation and characterization of the Zea mays ZAP-1 "gene", which is an ortholog of the Arabidopsis floral meristem identity gene, AP1.

A. Identification and Characterization of a Nucleic Acid Sequence Encoding ZAP-1

The utility of using a cloned floral homeotic gene from Arabidopsis to identify the putative ortholog in maize has previously been demonstrated (Schmidt et al., supra, (1993), which is incorporated herein by reference). As described in Mena et al. (Plant J. 8(6):845–854 (1995)), the maize ortholog of the Arabidopsis AP1 floral meristem identity gene, was isolated by screening a Zea mays ear cDNA library using the Arabidopsis AP1 cDNA (SEQ ID NO: 1) as a probe. A cDNA library was prepared from wild-type immature ears as described by Schmidt et al., supra, 1993, using an Arabidopsis AP1 cDNA sequence as a probe. The Arabidopsis AP1 cDNA (SEQ ID NO: 1), which is shown in FIGS. 1A and 1B (SEQ ID NO 1), was used as the probe. Low-stringency hybridizations with the AP1 probe were conducted as described previously for the isolation of ZAG1 using the AG cDNA as a probe (Schmidt et al., supra, 1993). Positive plaques were isolated and cDNAs were recovered in Bluescript by in vivo excision. Double-stranded sequencing was performed using the Sequenase Version 2.0 kit (U.S. Biochemical, Cleveland, Ohio) according to the manufacturer's protocol.

The cDNA sequence and deduced amino acid sequence for ZAP1 are shown in FIGS. 4A and 4B (SEQ ID NOS: 7 and 8). The deduced amino acid sequence for ZAP1 shares 89% identity with Arabidopsis AP1 through the MADS domain (amino acids 1 to 57) and 70% identity through the first 160 amino acids, which includes the K domain. The high level of amino acid sequence identity between ZAP1 and AP1 (SEQ ID NOS: 8 and 2), as well as the expression pattern of ZAP1 in maize florets (see below), indicates that ZAP1 is the maize ortholog of Arabidopsis AP1.

B. RNA Expression Pattern of ZAP1

Total RNA was isolated from different maize tissues as described by Cone et al., *Proc. Natl. Acad. Sci., USA* 83:9631–9635 (1986), which is herein incorporated by reference. RNA was prepared from ears or tassels at early developing stages (approximately 2 cm in size), husk leaves from developing ear shoots, shoots and roots of germinated seedlings, leaves from 2 to 3 week old plants and endosperm, and embryos at 18 days after pollination. Mature floral organs were dissected from ears at the time of silk emergence or from tassels at several days pre-emergence. To study expression patterns in the mature female flower, carpels were isolated and the remaining sterile organs were pooled and analyzed together. In the same way, stamens were dissected and collected from male florets and the remaining organs (excluding the glumes) were pooled as one sample.

RNA concentration and purity was determined by absorbance at 260/280 nM, and equal amounts (10 μg) were fractionated on formaldehyde-agarose gels. Gels were stained in a solution of 0.125 μg ml$^{-1}$ acridine orange to confirm the integrity of the RNA samples and the uniformity of gel loading, then RNA was blotted on to Hybond-N® membranes (Amersham International, Arlington Heights, Ill.) according to the manufacturer's instructions. Prehybridization and hybridization solutions were prepared as previously described (Schmidt et al., *Science* 238:960–963 (1987), which is incorporated herein by reference). The probe for ZAP1 RNA expression studies was a 445 bp SacI-NsiI fragment from the 3' end of the cDNA. Southern blot analyses were conducted to establish conditions for specific hybridization of this probe. No cross-hybridization was detected with hybridization at 60° C. in 50% formamide and washes at 65° C. in 0.1×SSC and 0.5% SDS.

The strong sequence similarity between ZAP1 and AP1 indicated that ZAP1 was the ortholog of this Arabidopsis floral meristem identity gene. As a first approximation of whether the pattern of ZAP1 expression paralleled that of AP1, a blot of total RNA from vegetative and reproductive organs was hybridized with a gene-specific fragment of the ZAP1 cDNA (nucleotides 370 to 820 of SEQ ID NO: 7). ZAP1 RNA was detected only in male and female inflorescences and in the husk leaves that surround the developing ear. No ZAP1 RNA expression was detectable in RNA isolated from root, shoot, leaf, endosperm, or embryo tissue. The restriction of ZAP1 expression to terminal and axillary inflorescences is consistent with ZAP1 being the Arabidopsis AP1 ortholog.

Male and female florets were isolated from mature inflorescences, and the reproductive organs were separated from the remainder of the floret. RNA was isolated from the reproductive and the sterile portions of the florets. ZAP1 RNA expression was not detected in maize stamens or carpels, whereas high levels of ZAP1 RNA were present in developing ear and tassel florets from which the stamens and carpels had been removed. Thus, the exclusion of ZAP1 expression in stamens and carpels and its inclusion in the RNA of the non-reproductive portions of the floret (lodicules, lemma and palea) is similar to the pattern of expression of AP1 in flowers of Arabidopsis.

EXAMPLE II

Conversion of Shoot Meristem to Floral Meristem in an APETALA1 Transgenic Plant

This example describes methods for producing a transgenic Arabidopsis plant, in which shoot meristem is converted to floral meristem.

A. Ectopic Expression of APETALA1 Converts Inflorescence Shoots into Flowers

Transgenic plants that constitutively express AP1 from the cauliflower mosaic virus 35S (CaMV35S) promoter were produced to determine whether ectopic AP1 expression could convert shoot meristem to floral meristem. The AP1 coding sequence was placed under control of the cauliflower mosaic virus 35S promoter (Odell et al., supra, 1985) as follows. BamHI linkers were ligated to the HincII site of the full-length AP1 complementary DNA (Mandel et al., supra, (1992), which is incorporated herein by reference) in pAM116, and the resulting BamHI fragment was fused to the cauliflower mosaic virus 35S promoter (Jack et al., *Cell* 76:703–716 (1994), which is incorporated herein by reference) in pCGN18 to create pAM563.

Transgenic AP1 Arabidopsis plants of the Columbia ecotype were generated by selecting kanamycin-resistant plants after Agrobacterium-mediated plant transformation using the in planta method (Bechtold et al., *C.R. Acad. Sci. Paris* 316:1194–1199 (1993), which is incorporated herein by reference). All analyses were performed in subsequent generations. Approximately 120 independent transgenic lines that displayed the described phenotypes were obtained.

Remarkably, in 35S-AP1 transgenic plants, the normally indeterminate shoot apex) prematurely terminated as a floral meristem and formed a terminal flower. In addition, all lateral meristems that normally would produce inflorescence shoots also were converted into solitary flowers. These results demonstrate that ectopic expression of AP1 in shoot meristem is sufficient to convert shoot meristem to floral meristem, even though AP1 normally is not absolutely required to specify floral meristem identity.

B. LEAFY is not Required for the Conversion of Inflorescence Shoots to Flowers in an APETALA1 Transgenic Plant To determine whether the 35S-AP1 transgene causes ectopic LFY activity, and whether ectopic LFY activity is required for the conversion of shoot meristem to floral meristem, the 35S-AP1 transgene was introduced into Arabidopsis lfy mutants. The 35S-AP1 transgene was crossed into the strong lfy-6 mutant background and the $F_2$ progeny were analyzed.

Lfy mutant plants containing the 35S-AP1 transgene displayed the same conversion of apical and lateral shoot meristem to floral meristem as was observed in transgenics containing wild type LFY. However, the resulting flowers had the typical lfy mutant phenotype, in which floral organs developed as sepaloid and carpelloid structures, with an absence of petals and stamens. These results demonstrate that LFY is not required for the conversion of shoot meristem to floral meristem in a transgenic angiosperm that ectopically expresses AP1.

C. APETALA1 is not Sufficient to Specify Organ Fate

As well as being involved in the early step of specifying floral meristem identity, AP1 also is involved in specifying sepal and petal identity at a later stage in flower development. Although AP1 RNA is initially expressed throughout the young flower primordium, it is later excluded from stamen and carpel primordia (Mandel et al., *Nature* 360:273–277 (1992)). Since the cauliflower mosaic virus 35S promoter is active in all floral organs, 35S-AP1 transgenic plants are likely to ectopically express AP1 in stamens and carpels. However, 35S-AP1 transgenic plants had normal stamens and carpels, indicating that AP1 is not sufficient to specify sepal and petal organ fate.

D. Ectopic Expression of APETALA1 Causes Early Flowering

In addition to its ability to alter inflorescence meristem identity, ectopic expression of AP1 also influences the vegetative phase of plant growth. Wild-type plants have a vegetative phase during which a basal rosette of leaves is produced, followed by the transition to reproductive growth. The transition from vegetative to reproductive growth was measured both in terms of the number of days post-germination until the first visible flowers were observed, and by counting the number of leaves. Under continuous light, wild-type and 35S-AP1 transgenic plants flowered after producing 9.88±1.45 and 4.16±0.97 leaves, respectively. Under short-day growth conditions (8 hours light, 16 hours dark, 24 C), wild-type and 35S-AP1 transgenic plants flowered after producing 52.42±3.47 and 7.4±1.18 leaves, respectively.

In summary, under continuous light growth conditions, flowers appear on wild-type Arabidopsis plants after approximately 18 days, whereas the 35S-AP1 transgenic plants flowered after an average of only 10 days. Furthermore, under short-day growth conditions, flowering is delayed in wild-type plants until approximately 10 weeks after germination, whereas, 35S-AP1 transgenic plants flowered in less than 3 weeks. Thus, ectopic AP1 activity significantly reduced the time to flowering and reduced the delay of flowering caused by short day growth conditions.

EXAMPLE III

Isolation and Characterization of the Arabidopsis and *Brassica oleracea* CAULIFLOWER Genes This example describes methods for isolating and characterizing the Arabidopsis and *Brassica oleracea* CAL genes.

A. Isolation of the Arabidopsis and *Brassica oleracea* CAULIFLOWER Genes

Genetic evidence that CAL and AP1 proteins may be functionally related indicated that these proteins may share similar DNA sequences. In addition, DNA blot hybridization revealed that the Arabidopsis genome contains a gene that is closely related to AP1. The CAL gene, which is closely related to AP1, was isolated and identified as a member of the family of Arabidopsis MADS domain genes known as the AGAMOUS-like (AGL) genes.

Hybridization with an AP1 probe was used to isolate a 4.8-kb Eco RI genomic fragment of CAL. The corresponding CAL complementary DNA (pBS85) was cloned by reverse transcription-polymerase chain reaction (RT-PCR) with the oligonucleotides AGL10-1 (5'-GATCGTCGTTATCTCTCTTG-3'; SEQ ID NO: 25) and AGL10-12 (5'-GTAGTCTATTCAAGCGGCG-3'; SEQ ID NO: 26).

The Arabidopsis CAL cDNA encodes a putative 255 amino acid protein (FIGS. 5A and 5B; SEQ ID NO: 10) having a calculated molecular weight of 30.1 kD and an isoelectric point of 8.78. The deduced amino acid sequence for CAL contains a MADS domain which generally is present in a class of transcription factors. The MADS domains of CAL and AP1 were markedly similar, differing in only 5 of 56 amino acid residues, 4 of which represent conservative replacements. Overall, the putative CAL protein is 76% identical to AP1; with allowance for conservative amino acid substitutions, the two proteins are 88% similar. These results indicate that CAL and AP1 may recognize similar target sequences and regulate many of the same genes involved in floral meristems identity.

CAL was mapped to the approximate location of the loci identified by classical genetic means for the cauliflower phenotype (Bowman et al., *Development* 119:721 (1993), which is herein incorporated by reference). Restriction fragment length polymorphism (RFLP) mapping filters were scored and the results analyzed with the Macintosh version of the Mapmaker program as described by Rieter et al., (*Proc. Natl. Acad. Sci., USA*, 89:1477 (1992), which is herein incorporated by reference). The results localized CAL to the upper arm of chromosome 1, near marker λ235.

A genomic fragment spanning the CAL gene was used to transform cal-1 ap1-1 plants. A 5850-bp Bam HI fragment containing the entire coding region of the Arabidopsis CAL gene as well as 1860 bp upstream of the putative translational start site was inserted into the pBIN19 plant transformation vector (Clontech, Palo Alto, Calif.) and used for transformation of root tissue from cal-1 ap1-1 plants as described by Valvekens et al. (*Proc. Natl. Acad. Sci., USA* 85:5536 (1988), which is incorporated herein by reference). Seeds were harvested from primary transformants, and all phenotypic analyses were performed in subsequent generations. Four independent lines transformed with CAL showed a complementation of the cauliflower (cal) phenotype and displayed a range of phenotypes similar to those exhibited by ap1 mutants. These results demonstrated that CAL functions to convert shoot meristem to floral meristem.

In order to identify regions of functional importance in the CAL protein, cal mutants were generated and analyzed. The cal alleles were isolated by mutagenizing seeds homozygous for the ap1-1 allele in Ler with 0.1% or 0.05% ethylmethane sulfonate (EMS) for 16 hours. Putative new cal alleles were crossed to cal-1 api-1 chlorina plants to verify allelism. Two sets of oligonucleotides were used to amplify and clone new alleles: oligos AGL10-1 (SEQ ID NO: 25) and AGL10-2 (5'-GATGGAGACCATTAAACAT-3; SEQ ID NO: 27) for the 5' portion and oligos AGL10-3 (5'-GGAGAAGGTACTAGAACG-3'; SEQ ID NO: 28) and AGL10-4 (5'-GCCCTCTTCCATAGATCC-3'; SEQ ID NO: 29) for the 3' portion of the gene. All coding regions and intron-exon boundaries of the mutant alleles were sequenced.

Sequence analysis of the cal-1 allele, which exists in the wild-type Wassilewskija (WS) ectoype, revealed a cluster of three amino acid differences in the seventh exon, relative to the wild-type gene product from Landsberg erecta (Ler) (FIGS. 8A and 8B). One or more of these amino acid differences can be responsible for the cal phenotype, because the cal-1 gene was expressed normally and the transcribed RNA was correctly spliced in the WS background. The three additional cal alleles that were isolated, designated cal-2, cal-3, and cal-4, exhibited phenotypes similar to that of the cal-1 allele.

Sequence analyses revealed a single missense mutation for each (FIGS. 8A and 8B). Since mutations in the cal-2 and cal-3 alleles lie in the MADS domain, these mutations can affect the ability of CAL to bind DNA and activate its target genes. Because the cal-4 allele contains a substitution in the K domain, a motif thought to be involved in protein-protein interactions, this mutation can affect the ability of CAL to form homodimers or to interact with other proteins such as AP1.

B. RNA Expression Pattern of CAULIFLOWER

To characterize the temporal and spatial pattern of CAL RNA accumulation, RNA in situ hybridizations were performed using a CAL-specific probe. $^{35}$S-labeled antisense CAL and BoCAL mRNA was synthesized from Sca 1-digested cDNA templates and hybridized to 8 μm sections of Arabidopsis Ler or *Brassica oleracea* inflorescences. The probes did not contain any MADS box sequences in order to avoid cross-hybridization with other MADS box genes. Hybridization conditions were as previously described (Drews et al., *Cell* 65:991 (1991), which is herein incorporated by reference).

As with AP1, CAL RNA accumulated in young flower primordia, consistent with the ability of CAL to substitute for AP1 in specifying floral meristems. In contrast to AP1 RNA, however, which accumulated at high levels throughout sepal and petal development, CAL RNA was detected only at very low levels in these organs. These results demonstrate that CAL was unable to substitute for AP1 in specifying sepals and petals, at least in part as a result of the relatively low levels of CAL RNA in these developing organs.

C. Molecular Basis of the Cauliflower Phenotype

The cal phenotype in Arabidopsis is similar to the inflorescence structure that develops in the closely related species *Brassica oleracea* var. *botrytis*, the cultivated garden variety of cauliflower, indicating that the CAL gene can contribute to the cal phenotype of this agriculturally important species. Thus, CAL gene homologs were isolated from a *Brassica oleracea* line that produces wild-type flowers (BoCAL) and from the common garden variety of cauliflower *Brassica oleracea* var. *botrytis* (BobCAL).

The single-copy BobCAL gene (Snowball Y Improved, NK Lawn & Garden, Minneapolis, Minn.) was isolated from a size-selected genomic library in λBlueStar (Novagen) on a 16-kbp BamHI fragment with the Arabidopsis CAL gene as a probe. The BoCAL gene was isolated from a rapid cycling line (Williams and Hill, *Science* 232:1385 (1986)) by PCR on both RNA and genomic DNA. The cDNA was isolated by RT-PCR using the oligonucleotides: Bobi (5'-TCTACGAGAAATGGGAAGG-3'; SEQ ID NO: 30) and Bob2 (5'-GTCGATATATGGCGAGTCC-3'; SEQ ID NO: 31). The 5' portion of the gene was obtained using oligonucleotides Bob 1 (SEQ ID NO: 30) and Bob4B (5'-CCATTGACCAGTTCGTTTG-3'; SEQ ID NO: 32). The 3' portion was obtained using oligonucleotides Bob3 (5'-GCTCCAGACTCTCACGTC-3'; SEQ ID NO: 33) and Bob2 (SEQ ID NO: 31).

RNA in situ hybridizations were performed to determine the expression pattern of BoCAL gene from *Brassica oleracea*. As in Arabidopsis, BoCAL RNA accumulated uniformly in early floral primordia and later was excluded from the cells that give rise to stamens and carpels.

DNA sequence analyses revealed that the open reading frame of the BoCAL gene is intact, whereas that of the BobCAL gene is interrupted by a stop codon in exon 5 (FIGS. 8A and 8B). Translation of the resulting BobCAL protein product is truncated after only 150 of the wild-type 255 amino acids. Because similar stop codon mutations in the fifth exon of the Arabidopsis AP1 coding sequence result in plants having a severe ap1 phenotype, the BobCAL protein likely is not functional. These results indicate that, as in Arabidopsis, the molecular basis for the cauliflower phenotype in *Brassica oleracea* var. *botrytis* is due, at least in part, to a mutation in the BobCAL gene.

EXAMPLE IV

Conversion of Inflorescence Shoots into Flowers in an CAULIFLOWER Transgenic Plant This example describes methods for producing a transgenic CAL plant.

A. Ectopic Expression of CAULIFLOWER Converts Inflorescence Shoots to Flowers

Transgenic Arabidopsis plants that ectopically express CAL in shoot meristem were generated. The full-length CAL cDNA was inserted downstream of the 35S cauliflower mosaic virus promoter in the EcoRI of pMON530 (Monsanto Co. Co., St. Louis, Mo.) This plasmid was introduced into Agrobacterium strain ASE (check) and used to transform the Columbia ecotype of Arabidopsis using a modified vacuum infiltration method described by Bechtold et al. (supra, 1993). The 96 lines generated that harbored the 35S-CAL construct had a range of weak to strong phenotypes. The transgenic plants with the strongest phenotypes (27 lines) closely resembled the tfl mutant.

35S-CAL transgenic plants had converted apical and lateral inflorescence shoots into flowers and showed an early flowering phenotype. These results demonstrate that CAL is sufficient for the conversion of shoots to flowers and for promoting early flowering.

EXAMPLE V

Conversion of Shoots into Flowers in a LEAFY Transgenic Plant

This example describes methods for producing a transgenic LFY Arabidopsis and as pen.

A. Conversion of Arabidopsis Shoots by LEAFY

Transgenic Arabidopsis plants were generated by transforming Arabidopsis with LFY under the control of the cauliflower mosaic virus 35S promoter (CaMV35S) (Odell et al., supra, (1985)). A LFY complementary cDNA (Weigel et al, *Cell* 69:843–859 (1992), which is incorporated herein by reference) was inser ted into a T-DNA transformation vector containing a CaMV 35S promoter/3' nos cassette (Jack et al., supra, 1994). Transformed seedlings were selected for kanamycin resistance. Several hundred transformants in three different genetic backgrounds (Nossen, Wassilewskija and Columbia) were recovered and several lines were characterized in detail.

High levels of LFY RNA expression were detected by northern blot analysis. In general, Nossen lines had weaker phenotypes, especially when grown in short days. The 35S-LFY transgene of line DW151.117 (ecotype Wassilewskija) was introgressed into the erecta background by backcrossing to a Landsberg erecta strain. Plants were grown under 16 hours light and 8 hours dark. The 35S-LFY transgene provided at least as much LFY activity as the endogenous gene and completely suppressed the lfy mutant phenotype when crossed into the background of the lfy-6 null allele.

Most 35S-LFY transgenic plants lines demonstrated a very similar, dominant and heritable phenotype. Secondary shoots that arose in lateral positions were consistently replaced by solitary flowers, and higher-order shoots were absent. Although the number of rosette leaves was unchanged from the wild type, 35S-LFY plants flowered earlier than wild type; the solitary flowers in the axils of the rosette leaves developed and opened precociously. In addition, the primary shoot terminated with a flower. In the most extreme cases, a terminal flower was formed immediately above the rosette. This gain of function phenotype (conversion of shoots to flowers) is the opposite of the lfy loss of function phenotype (conversion of flowers to shoots). These results demonstrate that LFY encodes a developmental switch that is both sufficient and necessary to convert shoot meristem to flower meristem.

The effects of constitutive LFY expression differ for primary and secondary shoot meristems. Secondary meristems were transformed into flower meristem, apparently as soon as it developed, and produced only a single, solitary flower. In contrast, primary shoot meristem produced leaves and lateral flowers before being consumed in the formation of a terminal flower. These developmental differences indicate that a meristem must acquire competence to respond to the activity of a floral meristem identity gene such as LFY.

B. Conversion of Aspen Shoots by LEAFY

Given that constitutive expression of LFY induced precocious flowering during the vegetative phase of Arabidopsis, the effect of LFY on the flowering of other species was examined. The perennial tree, hybrid aspen, is derived from parental species that flower naturally only after 8–20 years of growth (Schopmeyer (ed.), *USDA Agriculture Handbook 450: Seeds of Woody Plants in the United States*, Washington D.C., USA: US Government Printing Office, pp. 645–655 (1974)). 35S-LFY aspen plants were obtained by Agrobacterium-mediated transformation of stem segments and subsequent regeneration of transgenic shoots in tissue culture.

Hybrid aspen was transformed exactly as described by Nilsson et al. (*Transgen. Res.* 1:209–220 (1992), which is incorporated herein by reference). Levels of LFY RNA expression were similar to those of 35S-LFY Arabidopsis, as determined by northern blot analysis. The number of vegetative leaves varied between different regenerating shoots, and those with a higher number of vegetative leaves formed roots, allowing for transfer to the greenhouse. Individual flowers were removed either from primary transformants that had been transferred to the greenhouse, or from catkins collected in spring, 1995, at Carlshem, Umea, Sweden) from a tree whose age was determined by counting the number of annual rings in a core extracted with an increment borer at 1.5 meters above ground level. Flowers were fixed in formaldehyde/acetic acid/ethanol and destained in ethanol before photography.

The overall phenotype of 35S-LFY aspen was similar to that of 35S-LFY Arabidopsis. In wild-type plants of both species, flowers normally are formed in lateral positions on inflorescence shoots. In aspen, these inflorescence shoots, called catkins, arise from the leaf axils of adult trees. In both 35S-LFY Arabidopsis and 35S-LFY aspen, solitary flowers were formed instead of shoots in the axils of vegetative leaves. Moreover, as in Arabidopsis, the secondary shoots of trangenic aspen were more severely affected than the primary shoot.

Regenerating 35S-LFY aspen shoots initially produced solitary flowers in the axils of normal leaves. However, the number of vegetative leaves was limited, and the shoot meristem was prematurely consumed in the formation of an aberrant terminal flower. Precocious flower development was specific to 35S-LFY transformants and was not observed in non-transgenic controls. Furthermore, not a single instance of precocious flower development has been observed in more than 1,500 other lines of transgenic aspen generated with various constructs from 1989 to 1995 at the Swedish University of Agricultural Sciences. These results demonstrate that a heterologous floral meristem identity gene product is active in an angiosperm.

Although the invention has been described with reference to the examples above, it should be understood that various modifications can be made without departing from the spirit of the invention. Accordingly, the invention is limited only by the following claims.

What is claimed is:

1. A method of identifying a Brassica having a "cauliflower" phenotype, comprising the steps of:
   (a) obtaining from a Brassica a sample comprising nucleic acid; and
   (b) assaying said sample for the presence or absence of a polymorphism associated with a CAL locus, said CAL locus comprising a modified CAL allele that does not encode an active CAL gene product, wherein the presence of said polymorphism identifies said Brassica as a Brassica having a "cauliflower" phenotype.

2. The method of claim 1, wherein said modified CAL allele encodes a truncated CAL gene product.

3. The method of claim 1, wherein said polymorphism is within a CAL gene.

4. The method of claim 3, wherein said polymorphism is detectable as a restriction fragment length polymorphism.

5. The method of claim 4, wherein said polymorphism is at nucleotide 451 of the nucleic acid sequence shown in FIG. 7 (SEQ ID NO: 13).

* * * * *

SEQUENCE LISTING (1) GENERAL INFORMATION:

(iii) NUMBER OF SEQUENCES: 33

(2) INFORMATION FOR SEQ ID NO:1:

(i) SEQUENCE CHARACTERISTICS:
      (A) LENGTH: 1215 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: CDS
      (B) LOCATION: join(141..905, 909..971, 975..1047)

(ix) FEATURE:
      (A) NAME/KEY: misc_feature
      (B) LOCATION: 1..1215
      (D) OTHER INFORMATION: /note= "product = Arabidopsis thaliana AP1"

(xi) SEQUENCE DESCRIPTION: SEQ ID NO:1:

```
GAATTCCTCG AGCTACGTCA GGGCCCTGAC GTAGCTCGAA GTCTGAGCTC TTCTTTATAT      60

CTCTCTTGTA GTTTCTTATT GGGGGTCTTT GTTTTGTTTG GTTCTTTTAG AGTAAGAAGT     120

TTCTTAAAAA AGGATCAAAA ATG GGA AGG GGT AGG GTT CAA TTG AAG AGG        170
                     Met Gly Arg Gly Arg Val Gln Leu Lys Arg
                       1               5                  10

ATA GAG AAC AAG ATC AAT AGA CAA GTG ACA TTC TCG AAA AGA AGA GCT      218
```

-continued

```
Ile Glu Asn Lys Ile Asn Arg Gln Val Thr Phe Ser Lys Arg Arg Ala
             15                  20                  25

GGT CTT TTG AAG AAA GCT CAT GAG ATC TCT GTT CTC TGT GAT GCT GAA      266
Gly Leu Leu Lys Lys Ala His Glu Ile Ser Val Leu Cys Asp Ala Glu
             30                  35                  40

GTT GCT CTT GTT GTC TTC TCC CAT AAG GGA AAA CTC TTC GAA TAC TCC      314
Val Ala Leu Val Val Phe Ser His Lys Gly Lys Leu Phe Glu Tyr Ser
             45                  50                  55

ACT GAT TCT TGT ATG GAG AAG ATA CTT GAA CGC TAT GAG AGG TAC TCT      362
Thr Asp Ser Cys Met Glu Lys Ile Leu Glu Arg Tyr Glu Arg Tyr Ser
     60                  65                  70

TAC GCC GAA AGA CAG CTT ATT GCA CCT GAG TCC GAC GTC AAT ACA AAC      410
Tyr Ala Glu Arg Gln Leu Ile Ala Pro Glu Ser Asp Val Asn Thr Asn
 75                  80                  85                  90

TGG TCG ATG GAG TAT AAC AGG CTT AAG GCT AAG ATT GAG CTT TTG GAG      458
Trp Ser Met Glu Tyr Asn Arg Leu Lys Ala Lys Ile Glu Leu Leu Glu
                 95                 100                 105

AGA AAC CAG AGG CAT TAT CTT GGG GAA GAC TTG CAA GCA ATG AGC CCT      506
Arg Asn Gln Arg His Tyr Leu Gly Glu Asp Leu Gln Ala Met Ser Pro
                110                 115                 120

AAA GAG CTT CAG AAT CTG GAG CAG CAG CTT GAC ACT GCT CTT AAG CAC      554
Lys Glu Leu Gln Asn Leu Glu Gln Gln Leu Asp Thr Ala Leu Lys His
             125                 130                 135

ATC CGC ACT AGA AAA AAC CAA CTT ATG TAC GAG TCC ATC AAT GAG CTC      602
Ile Arg Thr Arg Lys Asn Gln Leu Met Tyr Glu Ser Ile Asn Glu Leu
         140                 145                 150

CAA AAA AAG GAG AAG GCC ATA CAG GAG CAA AAC AGC ATG CTT TCT AAA      650
Gln Lys Lys Glu Lys Ala Ile Gln Glu Gln Asn Ser Met Leu Ser Lys
155                 160                 165                 170

CAG ATC AAG GAG AGG GAA AAA ATT CTT AGG GCT CAA CAG GAG CAG TGG      698
Gln Ile Lys Glu Arg Glu Lys Ile Leu Arg Ala Gln Gln Glu Gln Trp
                175                 180                 185

GAT CAG CAG AAC CAA GGC CAC AAT ATG CCT CCC CCT CTG CCA CCG CAG      746
Asp Gln Gln Asn Gln Gly His Asn Met Pro Pro Pro Leu Pro Pro Gln
                190                 195                 200

CAG CAC CAA ATC CAG CAT CCT TAC ATG CTC TCT CAT CAG CCA TCT CCT      794
Gln His Gln Ile Gln His Pro Tyr Met Leu Ser His Gln Pro Ser Pro
             205                 210                 215

TTT CTC AAC ATG GGT GGT CTG TAT CAA GAA GAT GAT CCT ATG GCA ATG      842
Phe Leu Asn Met Gly Gly Leu Tyr Gln Glu Asp Asp Pro Met Ala Met
         220                 225                 230

AGG AAT GAT CTC GAA CTG ACT CTT GAA CCC GTT TAC AAC TGC AAC CTT      890
Arg Asn Asp Leu Glu Leu Thr Leu Glu Pro Val Tyr Asn Cys Asn Leu
235                 240                 245                 250

GGC TGC TTC GCC GCA TGA AGC ATT TCC ATA TAT ATA TTT GTA ATC GTC      938
Gly Cys Phe Ala Ala     Ser Ile Ser Ile Tyr Ile Phe Val Ile Val
                255                 260                 265

AAC AAT AAA AAC AGT TTG CCA CAT ACA TAT AAA TAG TGG CTA GGC TCT      986
Asn Asn Lys Asn Ser Leu Pro His Thr Tyr Lys     Trp Leu Gly Ser
                270                 275                 280

TTT CAT CCA ATT AAT ATA TTT TGG CAA ATG TTC GAT GTT CTT ATA TCA     1034
Phe His Pro Ile Asn Ile Phe Trp Gln Met Phe Asp Val Leu Ile Ser
                285                 290                 295

TCA TAT ATA AATTAGCAGG CTCCTTTCTT CTTTTGTAAT TGATAAGTT             1083
Ser Tyr Ile Asn
             300

TATTTGCTTC AATATGGAGC AAAATTGTAA TATATTTGAA GGTCAGAGAG AATGAACGTG   1143

AACTTAATAG AAAAAAAAAA AAAAAAAAAA AAAAAAAAAA AAAAAAAAAA CCCGACGTAG   1203
```

CTCGAGGAAT TC                                                    1215

(2) INFORMATION FOR SEQ ID NO:2:

(i) SEQUENCE CHARACTERISTICS:
        (A) LENGTH: 300 amino acids
        (B) TYPE: amino acid
        (D) TOPOLOGY: linear (ii) MOLECULE TYPE: protein (xi) SEQUENCE DESCRIPTION: SEQ ID NO:2:

```
Met Gly Arg Gly Arg Val Gln Leu Lys Arg Ile Glu Asn Lys Ile Asn
 1               5                  10                  15

Arg Gln Val Thr Phe Ser Lys Arg Arg Ala Gly Leu Leu Lys Lys Ala
            20                  25                  30

His Glu Ile Ser Val Leu Cys Asp Ala Glu Val Ala Leu Val Val Phe
        35                  40                  45

Ser His Lys Gly Lys Leu Phe Glu Tyr Ser Thr Asp Ser Cys Met Glu
    50                  55                  60

Lys Ile Leu Glu Arg Tyr Glu Arg Tyr Ser Tyr Ala Glu Arg Gln Leu
65                  70                  75                  80

Ile Ala Pro Glu Ser Asp Val Asn Thr Asn Trp Ser Met Glu Tyr Asn
                85                  90                  95

Arg Leu Lys Ala Lys Ile Glu Leu Leu Glu Arg Asn Gln Arg His Tyr
            100                 105                 110

Leu Gly Glu Asp Leu Gln Ala Met Ser Pro Lys Glu Leu Gln Asn Leu
        115                 120                 125

Glu Gln Gln Leu Asp Thr Ala Leu Lys His Ile Arg Thr Arg Lys Asn
    130                 135                 140

Gln Leu Met Tyr Glu Ser Ile Asn Glu Leu Gln Lys Lys Glu Lys Ala
145                 150                 155                 160

Ile Gln Glu Gln Asn Ser Met Leu Ser Lys Gln Ile Lys Glu Arg Glu
                165                 170                 175

Lys Ile Leu Arg Ala Gln Gln Glu Gln Trp Asp Gln Asn Gln Asn Gly
            180                 185                 190

His Asn Met Pro Pro Leu Pro Pro Gln His Gln Ile Gln His
        195                 200                 205

Pro Tyr Met Leu Ser His Gln Pro Ser Pro Phe Leu Asn Met Gly Gly
    210                 215                 220

Leu Tyr Gln Glu Asp Asp Pro Met Ala Met Arg Asn Asp Leu Glu Leu
225                 230                 235                 240

Thr Leu Glu Pro Val Tyr Asn Cys Asn Leu Gly Cys Phe Ala Ala Ser
                245                 250                 255

Ile Ser Ile Tyr Ile Phe Val Ile Val Asn Asn Lys Asn Ser Leu Pro
            260                 265                 270

His Thr Tyr Lys Trp Leu Gly Ser Phe His Pro Ile Asn Ile Phe Trp
        275                 280                 285

Gln Met Phe Asp Val Leu Ile Ser Ser Tyr Ile Asn
    290                 295                 300
```

(2) INFORMATION FOR SEQ ID NO:3:

(i) SEQUENCE CHARACTERISTICS:
        (A) LENGTH: 794 base pairs
        (B) TYPE: nucleic acid
        (C) STRANDEDNESS: double
        (D) TOPOLOGY: linear (ii) MOLECULE TYPE: cDNA (ix) FEATURE:
(A) NAME/KEY: CDS
(B) LOCATION: 36..794

(ix) FEATURE:
(A) NAME/KEY: misc_feature
(B) LOCATION: 1..794
(D) OTHER INFORMATION: /note= "product = Brassica oleracea AP1"

(xi) SEQUENCE DESCRIPTION: SEQ ID NO:3:

```
TCTTAGAGGA AATAGTTCCT TTAAAAGGGA TAAAA ATG GGA AGG GGT AGG GTT            53
                                       Met Gly Arg Gly Arg Val
                                         1               5

CAG TTG AAG AGG ATA GAA AAC AAG ATC AAT AGA CAA GTG ACA TTC TCG          101
Gln Leu Lys Arg Ile Glu Asn Lys Ile Asn Arg Gln Val Thr Phe Ser
             10                  15                  20

AAA AGA AGA GCT GGT CTT ATG AAG AAA GCT CAT GAG ATC TCT GTT CTG          149
Lys Arg Arg Ala Gly Leu Met Lys Lys Ala His Glu Ile Ser Val Leu
         25                  30                  35

TGT GAT GCT GAA GTT GCG CTT GTT GTC TTC TCC CAT AAG GGG AAA CTC          197
Cys Asp Ala Glu Val Ala Leu Val Val Phe Ser His Lys Gly Lys Leu
     40                  45                  50

TTT GAA TAC TCC ACT GAT TCT TGT ATG GAG AAG ATA CTT GAA CGC TAT          245
Phe Glu Tyr Ser Thr Asp Ser Cys Met Glu Lys Ile Leu Glu Arg Tyr
 55                  60                  65                  70

GAG AGA TAC TCT TAC GCC GAG AGA CAG CTT ATA GCA CCT GAG TCC GAC          293
Glu Arg Tyr Ser Tyr Ala Glu Arg Gln Leu Ile Ala Pro Glu Ser Asp
                 75                  80                  85

TCC AAT ACG AAC TGG TCG ATG GAG TAT AAT AGG CTT AAG GCT AAG ATT          341
Ser Asn Thr Asn Trp Ser Met Glu Tyr Asn Arg Leu Lys Ala Lys Ile
             90                  95                 100

GAG CTT TTG GAG AGA AAC CAG AGG CAC TAT CTT GGG GAA GAC TTG CAA          389
Glu Leu Leu Glu Arg Asn Gln Arg His Tyr Leu Gly Glu Asp Leu Gln
        105                 110                 115

GCA ATG AGC CCT AAG GAA CTC CAG AAT CTA GAG CAA CAG CTT GAT ACT          437
Ala Met Ser Pro Lys Glu Leu Gln Asn Leu Glu Gln Gln Leu Asp Thr
    120                 125                 130

GCT CTT AAG CAC ATC CGC TCT AGA AAA AAC CAA CTT ATG TAC GAC TCC          485
Ala Leu Lys His Ile Arg Ser Arg Lys Asn Gln Leu Met Tyr Asp Ser
135                 140                 145                 150

ATC AAT GAG CTC CAA AGA AAG GAG AAA GCC ATA CAG GAA CAA AAC AGC          533
Ile Asn Glu Leu Gln Arg Lys Glu Lys Ala Ile Gln Glu Gln Asn Ser
                155                 160                 165

ATG CTT TCC AAG CAG ATT AAG GAG AGG GAA AAC GTT CTT AGG GCG CAA          581
Met Leu Ser Lys Gln Ile Lys Glu Arg Glu Asn Val Leu Arg Ala Gln
            170                 175                 180

CAA GAG CAA TGG GAC GAG CAG AAC CAT GGC CAT AAT ATG CCT CCG CCT          629
Gln Glu Gln Trp Asp Glu Gln Asn His Gly His Asn Met Pro Pro Pro
        185                 190                 195

CCA CCC CCG CAG CAG CAT CAA ATC CAG CAT CCT TAC ATG CTC TCT CAT          677
Pro Pro Pro Gln Gln His Gln Ile Gln His Pro Tyr Met Leu Ser His
    200                 205                 210

CAG CCA TCT CCT TTT CTC AAC ATG GGG GGG CTG TAT CAA GAA GAA GAT          725
Gln Pro Ser Pro Phe Leu Asn Met Gly Gly Leu Tyr Gln Glu Glu Asp
215                 220                 225                 230

CAA ATG GCA ATG AGG AGG AAC GAT CTC GAT CTG TCT CTT GAA CCC GGT          773
Gln Met Ala Met Arg Arg Asn Asp Leu Asp Leu Ser Leu Glu Pro Gly
                235                 240                 245
```

```
TAT AAC TGC AAT CTC GGC TGC                                                      794
Tyr Asn Cys Asn Leu Gly Cys
            250
```

(2) INFORMATION FOR SEQ ID NO:4:

(i) SEQUENCE CHARACTERISTICS:
        (A) LENGTH: 253 amino acids
        (B) TYPE: amino acid
        (D) TOPOLOGY: linear (ii) MOLECULE TYPE: protein (xi) SEQUENCE DESCRIPTION: SEQ ID NO:4:

```
Met Gly Arg Gly Arg Val Gln Leu Lys Arg Ile Glu Asn Lys Ile Asn
 1               5                  10                  15

Arg Gln Val Thr Phe Ser Lys Arg Arg Ala Gly Leu Met Lys Lys Ala
            20                  25                  30

His Glu Ile Ser Val Leu Cys Asp Ala Glu Val Ala Leu Val Val Phe
        35                  40                  45

Ser His Lys Gly Lys Leu Phe Glu Tyr Ser Thr Asp Ser Cys Met Glu
    50                  55                  60

Lys Ile Leu Glu Arg Tyr Glu Arg Tyr Ser Tyr Ala Glu Arg Gln Leu
65                  70                  75                  80

Ile Ala Pro Glu Ser Asp Ser Asn Thr Asn Trp Ser Met Glu Tyr Asn
                85                  90                  95

Arg Leu Lys Ala Lys Ile Glu Leu Leu Glu Arg Asn Gln Arg His Tyr
            100                 105                 110

Leu Gly Glu Asp Leu Gln Ala Met Ser Pro Lys Glu Leu Gln Asn Leu
        115                 120                 125

Glu Gln Gln Leu Asp Thr Ala Leu Lys His Ile Arg Ser Arg Lys Asn
    130                 135                 140

Gln Leu Met Tyr Asp Ser Ile Asn Glu Leu Gln Arg Lys Glu Lys Ala
145                 150                 155                 160

Ile Gln Glu Gln Asn Ser Met Leu Ser Lys Gln Ile Lys Glu Arg Glu
                165                 170                 175

Asn Val Leu Arg Ala Gln Gln Glu Gln Trp Asp Glu Gln Asn His Gly
            180                 185                 190

His Asn Met Pro Pro Pro Pro Pro Gln Gln His Gln Ile Gln His
        195                 200                 205

Pro Tyr Met Leu Ser His Gln Pro Ser Pro Phe Leu Asn Met Gly Gly
    210                 215                 220

Leu Tyr Gln Glu Glu Asp Gln Met Ala Met Arg Arg Asn Asp Leu Asp
225                 230                 235                 240

Leu Ser Leu Glu Pro Gly Tyr Asn Cys Asn Leu Gly Cys
                245                 250
```

(2) INFORMATION FOR SEQ ID NO:5:

(i) SEQUENCE CHARACTERISTICS:
        (A) LENGTH: 768 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..766

(ix) FEATURE:
    (A) NAME/KEY: misc_feature
    (B) LOCATION: 1..768
    (D) OTHER INFORMATION: /note= "product = Brassica oleracea
        var. botrytis AP1"

(xi) SEQUENCE DESCRIPTION: SEQ ID NO:5:

| | | | | | | | | | | | | | | | | |
|---|---|---|---|---|---|---|---|---|---|---|---|---|---|---|---|---|
| ATG | GGA | AGG | GGT | AGG | GTT | CAG | TTG | AAG | AGG | ATA | GAA | AAC | AAG | ATC | AAT | 48 |
| Met | Gly | Arg | Gly | Arg | Val | Gln | Leu | Lys | Arg | Ile | Glu | Asn | Lys | Ile | Asn | |
| 1 | | | | 5 | | | | | 10 | | | | | 15 | | |
| AGA | CAA | GTG | ACA | TTC | TCG | AAA | AGA | AGA | GCT | GGT | CTT | ATG | AAG | AAA | GCT | 96 |
| Arg | Gln | Val | Thr | Phe | Ser | Lys | Arg | Arg | Ala | Gly | Leu | Met | Lys | Lys | Ala | |
| | | | 20 | | | | | 25 | | | | | 30 | | | |
| CAT | GAG | ATC | TCT | GTT | CTG | TGT | GAT | GCT | GAA | GTT | GCG | CTT | GTT | GTC | TTC | 144 |
| His | Glu | Ile | Ser | Val | Leu | Cys | Asp | Ala | Glu | Val | Ala | Leu | Val | Val | Phe | |
| | | 35 | | | | | 40 | | | | | 45 | | | | |
| TCC | CAT | AAG | GGG | AAA | CTC | TTT | GAA | TAC | CCC | ACT | GAT | TCT | TGT | ATG | GAG | 192 |
| Ser | His | Lys | Gly | Lys | Leu | Phe | Glu | Tyr | Pro | Thr | Asp | Ser | Cys | Met | Glu | |
| | 50 | | | | | 55 | | | | | 60 | | | | | |
| GAG | ATA | CTT | GAA | CGC | TAT | GAG | AGA | TAC | TCT | TAC | GCC | GAG | AGA | CAG | CTT | 240 |
| Glu | Ile | Leu | Glu | Arg | Tyr | Glu | Arg | Tyr | Ser | Tyr | Ala | Glu | Arg | Gln | Leu | |
| 65 | | | | | 70 | | | | | 75 | | | | | 80 | |
| ATA | GCA | CCT | GAG | TCC | GAC | TCC | AAT | ACG | AAC | TGG | TCG | ATG | GAG | TAT | AAT | 288 |
| Ile | Ala | Pro | Glu | Ser | Asp | Ser | Asn | Thr | Asn | Trp | Ser | Met | Glu | Tyr | Asn | |
| | | | | 85 | | | | | 90 | | | | | 95 | | |
| AGG | CTT | AAG | GCT | AAG | ATT | GAG | CTT | TTG | GAG | AGA | AAC | CAG | AGG | CAC | TAT | 336 |
| Arg | Leu | Lys | Ala | Lys | Ile | Glu | Leu | Leu | Glu | Arg | Asn | Gln | Arg | His | Tyr | |
| | | | 100 | | | | | 105 | | | | | 110 | | | |
| CTT | GGG | GAA | GAC | TTG | CAA | GCA | ATG | AGC | CCT | AAG | GAA | CTC | CAG | AAT | CTA | 384 |
| Leu | Gly | Glu | Asp | Leu | Gln | Ala | Met | Ser | Pro | Lys | Glu | Leu | Gln | Asn | Leu | |
| | | 115 | | | | | 120 | | | | | 125 | | | | |
| GAG | CAA | CAG | CTT | GAT | ACT | GCT | CTT | AAG | CAC | ATC | CGC | TCT | AGA | AAA | AAC | 432 |
| Glu | Gln | Gln | Leu | Asp | Thr | Ala | Leu | Lys | His | Ile | Arg | Ser | Arg | Lys | Asn | |
| | 130 | | | | | 135 | | | | | 140 | | | | | |
| CAA | CTT | ATG | TAC | GAC | TCC | ATC | AAT | GAG | CTC | CAA | AGA | AAG | GAG | AAA | GCC | 480 |
| Gln | Leu | Met | Tyr | Asp | Ser | Ile | Asn | Glu | Leu | Gln | Arg | Lys | Glu | Lys | Ala | |
| 145 | | | | | 150 | | | | | 155 | | | | | 160 | |
| ATA | CAG | GAA | CAA | AAC | AGC | ATG | CTT | TCC | AAG | CAG | ATT | AAG | GAG | AGG | GAA | 528 |
| Ile | Gln | Glu | Gln | Asn | Ser | Met | Leu | Ser | Lys | Gln | Ile | Lys | Glu | Arg | Glu | |
| | | | | 165 | | | | | 170 | | | | | 175 | | |
| AAC | GTT | CTT | AGG | GCG | CAA | CAA | GAG | CAA | TGG | GAC | GAG | CAG | AAC | CAT | GGC | 576 |
| Asn | Val | Leu | Arg | Ala | Gln | Gln | Glu | Gln | Trp | Asp | Glu | Gln | Asn | His | Gly | |
| | | | 180 | | | | | 185 | | | | | 190 | | | |
| CAT | AAT | ATG | CCT | CCG | CCT | CCA | CCC | CCG | CAG | CAG | CAT | CAA | ATC | CAG | CAT | 624 |
| His | Asn | Met | Pro | Pro | Pro | Pro | Pro | Pro | Gln | Gln | His | Gln | Ile | Gln | His | |
| | | 195 | | | | | 200 | | | | | 205 | | | | |
| CCT | TAC | ATG | CTC | TCT | CAT | CAG | CCA | TCT | CCT | TTT | CTC | AAC | ATG | GGA | GGG | 672 |
| Pro | Tyr | Met | Leu | Ser | His | Gln | Pro | Ser | Pro | Phe | Leu | Asn | Met | Gly | Gly | |
| | 210 | | | | | 215 | | | | | 220 | | | | | |
| CTG | TAT | CAA | GAA | GAA | GAT | CAA | ATG | GCA | ATG | AGG | AGG | AAC | GAT | CTC | GAT | 720 |
| Leu | Tyr | Gln | Glu | Glu | Asp | Gln | Met | Ala | Met | Arg | Arg | Asn | Asp | Leu | Asp | |
| 225 | | | | | 230 | | | | | 235 | | | | | 240 | |
| CTG | TCT | CTT | GAA | CCC | GTT | TAC | AAC | TGC | AAC | CTT | GGC | CGT | CGC | TGC | T | 766 |
| Leu | Ser | Leu | Glu | Pro | Val | Tyr | Asn | Cys | Asn | Leu | Gly | Arg | Arg | Cys | | |
| | | | | 245 | | | | | 250 | | | | | 255 | | |
| GA | | | | | | | | | | | | | | | | 768 |

(2) INFORMATION FOR SEQ ID NO:6:

(i) SEQUENCE CHARACTERISTICS:
       (A) LENGTH: 255 amino acids (B) TYPE: amino acid
                (D) TOPOLOGY: linear (ii) MOLECULE TYPE: protein (xi) SEQUENCE DESCRIPTION: SEQ ID NO:6:

Met Gly Arg Gly Arg Val Gln Leu Lys Arg Ile Glu Asn Lys Ile Asn
 1               5                  10                  15

Arg Gln Val Thr Phe Ser Lys Arg Arg Ala Gly Leu Met Lys Lys Ala
            20                  25                  30

His Glu Ile Ser Val Leu Cys Asp Ala Glu Val Ala Leu Val Val Phe
        35                  40                  45

Ser His Lys Gly Lys Leu Phe Glu Tyr Pro Thr Asp Ser Cys Met Glu
    50                  55                  60

Glu Ile Leu Glu Arg Tyr Glu Arg Tyr Ser Tyr Ala Glu Arg Gln Leu
65                  70                  75                  80

Ile Ala Pro Glu Ser Asp Ser Asn Thr Asn Trp Ser Met Glu Tyr Asn
                85                  90                  95

Arg Leu Lys Ala Lys Ile Glu Leu Leu Glu Arg Asn Gln Arg His Tyr
            100                 105                 110

Leu Gly Glu Asp Leu Gln Ala Met Ser Pro Lys Glu Leu Gln Asn Leu
        115                 120                 125

Glu Gln Gln Leu Asp Thr Ala Leu Lys His Ile Arg Ser Arg Lys Asn
    130                 135                 140

Gln Leu Met Tyr Asp Ser Ile Asn Glu Leu Gln Arg Lys Glu Lys Ala
145                 150                 155                 160

Ile Gln Glu Gln Asn Ser Met Leu Ser Lys Gln Ile Lys Glu Arg Glu
                165                 170                 175

Asn Val Leu Arg Ala Gln Gln Glu Gln Trp Asp Glu Gln Asn His Gly
            180                 185                 190

His Asn Met Pro Pro Pro Pro Pro Gln Gln His Gln Ile Gln His
        195                 200                 205

Pro Tyr Met Leu Ser His Gln Pro Ser Pro Phe Leu Asn Met Gly Gly
    210                 215                 220

Leu Tyr Gln Glu Glu Asp Gln Met Ala Met Arg Arg Asn Asp Leu Asp
225                 230                 235                 240

Leu Ser Leu Glu Pro Val Tyr Asn Cys Asn Leu Gly Arg Arg Cys
                245                 250                 255

(2) INFORMATION FOR SEQ ID NO:7:

(i) SEQUENCE CHARACTERISTICS:
            (A) LENGTH: 1345 base pairs
            (B) TYPE: nucleic acid
            (C) STRANDEDNESS: double
            (D) TOPOLOGY: linear (ii) MOLECULE TYPE: cDNA (ix) FEATURE:
            (A) NAME/KEY: CDS
            (B) LOCATION: 149..968

(ix) FEATURE:
            (A) NAME/KEY: misc_feature
            (B) LOCATION: 1..1345
            (D) OTHER INFORMATION: /note= "product = Zea mays AP1"

(xi) SEQUENCE DESCRIPTION: SEQ ID NO:7:

GCACGAGTCC TCCTCCTCCT CGCATCCCAC CCCACCCCAC CTTCTCCTTA AAGCTACCTG      60

```
CCTACCCGGC GGTTGCGCGC CGCAATCGAT CGACCGGAAG AGAAAGAGCA GCTAGCTAGC         120

TAGCAGATCG AGCACGGCA ACAAGGCG ATG GGG CGC GGC AAG GTA CAG CTG             172
                              Met Gly Arg Gly Lys Val Gln Leu
                                1               5

AAG CGG ATA GAG AAC AAG ATA AAC CGG CAG GTG ACC TTC TCC AAG CGC           220
Lys Arg Ile Glu Asn Lys Ile Asn Arg Gln Val Thr Phe Ser Lys Arg
        10              15                  20

CGG AAC GGC CTG CTC AAG AAG GCG CAC GAG ATC TCC GTC CTC TGC GAT           268
Arg Asn Gly Leu Leu Lys Lys Ala His Glu Ile Ser Val Leu Cys Asp
25              30                  35                  40

GCC GAG GTC GCC GTC ATC GTC TTC TCC CCC AAG GGC AAG CTC TAC GAG           316
Ala Glu Val Ala Val Ile Val Phe Ser Pro Lys Gly Lys Leu Tyr Glu
                45                  50                  55

TAC GCC ACC GAC TCC CGC ATG GAC AAA ATT CTT GAA CGC TAT GAG CGA           364
Tyr Ala Thr Asp Ser Arg Met Asp Lys Ile Leu Glu Arg Tyr Glu Arg
            60                  65                  70

TAT TCC TAT GCT GAA AAG GCT CTT ATT TCA GCT GAA TCT GAA AGT GAG           412
Tyr Ser Tyr Ala Glu Lys Ala Leu Ile Ser Ala Glu Ser Glu Ser Glu
        75                  80                  85

GGA AAT TGG TGC CAC GAA TAC AGG AAA CTG AAG GCC AAA ATT GAG ACC           460
Gly Asn Trp Cys His Glu Tyr Arg Lys Leu Lys Ala Lys Ile Glu Thr
    90                  95                  100

ATA CAA AAA TGC CAC AAG CAC CTG ATG GGA GAG GAT CTA GAG TCT TTG           508
Ile Gln Lys Cys His Lys His Leu Met Gly Glu Asp Leu Glu Ser Leu
105             110                 115                 120

AAT CCC AAA GAG CTC CAG CAA CTA GAG CAG CAG CTG GAT AGC TCA CTG           556
Asn Pro Lys Glu Leu Gln Gln Leu Glu Gln Gln Leu Asp Ser Ser Leu
                125                 130                 135

AAG CAC ATC AGA TCA AGG AAG AGC CAC CTT ATG GCC GAG TCT ATT TCT           604
Lys His Ile Arg Ser Arg Lys Ser His Leu Met Ala Glu Ser Ile Ser
            140                 145                 150

GAG CTA CAG AAG AAG GAG AGG TCA CTG CAG GAG GAG AAC AAG GCT CTG           652
Glu Leu Gln Lys Lys Glu Arg Ser Leu Gln Glu Glu Asn Lys Ala Leu
        155                 160                 165

CAG AAG GAA CTT GCG GAG AGG CAG AAG GCC GTC GCG AGC CGG CAG CAG           700
Gln Lys Glu Leu Ala Glu Arg Gln Lys Ala Val Ala Ser Arg Gln Gln
    170                 175                 180

CAG CAA CAG CAG CAG GTG CAG TGG GAC CAG CAG ACA CAT GCC CAG GCC           748
Gln Gln Gln Gln Gln Val Gln Trp Asp Gln Gln Thr His Ala Gln Ala
185                 190                 195                 200

CAG ACA AGC TCA TCG TCC TCC TTC ATG ATG AGG CAG GAT CAG CAG               796
Gln Thr Ser Ser Ser Ser Ser Phe Met Met Arg Gln Asp Gln Gln
                205                 210                 215

GGA CTG CCG CCT CCA CAC AAC ATC TGC TTC CCG CCG TTG ACA ATG GGA           844
Gly Leu Pro Pro Pro His Asn Ile Cys Phe Pro Pro Leu Thr Met Gly
            220                 225                 230

GAT AGA GGT GAA GAG CTG GCT GCG GCG GCG GCG GCG CAG CAG CAG CAG           892
Asp Arg Gly Glu Glu Leu Ala Ala Ala Ala Ala Ala Gln Gln Gln Gln
        235                 240                 245

CCA CTG CCG GGG CAG GCG CAA CCG CAG CTC CGC ATC GCA GGT CTG CCA           940
Pro Leu Pro Gly Gln Ala Gln Pro Gln Leu Arg Ile Ala Gly Leu Pro
    250                 255                 260

CCA TGG ATG CTG AGC CAC CTC AAT GCA T AAGGAGAGGG TCGATGAACA               988
Pro Trp Met Leu Ser His Leu Asn Ala
265                 270

CATCGACCTC CTCTCTCTCT CTCTCTCGTC ATGGATCATG ACGTACGCGT ACCATATGGT        1048

TGCTGTGCCT GCCCCCATCG ATCGCGAGCA ATGGCACGCT CATGCAAGTG ATCATTGCTC        1108

CCCGTTGGTT AAACCCTAGC CTATGTTCAT GGCGTCAGCA ACTAAGCTAA ACTATTGTTA        1168
```

```
TGTTTGCAAG AAAGGGTAAA CCCGCTAGCT GTGTAATCTT GTCCAGCTAT CAGTATGCTT    1228

GTTACTGCCC AGTTACCCTT GAATCTAGCG GCGCTTTTGG TGAGAGGGTG CAGTTTACTT    1288

TAAACATGGT TCGTGACTTG CTGTAAATAG TAGTATTAAT CGATTTGGGC ATCTAAA      1345
```

(2) INFORMATION FOR SEQ ID NO:8:

(i) SEQUENCE CHARACTERISTICS:
        (A) LENGTH: 273 amino acids
        (B) TYPE: amino acid
        (D) TOPOLOGY: linear (ii) MOLECULE TYPE: protein (xi) SEQUENCE DESCRIPTION: SEQ ID NO:8:

```
Met Gly Arg Gly Lys Val Gln Leu Lys Arg Ile Glu Asn Lys Ile Asn
 1               5                  10                  15

Arg Gln Val Thr Phe Ser Lys Arg Arg Asn Gly Leu Leu Lys Lys Ala
                20                  25                  30

His Glu Ile Ser Val Leu Cys Asp Ala Glu Val Ala Val Ile Val Phe
            35                  40                  45

Ser Pro Lys Gly Lys Leu Tyr Glu Tyr Ala Thr Asp Ser Arg Met Asp
        50                  55                  60

Lys Ile Leu Glu Arg Tyr Glu Arg Tyr Ser Tyr Ala Glu Lys Ala Leu
65                  70                  75                  80

Ile Ser Ala Glu Ser Glu Ser Glu Gly Asn Trp Cys His Glu Tyr Arg
                85                  90                  95

Lys Leu Lys Ala Lys Ile Glu Thr Ile Gln Lys Cys His Lys His Leu
            100                 105                 110

Met Gly Glu Asp Leu Glu Ser Leu Asn Pro Lys Glu Leu Gln Gln Leu
        115                 120                 125

Glu Gln Gln Leu Asp Ser Ser Leu Lys His Ile Arg Ser Arg Lys Ser
    130                 135                 140

His Leu Met Ala Glu Ser Ile Ser Glu Leu Gln Lys Lys Glu Arg Ser
145                 150                 155                 160

Leu Gln Glu Glu Asn Lys Ala Leu Gln Lys Glu Leu Ala Glu Arg Gln
                165                 170                 175

Lys Ala Val Ala Ser Arg Gln Gln Gln Gln Gln Gln Val Gln Trp
            180                 185                 190

Asp Gln Gln Thr His Ala Gln Ala Gln Thr Ser Ser Ser Ser Ser
        195                 200                 205

Phe Met Met Arg Gln Asp Gln Gln Gly Leu Pro Pro His Asn Ile
    210                 215                 220

Cys Phe Pro Pro Leu Thr Met Gly Asp Arg Gly Glu Glu Leu Ala Ala
225                 230                 235                 240

Ala Ala Ala Ala Gln Gln Gln Pro Leu Pro Gly Gln Ala Gln Pro
                245                 250                 255

Gln Leu Arg Ile Ala Gly Leu Pro Pro Trp Met Leu Ser His Leu Asn
            260                 265                 270

Ala
```

(2) INFORMATION FOR SEQ ID NO:9:

(i) SEQUENCE CHARACTERISTICS:
        (A) LENGTH: 779 base pairs
        (B) TYPE: nucleic acid
        (C) STRANDEDNESS: double (D) TOPOLOGY: linear (ii) MOLECULE TYPE: cDNA (ix) FEATURE:
        (A) NAME/KEY: CDS
        (B) LOCATION: 10..775

(ix) FEATURE:
        (A) NAME/KEY: unsure
        (B) LOCATION: 778..779
        (D) OTHER INFORMATION: /note= "N = one or more
            nucleotides."

(ix) FEATURE:
        (A) NAME/KEY: misc_feature
        (B) LOCATION: 1
        (D) OTHER INFORMATION: /note= "product = Arabidopsis
            thaliana CAL"

(xi) SEQUENCE DESCRIPTION: SEQ ID NO:9:

```
TTAAGAGAA ATG GGA AGG GGT AGG GTT GAA TTG AAG AGG ATA GAG AAC          48
          Met Gly Arg Gly Arg Val Glu Leu Lys Arg Ile Glu Asn
           1               5                  10

AAG ATC AAT AGA CAA GTG ACA TTC TCG AAA AGA AGA ACT GGT CTT TTG        96
Lys Ile Asn Arg Gln Val Thr Phe Ser Lys Arg Arg Thr Gly Leu Leu
 15                  20                  25

AAG AAA GCT CAG GAG ATC TCT GTT CTT TGT GAT GCC GAG GTT TCC CTT       144
Lys Lys Ala Gln Glu Ile Ser Val Leu Cys Asp Ala Glu Val Ser Leu
 30                  35                  40                  45

ATT GTC TTC TCC CAT AAG GGC AAA TTG TTC GAG TAC TCC TCT GAA TCT       192
Ile Val Phe Ser His Lys Gly Lys Leu Phe Glu Tyr Ser Ser Glu Ser
                 50                  55                  60

TGC ATG GAG AAG GTA CTA GAA CGC TAC GAG AGG TAT TCT TAC GCC GAG       240
Cys Met Glu Lys Val Leu Glu Arg Tyr Glu Arg Tyr Ser Tyr Ala Glu
         65                  70                  75

AGA CAG CTG ATT GCA CCT GAC TCT CAC GTT AAT GCA CAG ACG AAC TGG       288
Arg Gln Leu Ile Ala Pro Asp Ser His Val Asn Ala Gln Thr Asn Trp
     80                  85                  90

TCA ATG GAG TAT AGC AGG CTT AAG GCC AAG ATT GAG CTT TTG GAG AGA       336
Ser Met Glu Tyr Ser Arg Leu Lys Ala Lys Ile Glu Leu Leu Glu Arg
 95                 100                 105

AAC CAA AGG CAT TAT CTG GGA GAA GAG TTG GAA CCA ATG AGC CTC AAG       384
Asn Gln Arg His Tyr Leu Gly Glu Glu Leu Glu Pro Met Ser Leu Lys
110                 115                 120                 125

GAT CTC CAA AAT CTG GAG CAG CAG CTT GAG ACT GCT CTT AAG CAC ATT       432
Asp Leu Gln Asn Leu Glu Gln Gln Leu Glu Thr Ala Leu Lys His Ile
                130                 135                 140

CGC TCC AGA AAA AAT CAA CTC ATG AAT GAG TCC CTC AAC CAC CTC CAA       480
Arg Ser Arg Lys Asn Gln Leu Met Asn Glu Ser Leu Asn His Leu Gln
        145                 150                 155

AGA AAG GAG AAG GAG ATA CAG GAG GAA AAC AGC ATG CTT ACC AAA CAG       528
Arg Lys Glu Lys Glu Ile Gln Glu Glu Asn Ser Met Leu Thr Lys Gln
    160                 165                 170

ATA AAG GAG AGG GAA AAC ATC CTA AAG ACA AAA CAA ACC CAA TGT GAG       576
Ile Lys Glu Arg Glu Asn Ile Leu Lys Thr Lys Gln Thr Gln Cys Glu
175                 180                 185

CAG CTG AAC CGC AGC GTC GAC GAT GTA CCA CAG CCA CAA CCA TTT CAA       624
Gln Leu Asn Arg Ser Val Asp Asp Val Pro Gln Pro Gln Pro Phe Gln
190                 195                 200                 205

CAC CCC CAT CTT TAC ATG ATC GCT CAT CAG ACT TCT CCT TTC CTA AAT       672
His Pro His Leu Tyr Met Ile Ala His Gln Thr Ser Pro Phe Leu Asn
                210                 215                 220

ATG GGT GGT TTG TAC CAA GGA GAA GAC CAA ACG GCG ATG AGG AGG AAC       720
```

```
Met Gly Gly Leu Tyr Gln Gly Glu Asp Gln Thr Ala Met Arg Arg Asn
        225                 230                 235

AAT CTG GAT CTG ACT CTT GAA CCC ATT TAC AAT TAC CTT GGC TGT TAC      768
Asn Leu Asp Leu Thr Leu Glu Pro Ile Tyr Asn Tyr Leu Gly Cys Tyr
        240                 245                 250

GCC GCT T GANN                                                        779
Ala Ala
    255
```

(2) INFORMATION FOR SEQ ID NO:10:

(i) SEQUENCE CHARACTERISTICS:
        (A) LENGTH: 255 amino acids
        (B) TYPE: amino acid
        (D) TOPOLOGY: linear (ii) MOLECULE TYPE: protein (xi) SEQUENCE DESCRIPTION: SEQ ID NO:10:

```
Met Gly Arg Gly Arg Val Glu Leu Lys Arg Ile Glu Asn Lys Ile Asn
 1               5                  10                  15

Arg Gln Val Thr Phe Ser Lys Arg Arg Thr Gly Leu Leu Lys Lys Ala
            20                  25                  30

Gln Glu Ile Ser Val Leu Cys Asp Ala Glu Val Ser Leu Ile Val Phe
        35                  40                  45

Ser His Lys Gly Lys Leu Phe Glu Tyr Ser Ser Glu Ser Cys Met Glu
    50                  55                  60

Lys Val Leu Glu Arg Tyr Glu Arg Tyr Ser Tyr Ala Glu Arg Gln Leu
65                  70                  75                  80

Ile Ala Pro Asp Ser His Val Asn Ala Gln Thr Asn Trp Ser Met Glu
                85                  90                  95

Tyr Ser Arg Leu Lys Ala Lys Ile Glu Leu Leu Glu Arg Asn Gln Arg
            100                 105                 110

His Tyr Leu Gly Glu Glu Leu Glu Pro Met Ser Leu Lys Asp Leu Gln
        115                 120                 125

Asn Leu Glu Gln Gln Leu Glu Thr Ala Leu Lys His Ile Arg Ser Arg
    130                 135                 140

Lys Asn Gln Leu Met Asn Glu Ser Leu Asn His Leu Gln Arg Lys Glu
145                 150                 155                 160

Lys Glu Ile Gln Glu Glu Asn Ser Met Leu Thr Lys Gln Ile Lys Glu
                165                 170                 175

Arg Glu Asn Ile Leu Lys Thr Lys Gln Thr Gln Cys Glu Gln Leu Asn
            180                 185                 190

Arg Ser Val Asp Asp Val Pro Gln Pro Gln Pro Phe Gln His Pro His
        195                 200                 205

Leu Tyr Met Ile Ala His Gln Thr Ser Pro Phe Leu Asn Met Gly Gly
    210                 215                 220

Leu Tyr Gln Gly Glu Asp Gln Thr Ala Met Arg Arg Asn Asn Leu Asp
225                 230                 235                 240

Leu Thr Leu Glu Pro Ile Tyr Asn Tyr Leu Gly Cys Tyr Ala Ala
                245                 250                 255
```

(2) INFORMATION FOR SEQ ID NO:11:

(i) SEQUENCE CHARACTERISTICS:
        (A) LENGTH: 756 base pairs
        (B) TYPE: nucleic acid
        (C) STRANDEDNESS: double
        (D) TOPOLOGY: linear (ii) MOLECULE TYPE: cDNA (ix) FEATURE:
    (A) NAME/KEY: CDS
    (B) LOCATION: 1..754

(ix) FEATURE:
    (A) NAME/KEY: misc_feature
    (B) LOCATION: 1..756
    (D) OTHER INFORMATION: /note= "product = Brassica oleracea CAL"

(xi) SEQUENCE DESCRIPTION: SEQ ID NO:11:

```
ATG GGA AGG GGT AGG GTT GAA ATG AAG AGG ATA GAG AAC AAG ATC AAC        48
Met Gly Arg Gly Arg Val Glu Met Lys Arg Ile Glu Asn Lys Ile Asn
 1               5                  10                  15

CGA CAA GTG ACG TTT TCG AAA AGA AGA GCT GGT CTT TTG AAG AAA GCC        96
Arg Gln Val Thr Phe Ser Lys Arg Arg Ala Gly Leu Leu Lys Lys Ala
                20                  25                  30

CAT GAG ATC TCG ATC CTT TGT GAT GCT GAG GTT TCC CTT ATT GTC TTC       144
His Glu Ile Ser Ile Leu Cys Asp Ala Glu Val Ser Leu Ile Val Phe
            35                  40                  45

TCC CAT AAG GGG AAA CTG TTC GAG TAC TCG TCT GAA TCT TGC ATG GAG       192
Ser His Lys Gly Lys Leu Phe Glu Tyr Ser Ser Glu Ser Cys Met Glu
        50                  55                  60

AAG GTA CTA GAA CAC TAC GAG AGG TAC TCT TAC GCC GAG AAA CAG CTA       240
Lys Val Leu Glu His Tyr Glu Arg Tyr Ser Tyr Ala Glu Lys Gln Leu
 65                 70                  75                  80

AAA GTT CCA GAC TCT CAC GTC AAT GCA CAA ACG AAC TGG TCA GTG GAA       288
Lys Val Pro Asp Ser His Val Asn Ala Gln Thr Asn Trp Ser Val Glu
                85                  90                  95

TAT AGC AGG CTT AAG GCT AAG ATT GAG CTT TTG GAG AGA AAC CAA AGG       336
Tyr Ser Arg Leu Lys Ala Lys Ile Glu Leu Leu Glu Arg Asn Gln Arg
            100                 105                 110

CAT TAT CTG GGC GAA GAT TTA GAA TCA ATC AGC ATA AAG GAG CTA CAG       384
His Tyr Leu Gly Glu Asp Leu Glu Ser Ile Ser Ile Lys Glu Leu Gln
        115                 120                 125

AAT CTG GAG CAG CAG CTT GAC ACT TCT CTT AAA CAT ATT CGC TCG AGA       432
Asn Leu Glu Gln Gln Leu Asp Thr Ser Leu Lys His Ile Arg Ser Arg
    130                 135                 140

AAA AAT CAA CTA ATG CAC GAG TCC CTC AAC CAC CTC CAA AGA AAG GAG       480
Lys Asn Gln Leu Met His Glu Ser Leu Asn His Leu Gln Arg Lys Glu
145                 150                 155                 160

AAA GAA ATA CTG GAG GAA AAC AGC ATG CTT GCC AAA CAG ATA AGG GAG       528
Lys Glu Ile Leu Glu Glu Asn Ser Met Leu Ala Lys Gln Ile Arg Glu
                165                 170                 175

AGG GAG AGT ATC CTA AGG ACA CAT CAA AAC CAA TCA GAG CAG CAA AAC       576
Arg Glu Ser Ile Leu Arg Thr His Gln Asn Gln Ser Glu Gln Gln Asn
            180                 185                 190

CGC AGC CAC CAT GTA GCT CCT CAG CCG CAA CCG CAG TTA AAT CCT TAC       624
Arg Ser His His Val Ala Pro Gln Pro Gln Pro Gln Leu Asn Pro Tyr
        195                 200                 205

ATG GCA TCA TCT CCT TTC CTA AAT ATG GGT GGC ATG TAC CAA GGA GAA       672
Met Ala Ser Ser Pro Phe Leu Asn Met Gly Gly Met Tyr Gln Gly Glu
    210                 215                 220

TAT CCA ACG GCG GTG AGG AGG AAC CGT CTC GAT CTG ACT CTT GAA CCC       720
Tyr Pro Thr Ala Val Arg Arg Asn Arg Leu Asp Leu Thr Leu Glu Pro
225                 230                 235                 240

ATT TAC AAC TGC AAC CTT GGT TAC TTT GCC GCA T GA                      756
Ile Tyr Asn Cys Asn Leu Gly Tyr Phe Ala Ala
                245                 250
```

(2) INFORMATION FOR SEQ ID NO:12:

(i) SEQUENCE CHARACTERISTICS:
        (A) LENGTH: 251 amino acids
        (B) TYPE: amino acid
        (D) TOPOLOGY: linear (ii) MOLECULE TYPE: protein (xi) SEQUENCE DESCRIPTION: SEQ ID NO:12:

```
Met Gly Arg Gly Arg Val Glu Met Lys Arg Ile Glu Asn Lys Ile Asn
 1               5                  10                  15

Arg Gln Val Thr Phe Ser Lys Arg Arg Ala Gly Leu Leu Lys Lys Ala
             20                  25                  30

His Glu Ile Ser Ile Leu Cys Asp Ala Glu Val Ser Leu Ile Val Phe
         35                  40                  45

Ser His Lys Gly Lys Leu Phe Glu Tyr Ser Ser Glu Ser Cys Met Glu
     50                  55                  60

Lys Val Leu Glu His Tyr Glu Arg Tyr Ser Tyr Ala Glu Lys Gln Leu
 65                  70                  75                  80

Lys Val Pro Asp Ser His Val Asn Ala Gln Thr Asn Trp Ser Val Glu
                 85                  90                  95

Tyr Ser Arg Leu Lys Ala Lys Ile Glu Leu Leu Glu Arg Asn Gln Arg
            100                 105                 110

His Tyr Leu Gly Glu Asp Leu Glu Ser Ile Ser Ile Lys Glu Leu Gln
        115                 120                 125

Asn Leu Glu Gln Gln Leu Asp Thr Ser Leu Lys His Ile Arg Ser Arg
    130                 135                 140

Lys Asn Gln Leu Met His Glu Ser Leu Asn His Leu Gln Arg Lys Glu
145                 150                 155                 160

Lys Glu Ile Leu Glu Glu Asn Ser Met Leu Ala Lys Gln Ile Arg Glu
                165                 170                 175

Arg Glu Ser Ile Leu Arg Thr His Gln Asn Gln Ser Glu Gln Gln Asn
            180                 185                 190

Arg Ser His His Val Ala Pro Gln Pro Gln Pro Gln Leu Asn Pro Tyr
        195                 200                 205

Met Ala Ser Ser Pro Phe Leu Asn Met Gly Gly Met Tyr Gln Gly Glu
    210                 215                 220

Tyr Pro Thr Ala Val Arg Arg Asn Arg Leu Asp Leu Thr Leu Glu Pro
225                 230                 235                 240

Ile Tyr Asn Cys Asn Leu Gly Tyr Phe Ala Ala
                245                 250
```

(2) INFORMATION FOR SEQ ID NO:13:

(i) SEQUENCE CHARACTERISTICS:
        (A) LENGTH: 756 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..451

(ix) FEATURE:
        (A) NAME/KEY: misc_feature
        (B) LOCATION: 1..756
        (D) OTHER INFORMATION: /note= "product = Brassica oleracea -continued var. botrytis CAL"

(xi) SEQUENCE DESCRIPTION: SEQ ID NO:13:

```
ATG GGA AGG GGT AGG GTT GAA ATG AAG AGG ATA GAG AAC AAG ATC AAC          48
Met Gly Arg Gly Arg Val Glu Met Lys Arg Ile Glu Asn Lys Ile Asn
 1               5                  10                  15

AGA CAA GTG ACG TTT TCG AAA AGA AGA GCT GGT CTT TTG AAG AAA GCC          96
Arg Gln Val Thr Phe Ser Lys Arg Arg Ala Gly Leu Leu Lys Lys Ala
                20                  25                  30

CAT GAG ATC TCG ATT CTT TGT GAT GCT GAG GTT TCC CTT ATT GTC TTC         144
His Glu Ile Ser Ile Leu Cys Asp Ala Glu Val Ser Leu Ile Val Phe
            35                  40                  45

TCC CAT AAG GGG AAA CTG TTC GAG TAC TCG TCT GAA TCT TGC ATG GAG         192
Ser His Lys Gly Lys Leu Phe Glu Tyr Ser Ser Glu Ser Cys Met Glu
        50                  55                  60

AAG GTA CTA GAA CGC TAC GAG AGG TAC TCT TAC GCC GAG AAA CAG CTA         240
Lys Val Leu Glu Arg Tyr Glu Arg Tyr Ser Tyr Ala Glu Lys Gln Leu
 65                  70                  75                  80

AAA GCT CCA GAC TCT CAC GTC AAT GCA CAA ACG AAC TGG TCA ATG GAA         288
Lys Ala Pro Asp Ser His Val Asn Ala Gln Thr Asn Trp Ser Met Glu
                85                  90                  95

TAT AGC AGG CTT AAG GCT AAG ATT GAG CTT TGG GAG AGG AAC CAA AGG         336
Tyr Ser Arg Leu Lys Ala Lys Ile Glu Leu Trp Glu Arg Asn Gln Arg
            100                 105                 110

CAT TAT CTG GGA GAA GAT TTA GAA TCA ATC AGC ATA AAG GAG CTA CAG         384
His Tyr Leu Gly Glu Asp Leu Glu Ser Ile Ser Ile Lys Glu Leu Gln
        115                 120                 125

AAT CTG GAG CAG CAG CTT GAC ACT TCT CTT AAA CAT ATT CGC TCC AGA         432
Asn Leu Glu Gln Gln Leu Asp Thr Ser Leu Lys His Ile Arg Ser Arg
    130                 135                 140

AAA AAT CAA CTA ATG CAC T AGTCCCTCAA CCACCTCCAA AGAAAGGAGA              481
Lys Asn Gln Leu Met His
145                 150

AAGAAATACT GGAGGAAAAC AGCATGCTTG CCAAACAGAT AAAGGAGAGG GAGAGTATCC       541

TAAGGACACA TCAAAACCAA TCAGAGCAGC AAAACCGCAG CCACCATGTA GCTCCTCAGC       601

CGCAACCGCA GTTAAATCCT TACATGGCAT CATCTCCTTT CCTAAATATG GGTGGCATGT       661

ACCAAGGAGA ATATCCAACG GCGGTGAGGA GGAACCGTCT CGATCTGACT CTTGAACCCA       721

TTTACAACTG CAACCTTGGT TACTTTGCCG CATGA                                  756
```

(2) INFORMATION FOR SEQ ID NO:14:

(i) SEQUENCE CHARACTERISTICS:
      (A) LENGTH: 150 amino acids
      (B) TYPE: amino acid
      (D) TOPOLOGY: linear (ii) MOLECULE TYPE: protein (xi) SEQUENCE DESCRIPTION: SEQ ID NO:14:

```
Met Gly Arg Gly Arg Val Glu Met Lys Arg Ile Glu Asn Lys Ile Asn
 1               5                  10                  15

Arg Gln Val Thr Phe Ser Lys Arg Arg Ala Gly Leu Leu Lys Lys Ala
                20                  25                  30

His Glu Ile Ser Ile Leu Cys Asp Ala Glu Val Ser Leu Ile Val Phe
            35                  40                  45

Ser His Lys Gly Lys Leu Phe Glu Tyr Ser Ser Glu Ser Cys Met Glu
        50                  55                  60

Lys Val Leu Glu Arg Tyr Glu Arg Tyr Ser Tyr Ala Glu Lys Gln Leu
```

```
                65                  70                  75                  80
Lys Ala Pro Asp Ser His Val Asn Ala Gln Thr Asn Trp Ser Met Glu
                        85                  90                  95

Tyr Ser Arg Leu Lys Ala Lys Ile Glu Leu Trp Glu Arg Asn Gln Arg
                100                 105                 110

His Tyr Leu Gly Glu Asp Leu Glu Ser Ile Ser Ile Lys Glu Leu Gln
            115                 120                 125

Asn Leu Glu Gln Gln Leu Asp Thr Ser Leu Lys His Ile Arg Ser Arg
    130                 135                 140

Lys Asn Gln Leu Met His
145                 150

(2) INFORMATION FOR SEQ ID NO:15:

(i) SEQUENCE CHARACTERISTICS:
        (A) LENGTH: 1500 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 72..1343

(ix) FEATURE:
        (A) NAME/KEY: misc_feature
        (B) LOCATION: 1..1500
        (D) OTHER INFORMATION: /note= "product = Arabidopsis
            thaliana LEAFY"

(xi) SEQUENCE DESCRIPTION: SEQ ID NO:15:

AAAGCAATCT GCTCAAAAGA GTAAAGAAAG AGAGAAAAAG AGAGTGATAG AGAGAGAGAG      60

AAAAATAGAT T ATG GAT CCT GAA GGT TTC ACG AGT GGC TTA TTC CGG TGG     110
            Met Asp Pro Glu Gly Phe Thr Ser Gly Leu Phe Arg Trp
              1               5                  10

AAC CCA ACG AGA GCA TTG GTT CAA GCA CCA CCT CCG GTT CCA CCT CCG      158
Asn Pro Thr Arg Ala Leu Val Gln Ala Pro Pro Pro Val Pro Pro Pro
    15                  20                  25

CTG CAG CAA CAG CCG GTG ACA CCG CAG ACG GCT GCT TTT GGG ATG CGA      206
Leu Gln Gln Gln Pro Val Thr Pro Gln Thr Ala Ala Phe Gly Met Arg
30                  35                  40                  45

CTT GGT GGT TTA GAG GGA CTA TTC GGT CCA TAC GGT ATA CGT TTC TAC      254
Leu Gly Gly Leu Glu Gly Leu Phe Gly Pro Tyr Gly Ile Arg Phe Tyr
                50                  55                  60

ACG GCG GCG AAG ATA GCG GAG TTA GGT TTT ACG GCG AGC ACG CTT GTG      302
Thr Ala Ala Lys Ile Ala Glu Leu Gly Phe Thr Ala Ser Thr Leu Val
            65                  70                  75

GGT ATG AAG GAC GAG GAG CTT GAA GAG ATG ATG AAT AGT CTC TCT CAT      350
Gly Met Lys Asp Glu Glu Leu Glu Glu Met Met Asn Ser Leu Ser His
        80                  85                  90

ATC TTT CGT TGG GAG CTT CTT GTT GGT GAA CGG TAC GGT ATC AAA GCT      398
Ile Phe Arg Trp Glu Leu Leu Val Gly Glu Arg Tyr Gly Ile Lys Ala
    95                  100                 105

GCC GTT AGA GCT GAA CGG AGA CGA TTG CAA GAA GAG GAG GAA GAG GAA      446
Ala Val Arg Ala Glu Arg Arg Arg Leu Gln Glu Glu Glu Glu Glu Glu
110                 115                 120                 125

TCT TCT AGA CGC CGT CAT TTG CTA CTC TCC GCC GCT GGT GAT TCC GGT      494
Ser Ser Arg Arg Arg His Leu Leu Leu Ser Ala Ala Gly Asp Ser Gly
                130                 135                 140

ACT CAT CAC GCT CTT GAT GCT CTC TCC CAA GAA GAT GAT TGG ACA GGG      542
```

```
Thr His His Ala Leu Asp Ala Leu Ser Gln Glu Asp Asp Trp Thr Gly
        145                 150                 155

TTA TCT GAG GAA CCG GTG CAG CAA CAA GAC CAG ACT GAT GCG GCG GGG          590
Leu Ser Glu Glu Pro Val Gln Gln Gln Asp Gln Thr Asp Ala Ala Gly
160                 165                 170

AAT AAC GGC GGA GGA GGA AGT GGT TAC TGG GAC GCA GGT CAA GGA AAG          638
Asn Asn Gly Gly Gly Gly Ser Gly Tyr Trp Asp Ala Gly Gln Gly Lys
        175                 180                 185

ATG AAG AAG CAA CAG CAG CAG AGA CGG AGA AAG AAA CCA ATG CTG ACG          686
Met Lys Lys Gln Gln Gln Gln Arg Arg Arg Lys Lys Pro Met Leu Thr
190                 195                 200                 205

TCA GTG GAA ACC GAC GAA GAC GTC AAC GAA GGT GAG GAT GAC GAC GGG          734
Ser Val Glu Thr Asp Glu Asp Val Asn Glu Gly Glu Asp Asp Asp Gly
        210                 215                 220

ATG GAT AAC GGC AAC GGA GGT AGT GGT TTG GGG ACA GAG AGA CAG AGG          782
Met Asp Asn Gly Asn Gly Gly Ser Gly Leu Gly Thr Glu Arg Gln Arg
            225                 230                 235

GAG CAT CCG TTT ATC GTA ACG GAG CCT GGG GAA GTG GCA CGT GGC AAA          830
Glu His Pro Phe Ile Val Thr Glu Pro Gly Glu Val Ala Arg Gly Lys
        240                 245                 250

AAG AAC GGC TTA GAT TAT CTG TTC CAC TTG TAC GAA CAA TGC CGT GAG          878
Lys Asn Gly Leu Asp Tyr Leu Phe His Leu Tyr Glu Gln Cys Arg Glu
        255                 260                 265

TTC CTT CTT CAG GTC CAG ACA ATT GCT AAA GAC CGT GGC GAA AAA TGC          926
Phe Leu Leu Gln Val Gln Thr Ile Ala Lys Asp Arg Gly Glu Lys Cys
270                 275                 280                 285

CCC ACC AAG GTG ACG AAC CAA GTA TTC AGG TAC GCG AAG AAA TCA GGA          974
Pro Thr Lys Val Thr Asn Gln Val Phe Arg Tyr Ala Lys Lys Ser Gly
            290                 295                 300

GCG AGT TAC ATA AAC AAG CCT AAA ATG CGA CAC TAC GTT CAC TGT TAC         1022
Ala Ser Tyr Ile Asn Lys Pro Lys Met Arg His Tyr Val His Cys Tyr
        305                 310                 315

GCT CTC CAC TGC CTA GAC GAA GAA GCT TCA AAT GCT CTC AGA AGA GCG         1070
Ala Leu His Cys Leu Asp Glu Glu Ala Ser Asn Ala Leu Arg Arg Ala
        320                 325                 330

TTT AAA GAA CGC GGT GAG AAC GTT GGC TCA TGG CGT CAG GCT TGT TAC         1118
Phe Lys Glu Arg Gly Glu Asn Val Gly Ser Trp Arg Gln Ala Cys Tyr
335                 340                 345

AAG CCA CTT GTG AAC ATC GCT TGT CGT CAT GGC TGG GAT ATA GAC GCC         1166
Lys Pro Leu Val Asn Ile Ala Cys Arg His Gly Trp Asp Ile Asp Ala
350                 355                 360                 365

GTC TTT AAC GCT CAT CCT CGT CTC TCT ATT TGG TAT GTT CCA ACA AAG         1214
Val Phe Asn Ala His Pro Arg Leu Ser Ile Trp Tyr Val Pro Thr Lys
            370                 375                 380

CTG CGT CAG CTT TGC CAT TTG GAG CGG AAC AAT GCG GTT GCT GCG GCT         1262
Leu Arg Gln Leu Cys His Leu Glu Arg Asn Asn Ala Val Ala Ala Ala
        385                 390                 395

GCG GCT TTA GTT GGC GGT ATT AGC TGT ACC GGA TCG TCG ACG TCT GGA         1310
Ala Ala Leu Val Gly Gly Ile Ser Cys Thr Gly Ser Ser Thr Ser Gly
        400                 405                 410

CGT GGT GGA TGC GGC GGC GAC GAC TTG CGT TTC TAGTTTGGTT TGGGTAGTTG       1363
Arg Gly Gly Cys Gly Gly Asp Asp Leu Arg Phe
        415                 420

TGGTTTGTTT AGTCGTTATC CTAATTAACT ATTAGTCTTT AATTTAGTCT TCTTGGCTAA       1423

TTTATTTTTC TTTTTTTGTC AAAACCTTTA ATTTGTTATG CTAATTTGT  TATACACGCA       1483

GTTTTCTTAA TGCGTTA                                                     1500

(2) INFORMATION FOR SEQ ID NO:16:
```

(i) SEQUENCE CHARACTERISTICS:
  (A) LENGTH: 424 amino acids
  (B) TYPE: amino acid
  (D) TOPOLOGY: linear (ii) MOLECULE TYPE: protein (xi) SEQUENCE DESCRIPTION: SEQ ID NO:16:

```
Met Asp Pro Glu Gly Phe Thr Ser Gly Leu Phe Arg Trp Asn Pro Thr
 1               5                  10                  15

Arg Ala Leu Val Gln Ala Pro Pro Val Pro Pro Leu Gln Gln
             20                  25                  30

Gln Pro Val Thr Pro Gln Thr Ala Ala Phe Gly Met Arg Leu Gly Gly
             35                  40                  45

Leu Glu Gly Leu Phe Gly Pro Tyr Gly Ile Arg Phe Tyr Thr Ala Ala
     50                  55                  60

Lys Ile Ala Glu Leu Gly Phe Thr Ala Ser Thr Leu Val Gly Met Lys
 65                  70                  75                  80

Asp Glu Glu Leu Glu Glu Met Met Asn Ser Leu Ser His Ile Phe Arg
                 85                  90                  95

Trp Glu Leu Leu Val Gly Glu Arg Tyr Gly Ile Lys Ala Ala Val Arg
                100                 105                 110

Ala Glu Arg Arg Arg Leu Gln Glu Glu Glu Glu Glu Ser Ser Arg
             115                 120                 125

Arg Arg His Leu Leu Leu Ser Ala Ala Gly Asp Ser Gly Thr His His
         130                 135                 140

Ala Leu Asp Ala Leu Ser Gln Glu Asp Asp Trp Thr Gly Leu Ser Glu
145                 150                 155                 160

Glu Pro Val Gln Gln Gln Asp Gln Thr Asp Ala Ala Gly Asn Asn Gly
                 165                 170                 175

Gly Gly Gly Ser Gly Tyr Trp Asp Ala Gly Gln Gly Lys Met Lys Lys
             180                 185                 190

Gln Gln Gln Gln Arg Arg Arg Lys Lys Pro Met Leu Thr Ser Val Glu
         195                 200                 205

Thr Asp Glu Asp Val Asn Glu Gly Glu Asp Asp Gly Met Asp Asn
    210                 215                 220

Gly Asn Gly Gly Ser Gly Leu Gly Thr Glu Arg Gln Arg Glu His Pro
225                 230                 235                 240

Phe Ile Val Thr Glu Pro Gly Glu Val Ala Arg Gly Lys Lys Asn Gly
                 245                 250                 255

Leu Asp Tyr Leu Phe His Leu Tyr Glu Gln Cys Arg Glu Phe Leu Leu
             260                 265                 270

Gln Val Gln Thr Ile Ala Lys Asp Arg Gly Glu Lys Cys Pro Thr Lys
         275                 280                 285

Val Thr Asn Gln Val Phe Arg Tyr Ala Lys Lys Ser Gly Ala Ser Tyr
    290                 295                 300

Ile Asn Lys Pro Lys Met Arg His Tyr Val His Cys Tyr Ala Leu His
305                 310                 315                 320

Cys Leu Asp Glu Glu Ala Ser Asn Ala Leu Arg Arg Ala Phe Lys Glu
                 325                 330                 335

Arg Gly Glu Asn Val Gly Ser Trp Arg Gln Ala Cys Tyr Lys Pro Leu
             340                 345                 350

Val Asn Ile Ala Cys Arg His Gly Trp Asp Ile Asp Ala Val Phe Asn
         355                 360                 365
```

```
Ala His Pro Arg Leu Ser Ile Trp Tyr Val Pro Thr Lys Leu Arg Gln
    370                 375                 380

Leu Cys His Leu Glu Arg Asn Asn Ala Val Ala Ala Ala Ala Ala Leu
385                 390                 395                 400

Val Gly Gly Ile Ser Cys Thr Gly Ser Ser Thr Ser Gly Arg Gly Gly
                405                 410                 415

Cys Gly Gly Asp Asp Leu Arg Phe
            420
```

(2) INFORMATION FOR SEQ ID NO:17:

(i) SEQUENCE CHARACTERISTICS:
        (A) LENGTH: 4379 base pairs
        (B) TYPE: nucleic acid
        (C) STRANDEDNESS: double
        (D) TOPOLOGY: linear (ix) FEATURE:
        (A) NAME/KEY: unsure
        (B) LOCATION: 2095..2098
        (D) OTHER INFORMATION: /note= "N = one or more
            nucleotides."

(ix) FEATURE:
        (A) NAME/KEY: misc_feature
        (B) LOCATION: 1..4379
        (D) OTHER INFORMATION: /note= "sequence = Arabidopsis
            thaliana AP1 gene"

(xi) SEQUENCE DESCRIPTION: SEQ ID NO:17:

```
GAATTCCCCG GATCTCCATA TACATATCAT ACATATATAT AGTATACTAT CTTTAGACTG     60

ATTTCTCTAT ACACTATCTT TTAACTTATG TATCGTTTCA AAACTCAGGA CGTACATGTT    120

TTAAATTTGG TTATATAACC ACGACCATTT CAAGTATATA TGTCATACCA TACCAGATTT    180

AATATAACTT CTATGAAGAA AATACATAAA GTTGGATTAA AATGCAAGTG ACATCTTTTT    240

AGCATAGGTT CATTTGGCAT AGAAGAAATA TATAACTAAA AATGAACTTT AACTTAAATA    300

GATTTTACTA TATTACAATT TTTCTTTTTA CATGGTCTAA TTTATTTTTC TAAAATTAGT    360

ATGATTGTTG TTTTGATGAA ACAATAATAC CGTAAGCAAT AGTTGCTAAA AGATGTCCAA    420

ATATTTATAA ATTACAAAGT AAATCAAATA AGGAAGAAGA CACGTGGAAA ACACCAAATA    480

AGAGAAGAAA TGGAAAAAAC AGAAAGAAAT TTTTTAACAA GAAAAATCAA TTAGTCCTCA    540

AACCTGAGAT ATTTAAAGTA ATCAACTAAA ACAGGAACAC TTGACTAACA AAGAAATTTG    600

AAATGTGGTC CAACTTTCAC TTAATTATAT TATTTTCTCT AAGGCTTATG CAATATATGC    660

CTTAAGCAAA TGCCGAATCT GTTTTTTTTT TTTGTTATTG GATATTGACT GAAAATAAGG    720

GGTTTTTTCA CACTTGAAGA TCTCAAAAGA GAAAACTATT ACAACGGAAA TTCATTGTAA    780

AAGAAGTGAT TAAGCAAATT GAGCAAAGGT TTTTATGTGG TTTATTTCAT TATATGATTG    840

ACATCAAATT GTATATATAT GGTTGTTTTA TTTAACAATA TATATGGATA TAACGTACAA    900

ACTAAATATG TTTGATTGAC GAAAAAAAAT ATATGTATGT TTGATTAACA ACATAGCACA    960

TATCAACTGA TTTTTGTCCT GATCATCTAC AACTTAATAA GAACACACAA CATTGAAAAA   1020

ATCTTTGACA AAATACTATT TTTGGGTTTG AAATTTTGAA TACTTACAAT TATCTTCTCG   1080

ATCTTCCTCT CTTTCCTTAA ATCCTGCGTA CAAATCCGTC GACGCAATAC ATTACACAGT   1140

TGTCAATTGG TTCTCAGCTC TACCAAAAAC ATCTATTGCC AAAAGAAAGG TCTATTTGTA   1200

CTTCACTGTT ACAGCTGAGA ACATTAAATA TAATAAGCAA ATTTGATAAA ACAAAGGGTT   1260

CTCACCTTAT TCCAAAAGAA TAGTGTAAAA TAGGGTAATA GAGAAATGTT AATAAAAGGA   1320
```

```
AATTAAAAAT AGATATTTTG GTTGGGTTCA GATTTTGTTT CGTAGATCTA CAGGGAAATC    1380

TCCGCCGTCA ATGCAAAGCG AAGGTGACAC TTGGGGAAGG ACCAGTGGTC GTACAATGTT    1440

ACTTACCCAT TTCTCTTCAC GAGACGTCGA TAATCAAATT GTTTATTTTC ATATTTTTAA    1500

GTCCGCAGTT TTATTAAAAA ATCATGGACC CGACATTAGT ACGAGATATA CCAATGAGAA    1560

GTCGACACGC AAATCCTAAA GAAACCACTG TGGTTTTTGC AAACAAGAGA AACCAGCTTT    1620

AGCTTTTCCC TAAAACCACT CTTACCCAAA TCTCTCCATA AATAAAGATC CGAGACTCA    1680

AACACAAGTC TTTTTATAAA GGAAAGAAAG AAAAACTTTC CTAATTGGTT CATACCAAAG    1740

TCTGAGCTCT TCTTTATATC TCTCTTGTAG TTTCTTATTG GGGTCTTTG TTTTGTTTGG    1800

TTCTTTTAGA GTAAGAAGTT TCTTAAAAAA GGATCAAAAA TGGGAAGGGG TAGGGTTCAA    1860

TTGAAGAGGA TAGAGAACAA GATCAATAGA CAAGTGACAT TCTCGAAAAG AAGAGCTGGT    1920

CTTTTGAAGA AAGCTCATGA GATCTCTGTT CTCTGTGATG CTGAAGTTGC TCTTGTTGTC    1980

TTCTCCCATA AGGGGAAACT CTTCGAATAC TCCACTGATT CTTGGTAACT TCAACTAATT    2040

CTTTACTTTT AAAAAAATCT TTTAATCTGC TACTTTATAT AGTTTTTTTC CCCCNNNNGG    2100

TCTATGATTC ATACTGTTTT GTTATTATAA AGGTATCATA GAGATCGGTA CTTGATTTGT    2160

TATAGGAAAT CTTGGTTTAA TTGCATAAAA CCATCATTAG ATTTATCCTA AAATGTGATG    2220

ATATTTTGGT CACATCTCCA TATTATTTAT ATAATAAAAT GATAATTGGT TGATGATAAA    2280

GCTAACCCTA ATTCTGTGAA ATGATCAGTA TGGAGAAGAT ACTTGAACGC TATGAGAGGT    2340

ACTCTTACGC CGAAAGACAG CTTATTGCAC CTGAGTCCGA CGTCAATGTA TTTCAATAAA    2400

TATTTCTCCT TTTAATCCAC ATATATATTA TATCAATCTA TTTGTAGTAT TGATGAATTT    2460

TATTTGTATA AAACTTCTGG TACACAGACA AACTGGTCGA TGGCGTATAA CAGGCTTAAG    2520

GCTAAGATTG AGCTTTTGGA GAGAAACCAG AGGTACACAT TTACACTCAT CACATTTCTA    2580

TCTAGAAAAT CGATCGGGTT CCATTTTAAA GTAAGTTAAA ATTCATTGAT GCTATTGAAA    2640

TTCAGGCATT ATCTTGGGGA AGACTTGCAA GCAATGAGCC CTAAAGAGCT TCAGAATCTG    2700

GAGCAGCAGC TTGACACTGC TCTTAAGCAC ATCCGCACTA GAAAAGTATT GCCTTCTGCT    2760

ATTTCGTTGA ACATATCTAT ATAACTTAAA CGTTTACAAG TGTTATTATA ATGTGAACAT    2820

TGAAATACAT ATGTGTATGT ATCAATATAT ATATCAGTAA TCAATATCAA TTTGATATGT    2880

CTATAGGTTG GTTCGAATGT ATGAGTTATG TTGTGTATTT TAAGACTCCA TATTACTTAA    2940

AGTAATGGGT TGTTAATGTT GATGTGTGTG TATGCAGAAC CAACTTATGT ACGAGTCCAT    3000

CAATGAGCTC CAAAAAAAGG TATGTAAAAC CCCTATCAAA TGTATGTCTT ATAGAGAAAC    3060

GTATAGGAAA GCTAATTAAC AATCGTGCCG TTTCGGAATG ACAGGAGAAG GCCATACAGG    3120

AGCAAAACAG CATGCTTTCT AAACAGGAAC ACATGTCATC ATTTCTCTTT CATCAACATG    3180

TTGTCCATTG CATTACTGTT ACCTTCCACT GTTCTGCTCC ACACTTCCAG CCAAGCTATA    3240

CCTACGATAT CTTCATATCT CCACTTAACT TCGGCACCAT TAAATAAAAA TAGAAAATCT    3300

TTGCAAATTT GTTTGAAATA GCATAGATGT TGTCTATTGA TTGATATAAT CACCAGCCTG    3360

TACGTAGATA TGGTTTGTCC GTTAGTTTTT AAGGTGTCTC TCGGATTGAA AATATTTTGA    3420

AATCTTTTGA AATGTTTGTC CCATCATTCT TACTTAGCTC ATATCTATGT ATATGAATAT    3480

AGACACTACT CCTAATTATA AAATGTTATA ATAGTTCATT GCATGAGTGC AACTGTGAAA    3540

ATAACTATTT GTAACCATTG CATATATATA GTTTCTTCAC TTTGAAAATT GATGATGATA    3600

ATATGGTTTG AAATAAATTT GCTGGCAGAT CAAGGAGAGG GAAAAAATTC TTAGGGCTCA    3660

ACAGGAGCAG TGGGATCAGC AGAACCAAGG CCACAATATG CCTCCCCCTC TGCCACCGCA    3720
```

```
GCAGCACCAA ATCCAGCATC CTTACATGCT CTCTCATCAG CCATCTCCTT TTCTCAACAT      3780

GGGGTAACAA AAAATTACTA ATCAGTCTTA ATTTAAAGCA CATATGTTAT GCAAGCTAGT      3840

TACGTTAGGT GTTGTAATTT CATTGAAGTT ATAGCTGTTA GTGATGGTTA CATGATGCTA      3900

GATTTTGAAA CTAGAAAACT TTATTTTAAA ACATTATTTT ATTAACGTAG GTTAATGCAA      3960

TGGTCGCCAA ACGAACAAAC TTATTAGTGT GGAAAAATGT ACATGGAATG GTTGCGAAAA      4020

GCCTAAGTCG ACTTTTGTTG TTGTTGGTCT ATGTGTTTAA GTACAATTTT AGTTTGTTAG      4080

ATAAATGAAA TTAATATATC TTTGACATTT CACAATGGAC TGATATTTGA TTTTCCTTTG      4140

TTGTACGGTG AAACATATGA TTACATATGC ACTTTCATAT ATATCCTATG TATGATTGTG      4200

AATGCAGTGG TCTGTATCAA GAAGATGATC CAATGGCAAT GAGGAGGAAT GATCTCGAAC      4260

TGACTCTTGA ACCCGTTTAC AACTGCAACC TTGGCCGTTC GCCGCATGAA GCATTTCCAT      4320

ATATATATAT TTGTAATCGT CAACAATAAA AACTAGTTTG CCATCATACA TATAAATAG      4379

(2) INFORMATION FOR SEQ ID NO:18:

(i) SEQUENCE CHARACTERISTICS:
        (A) LENGTH: 1865 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: unsure
        (B) LOCATION: 1077..1081
        (D) OTHER INFORMATION: /note= "N = one or more
            nucleotides."

(ix) FEATURE:
        (A) NAME/KEY: misc_feature
        (B) LOCATION: 1..1865
        (D) OTHER INFORMATION: /note= "sequence = Brassica
            oleracea AP1 gene"

(xi) SEQUENCE DESCRIPTION: SEQ ID NO:18:

GCACCTGAGT CCGACTCCAA TGTAAACCAA TTTCTCTCCA TTAACTTATA TAAATTAAAT       60

ATTATTTCAG TATTAGTGAT ATATACTTAT CTGTATTAAA CTTGTGAGAT ATAGACGAAC      120

TGGTCGATGG AGTATAATAG GCTTAAGGCT AAGATTGAGC TTTTGGAGAG AAACCAGAGG      180

TACATTTTCA TTCATCATTT ATATTAATAG ATGAAATATC AAACAGGATT AATGTTAGTT      240

AAAAATGCAT GATTACTTAT AAGAAAATGA TGCATTTAAA TAACAAAAAA ATGCATCGAT      300

GCTCTATTGA AATTTAGGCA CTATCTTGGG GAAGACTTGC AAGCAATGAG CCCTAAGGAA      360

CTCCAGAATC TAGAGCAACA GCTTGATACT GCTCTTAAGC ACATCCGCTC TAGAAAAGTA      420

TGAATCCTCC TATTTCTTTA ATTAACATGT ATACAACTTA AACACATATT ATTTTATTAT      480

TCAATACATA TATATGAATA GTACATATGT GATTTTATTG GTTGGATATA AAAGATCAAT      540

CACGTCGATT AGATGTATGA CTTTTTAAAG AATTAGTATA TAGAGTATGA TTAGTCAATG      600

TAATGGTACG TACGTTTATG CAGAACCAAC TTATGTACGA CTCCATCAAT GAGCTCCAAA      660

GAAAGGTATG TATAAACCCT ATCAAATTGA CGTTTACATA GAATAACTGC GTGTAAGAAT      720

CCTATAGGGG AGCTAACAAT CGTGCCGTTT TGGAAATGAC AGGAGAAAGC CATACAGGAA      780

CAAAACAGCA TGCTTTCCAA GCAGGTGCCA TTTGTCATTA TTTTTATATC GTCAAAATGT      840

TTTCTATTGT AGTACTGTTA GCTTCCACTG TTCTACTCCA CACTTCAAGC CAAGCTATAC      900

CTACCTACGA CTACGAGATT CTCCACATAT TTCTCCACTT AGCTTCGGCA CCACTATAAC      960
```

```
TAAAATATAG ATAAAATATC ATTTTTATAG TCTATGATTG ATATACTCGT CAGCCAGTAC    1020

GTAGTTGGGT ATTTGCCCGT TTAGTTTTAA GGTTCTTTTC CGGATTGAAA ATATTTNNNN    1080

NACCCTACCT TTGATGCTAT TATATGTATA TCTATTTAGA AGTCGTGGCT TTGAAAATTG    1140

ATGATGATAT GTATGGTATA AGTTGGTAAC AAACTGGTGT GTGAAATTGA AACTTGTCAG    1200

ATTAAGGAGA GGGAAAACGT TCTTAGGGCG CAACAAGAGC AATGGGACGA GCAGAACCAT    1260

GGCCATATAT GCCTCCGCCT CCACCCCCGC AGCAGCATCA AATCCAGCAT CCTTACATGC    1320

TCTCTCATCA GCCATCTCCT TTTCTCAACA TGGGGTAGTT AAAAATTCGT TCCTCTTACT    1380

TTCAAGTCAT ATGTGTATAT ATACAAGATA GTTAGGTGTT ATAAGTCCAG TGAGTTAGGT    1440

TGTGTTAGTG ATGGTTAGAT GTCTAGATTG TGAATTACAA GTACTAAGAT TTTTCAGTTA    1500

TATAATTAAC GTATTGATCA TCAATCAAAT GGTCGTAAAA AAACAGACTT ATATTTTTGG    1560

GAAAGTAGAT GGAATGGCTG CTAAAAGTCT AAGAAACCTT TGGGAGCAGG TCGTATTTAT    1620

TGTTGTTCAA ATTAAACTTG AGGTAGTTAG ATAAATAAAC TATCTTTGAT ATGGCCTTTA    1680

CCAATTTCAC TACAAAACAT GTGATATTTT CAGCACCTAT GTAGATAATT TGTAAGCTAT    1740

ATCATGTGCA TATGAATGTA AATGCAGGGG GCTGTATCAA GAAGAAGATC AAATGGCAAT    1800

GAGGAGGAAC GATCTCGATC TGTCTCTTGA ACCCGGTTAC AACTGCAACC TTGGCCGTCG    1860

CCGCT                                                               1865

(2) INFORMATION FOR SEQ ID NO:19:

(i) SEQUENCE CHARACTERISTICS:
        (A) LENGTH: 2185 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: unsure
        (B) LOCATION: 295..297
        (D) OTHER INFORMATION: /note= "N = one or more
            nucleotides."

(ix) FEATURE:
        (A) NAME/KEY: unsure
        (B) LOCATION: 1389..1391
        (D) OTHER INFORMATION: /note= "N = one or more
            nucleotides."

(ix) FEATURE:
        (A) NAME/KEY: misc_feature
        (B) LOCATION: 1..2185
        (D) OTHER INFORMATION: /note= "sequence = Brassica
            oleracea var. botrytis AP1 gene"

(xi) SEQUENCE DESCRIPTION: SEQ ID NO:19:

GAGCTCTTCT TTATATCTCT TCTTGTAGTT TCTTGTTTCG TTTGGTTCTC TTAGAGGAAA      60

TAGTTCCTTT AAAAGGGATA AAAATGGGAA GGGGTAGGGT TCAGTTGAAG AGGATAGAAA     120

ACAAGATCAA TAGACAAGTG ACATTCTCGA AAAGAAGAGC TGGTCTTATG AAGAAAGCTC     180

ATGAGATCTC TGTTCTGTGT GATGCTGAAG TTGCGCTTGT TGTCTTCTCC CATAAGGGGA     240

AACTCTTTGA ATACCCCACT GATTCTTGGT AACTTTCTCA TTTAAGAAAC AAAANNNTAC     300

CCTAAGATTG TATTTTACAT GATCATTTAC TTGTTTTACA CAGTATATAC TCTATGTATA     360

TAATATGATC ATAAATTGTT GATGATAAGA AGCTAGCCCT AATTCTGTGA ATTGAACAGT     420

ATGGAGGAGA TACTTGAACG CTATGAGAGA TACTCTTACG CCGAGAGACA GCTTATAGCA     480
```

```
CCTGAGTCCG ACTCCAATGT AAACCAATTT CTCTCCATTA ACTTATATAA ATTAAATATT      540

ATTTCAGTAT TAGTGATATA TACTTATCTG TATTAAACTT GTGAGATATA GACGAACTGG      600

TCGATGGAGT ATAATAGGCT TAAGGCTAAG ATTGAGCTTT TGGAGAGAAA CCAGAGGTAC      660

ATTTTCATTC ATCATTTATA TATATGATGA AATATCAAAC AGGATTAATG TTAGTTAAAA      720

ATGCATGATT ACTTATAAAA AAATGATGCA TTTAAATAAC AAAAAAATGC ATCGATGCTC      780

TATTGAAATT TAGGCACTAT CTTGGGGAAG ACTTGCAAGC AATGAGCCCT AAGGAACTCC      840

AGAATCTAGA GCAACAGCTT GATACTGCTC TTAAGCACAT CCGCTCTAGA AAAGTATGAA      900

TCCTCCTATT TCTTTAATTA ACATGTATAC AACTTAAACA CATATTATTT TATTATTCAA      960

ATACATATAT ATAAATAGTA CATATGTGAT TTTATTGGTT GGATTTGAAA AGATCAATCA     1020

CGTCGATTAG AATGTATGAC TTTTTAAAGA ATTAGTATAT AGAGTATGAT TAGTCAATGT     1080

AATGGATCGT TTATGCAGAA CCAACTTATG TACGACTCCA TCAATGAGCT CCAAAGAAAG     1140

GTATGTATAA ACCCTATCAA ATTGACGTTT ACATAGAATA ACTGCGTGTA AGAATCCTAT     1200

AGGGGAGCTA AAAATCGTGC CGTTTTGGAA ATGACAGGAG AAAGCCATAC AGGAACAAAA     1260

CAGCATGCTT TCCAAGCAGG TGCCATTTGT CATTATTTTT ATTTCGTCAA AATGTTTTCT     1320

ATTGTAGATC TGTTAGCTTC CACTGTTCTC ACCACACTTC AAGCCAAGCT ATACCTACCT     1380

ACGACTACNN NCCTACATTT GATGCTATTT ATATGTATAT CTATTTAGAA GTCGTGGCTT     1440

TGAAAATTGA TGATGATATG GTATGGTATA AGTTGGTAAC AAACTGGTGT GTGAAATTGA     1500

AACTTGTCAG ATTAAGGAGA GGGAAAACGT TCTTAGGGCG CAACAAGAGC AATGGGACGA     1560

GCAGAACCAT GGCCATAATA TGCCTCCGCC TCCACCCCCG CAGCAGCATC AAATCCAGCA     1620

TCCTTACATG CTCTCTCATC AGCCATCTCC TTTTCTCAAC ATGGGGTAGT TAAAAATTCG     1680

TTCCTCTTAC TTTCAAGTAC ATATGTGTTA TATATACAAG ATAGTTAGGT GTTATAAGTC     1740

CAGTGAGTTA AGTTGTGTTA GTGATGGTTA GATGTCTAAA TTGTGAAATA CAAGTACTAA     1800

GATTTTTCAT GTATATATTT AAACGTATTA ATCATCAATC AAATGGTCGT AAAAGAAACA     1860

GACTTATATT TTTGGGAAAA GTAGATGGAA TGGCTGCTAA AAGTCTAAGA AACCTTTGGG     1920

AGCAGGTCGT TTTTATTGTT GTTCAAATTA AACTTGAGGT AGTTAGATAA ATAAACTATC     1980

TTTGATATGG GCCTTTACCA ATTTCACTAC AAAACATGTG ATATTTTCAG CACCTATGTA     2040

GATAATTTTG TAAGCTATAT CATGTGCATA TGAATGTAAA TGTAGAGGGC TGTATCAAGA     2100

AGAAGATCAA ATGGCAATGA GGAGGAACGA TCTCGATCTG TCTCTTGAAC CCGTTTACAA     2160

CTGCAACCTT GGCCGTCGCT GCTGA                                          2185

(2) INFORMATION FOR SEQ ID NO:20:

(i) SEQUENCE CHARACTERISTICS:
          (A) LENGTH: 5855 base pairs
          (B) TYPE: nucleic acid
          (C) STRANDEDNESS: double
          (D) TOPOLOGY: linear (ii) MOLECULE TYPE: DNA (genomic)

(ix) FEATURE:
          (A) NAME/KEY: misc_feature
          (B) LOCATION: 1..5855
          (D) OTHER INFORMATION: /note= "sequence = Arabidopsis
              thaliana CAL gene"

(xi) SEQUENCE DESCRIPTION: SEQ ID NO:20:

GGATCCCTCC GGAAGCCTTA GATCAATGGT AGTTGTGGTT ATTTTAAGAT CAGATTCTTT       60
```

-continued

| | |
|---|---|
| TGGAAATCCA GTAACATAGT CTGGGAATAT GATTTGCTTG TTGGTCACCG TTACTGCTTC | 120 |
| TGCGTTCGTC ATTTCCGATT TTACGTACTT TTGATCACTA TGATAATTTC TTCTTTCTTA | 180 |
| CGTCGAGATG TGTCTGCTTT TTGTAGATTG AATTTCTCAA TGTTGCTTTG ATCATAAGAC | 240 |
| CATTTGATTT CTTTCCTTCA TTGATCGATC CAATTTCTTC GGGAGATAAA TAAGGTAAAA | 300 |
| ATGGACTATT ATTTTTGGAA AATACAGGAG AAAAAAATTC TTAAGAATAA AAGAGTATTT | 360 |
| ATAGTGACCA TGAATTTTGT TGTTTTTTTA AAAAGAAAAA AAAACTCGAT TGGATTGGAT | 420 |
| GACACATTGA AATTAACATT CAAATAGCAT CTTAGTTAAC AGATATTGCA TGCACCATAT | 480 |
| AATAAAATAT CATAATTATG TGTGATGCGA GGTTTGTTTT GGTCAAAATG TTATTTTAAT | 540 |
| CACAATTTAA TAACAGATCA TTTACCAATT TGTTTTTTGA TAATTTATGC CAACTTAGTA | 600 |
| AATTCATCCA AAAGTTGAA AAATATAGAT GTGTAATATG TTGACGGATA TACAACACTC | 660 |
| AAAACAATAT ACTCAAAAAA AAAAAAAATT GAAAGCGGCA ACGATTCAAA CATATATGCT | 720 |
| AAATTTTAAT AATGGACAAA GGAGGAAGTA CTGCATATGT ACGAAAAGTG TTGATAATGG | 780 |
| AGAGCAGCGG ATAGTGTCGC CAAGGGCACG AGCTTTAGAT TCTTTTAGTT TGCTCTAAAT | 840 |
| GTTCTTCTTT GGTACTTTTA ATTGCTTTAG TTGCTTGCTT CTTATCTCCA CATAAATAAA | 900 |
| TGGGGTAACC ATTTTCTCTC GTATCTTATT CCGATCTTTG GATCTATGTA CGTACTACAT | 960 |
| GAATAAATCG TGTTCAATAA GTTATTATCA TTTGGTCTGC TTAAAGTGAT CATGGTGTAT | 1020 |
| TAATCTATAA TACGTAGTTC TCTTAATTTA TTCCCTAGAA TTCCATCAAA GACAAATTTT | 1080 |
| AGCAAAAAGA AAAGTTGAGT ATATAATTTG CTTAGTAGTA CAAAAAAAAA CTTTATGGTA | 1140 |
| ATTTGTATTT TGGATATTTC CTTNATTAAC CCAAACTTCA AAATTAATTT TCTTCTGCTG | 1200 |
| TATCTTTATA TCCAACGTGA AATCTATTGA CTCAACAAAA TACACAGTTG TCAATTGAAG | 1260 |
| TTCAACTCTA CCAAGAAACA TCTATATGTA CTTCACTGTT CTTACCGCCG AGCAATTAAA | 1320 |
| ACCTCTATAA CTACTTGGTT ACATTATTAC ATTTTTATTT ACAAAAAATA TATATCAACA | 1380 |
| ACCAATAATA TAGTTAGAAA ATGAAAGAAA ATTATTTAAG AAATATCCGC CGTCAATGCA | 1440 |
| AATCGAATGC GACACTTGGG GAAGCTCTGA AGTCTGTGGT CTGTGCATAT TTCACTTGTC | 1500 |
| TAGCTAACCC ATTTTCACGT CACTAGACGT CGATAATCAA TTATTGTTAT TTTTTTTATC | 1560 |
| AATGTTCCAC TTATTGAAAA TTATATACGA GAAAACATAG ACTCGACATT AGGCAATGGA | 1620 |
| AGTCTAATCA GACCAATGAG AAGTCGACAA CACATCCTAG AAACCAACTC TGGTTTATTT | 1680 |
| CCTTCCCTAA TACCAAGTTA TAGNNTTCTT TCAAACCGCT ATTTCCAAAA TATCTCTTCT | 1740 |
| TTAAATAAAG AGTGAAAGAA GCACTCTTTC ACATTACCAT CATTAGAAAA CTTTCCTAAT | 1800 |
| TAGATCAAGA TCGTCGTTAT CTCTCTTGTT TTTTCTTCAT ATAATTTAGT TATTTTAAGA | 1860 |
| GAAATGGGAA GGGGTAGGGT TGAATTGAAG AGGATAGAGA ACAAGATCAA TAGACAAGTG | 1920 |
| ACATTCTCGA AAAGAAGAAC TGGTCTTTTG AAGAAAGCTC AGGAGATCTC TGTTCTTTGT | 1980 |
| GATGCCGAGG TTTCCCTTAT TGTCTTCTCC CATAAGGGCA AATTGTTCGA GTACTCCTCT | 2040 |
| GAATCTTGGT AATTGCTTAA TTCCTTCTTT TTTTAATGTT ATTTTTAGTG TGCCTTCGTT | 2100 |
| TGCCCTAACT AGTAGTCTTT GTTCTACTTA AGGCATATTT TCTGTGTCTT CTATGCTATT | 2160 |
| ATCTGTCTTT GCTGAAAATT TGCCACTGAT TTGGTATCTA TTTACTTGGG ATCTACGAAC | 2220 |
| TGATTGTGTT GGTCATATCA TTAGTTTATT TTTATCAATA ATTTATTATA TATCAAAGAA | 2280 |
| AATGAAATTT TTTAGGACTT TTAGTGAACC CTACAATACG ATCTACTTAA TTATAGTGGC | 2340 |
| ATGGATTTGT AAGAAATCTT CAGCATCTTC TTTAATCTGG AAATGTACAT TTGCTTCAA | 2400 |

```
GTCAAGTTTA GTATATTAGG TACAGAAAGA ACGGATGTTT ATGGTCTAGA CTAGGGTTTT   2460

TGCTTTTAGG AAAGCTATAC TTTTGCTTAA ATATCTTTAA GTTGCATTTT ATGAACACAC   2520

ACACACATAT ATATATATAT ATATTAGTAT ACCAATAATC TTAATTAAGT TTAGAAAGAA   2580

ACTCTTCATT TTTTCCCATT TAATAATGGT TTATAGCTAG GTATAGAGAA ACTGGAAATA   2640

AGTATGTGAC ATCAAGTAT GGGGAGTCTT TGACCTCTGG GGATTAATGT AAAACAGATC    2700

GTTCTTTTTT TTCTAAACAG TTCCTCCGTA CTGATGGTCA AACTTAACTT CAACAGTTCC   2760

TTTTAAACTT TTATAGGGTG CTTGAATACG TCTTGGGGTG TGGGGTTAGT GGCTCAACTG   2820

GTTTATTTAT TTTTAAAAAT GGTAGAAATC AGTACTGTTT CTAGCTAGGG TTTAGGCACA   2880

AAACTAGAGA TCATCTTTAT TCCATAATAG AAAGGAAGAA ACTAATGTTT AATGACATAG   2940

ATTAATTAGA TAACCCTACA TAATCAGATG CTATATGTTA TCACATATTT TGGGTGAATC   3000

GTTAATTACG TTTGAAACAA GTGGCCTCTT GTGCTAGCTG ATAAGATAGT TGNGTATGCA   3060

ATTATATTGG TGGTTGAATC CAAACTAATT CTAACTCGTA AGCTTAATAT TTGTAGCATG   3120

GAGAAGGTAC TAGAACGCTA CGAGAGGTAT TCTTACGCCG AGAGACAGCT GATTGCACCT   3180

GACTCTCACG TTAATGTATG TTTAATGGTC TCCATCATAT ATTTGTGTAT ATTTTGAATC   3240

TTGCATGTGT TTTAACATAG CATATAACTG ATTATTGGCT TTCATGTTGG AAATTAATTG   3300

TGAAGGCACA GACGAACTGG TCAATGGAGT ATAGCAGGCT TAAGGCCAAG ATTGAGCTTT   3360

TGGAGAGAAA CCAAAGGTAC ATAGTACATT TAAATTTATT GTAGTAGTTA AATATTGAGG   3420

AATAACAGAA GAGAGAATGT TCTTAATTAA CTAAATCATC ATAGGCATTA TCTGGGAGAA   3480

GAGTTGGAAC CAATGAGCCT CAAGGATCTC CAAAATCTGG AGCAGCAGCT TGAGACTGCT   3540

CTTAAGCACA TTCGCTCCAG AAAAGTGTGT AAATATATCC CACACTCTAT CTCTATGCAT   3600

AACTAACTTT GACTTTGTGT GGATGTATTA CATATAGTCA AATATTGTAT AGAGATTGTC   3660

TCATATAAAT AAATAATTTT TGGCCTTTTT GTATGCAGAA TCAACTCATG AATGAGTCCC   3720

TCAACCACCT CCAAAGAAAG GTAGCTAAGT TAAAACCATT TTATCTCTCA AGTCCTGTGT   3780

GTATAGAGTC ATGACTTATA TGTTAGAGAT ATAAATCTTT TAATAAATAA ATAACATATA   3840

GGTTATATAT AATTCAGGTT AATATATTAT TAATTACTAG ATGTATATAT ACTTATATAG   3900

ATCATATAAA AAGAGAAATT GACAATGGTG TCATTTTTGT GGAAATGACA GGAGAAGGAG   3960

ATACAGGAGG AAAACAGCAT GCTTACCAAA CAGGTGATCA TTGTTTTTTG CATTTCTAAC   4020

TGTTTCACTA TTTACAATTC CACTGTTGAA CTCCACTTCA ATCTCTACCT TAACGTACCA   4080

TCTCTCCACT TTCGGCCCCA ACTCTTTTGA GTAAAAAGAA TTGATATGTA GTTTCTTTTG   4140

ATTGGTATAA TCATGAGCCT AGCTGCACGT ATAGGTAAGC TTTGTCCGTT TAGTATTAAG   4200

GTTGTCTCCC AGATTTGAAC TTGAACTTGA ACTGTCTTCT CATAATCATA GTCTATGTGT   4260

AAATTACACA TACATTAGCT AGATAGCTAG GAGCTATATT TTAAGTTTTA TTGAGAAGTA   4320

AGAAAACGTA CGATGAAACT ACTTGATTAA GAACATATAT TAAATGAAAA AATATCACAA   4380

TAGTAAGACC TTGACGACGC TAAAATTCGC TTAACATTTT GCAGATTTAA TTATTACTTT   4440

GCATTTGTT TGAAAATATC ATATTACAAA AAAAAGTATA AGAATAAAAA ATTGAAGTTC    4500

CTTGAATAAA TGCAAATAGC TGATTAGTTG CAAATGGGAA TCTATATAAC GATGATGCTT   4560

ATATCATTTT CTTGGCGTGT GTAATCGGTA TAGATAAAGG AGAGGGAAAA CATCCTAAAG   4620

ACAAAACAAA CCCAATGTGA GCAGCTGAAC CGCAGCGTCG ACGATGTACC ACAGCCACAA   4680

CCATTTCAAC ACCCCCATCT TTACATGATC GCTCATCAGA CTTCTCCTTT CCTAAATATG   4740

GGGTAACGGC AGTATTTCTT ATTTTTTTAA GTTCTTTTTT CTTACCATAA TGTCAAATTC   4800
```

```
TCATATATAG TGAAGTGTTG TCAGTCAGTC ATATAGGCAA TGATAGTGAA TGCACTTCAT      4860

ATATAGGGTT TGTGTTAGGT ATGGCGTTAG AGGTTGATGG TATGCATGCA TATTATTGTA      4920

TTATGATTTT TAATTTGCTA TATATGATTG TAATTTCAGT GGTTTGTACC AAGGAGAAGA      4980

CCAAACGGCG ATGAGGAGGA ACAATCTGGA TCTGACTCTT GAACCCATTT ACAATTACCT      5040

TGGCTGTTAC GCCGCTTGAA TAGACTACAT CGATCTATAT CAATCTCTTT AAAATAATAT      5100

AAGATCGATC CTCTATTCAT GATCTATATT AAACACCGGT TAATTAATAT ATTTTTGGTA      5160

TGTCCTTATA TCATATCAAC ATCATCAAGC CTTTTTCCAA TTCAATATAT CTTGTATTTC      5220

GGGGAGCAAT GAATAAATGT AATATTTGTG GACTGAGAGA GCTAGAAAGA ATTGTTGTTC      5280

AAACCTTTTC TATATTGATC TCATCGTTAC ATTGTAATTT GATTTCTTTC ACACCCCAAA      5340

ATATTTGTAA TACGAATTTA GTCTTTGATG ATTTGAACTT TACTTGGTCA AAGTAAATCA      5400

CAGCCTTAGA AGGTAAATTT TGAATTGAAA ATAGAAATAA AAATGTTGGG AACGTGACAT      5460

TCGGTTTCTT CTCCATTTGC TTCATGTAGG TGCGTGATAC GATCGGAAAT GAGAATTATT      5520

GGGCCCTTGT GGGCTTCATA ATTATTAGTT CATTGTTTAA GCCCATAATA CTTGGCATTT      5580

TTGCCAAAGA AGAAACTGTA TAAAAGAAAT CGGAGAAGAA AAGAAAAATA GTAGTCGCGG      5640

CAATGGAGGA TCTATGGAAG AGGGCAAAAT CGTTCGCAGA AGAAGCGGGT AAGAAGTCTC      5700

AGACGATAAC ACAATCATCC TCCGCGACCT TCGTCAATCT CGTCACCGAG ACTGCTAAGA      5760

AATCCAAGGA ACTCGCTCTC GAAGCTTCGA AGAAAGCTGA TCAATTCAAT GCCGCCGATT      5820

TCGTTGCTGA AACGGCTAAG AAATCCAAAG AATTC                                5855

(2) INFORMATION FOR SEQ ID NO:21:

(i) SEQUENCE CHARACTERISTICS:
        (A) LENGTH: 1120 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: unsure
        (B) LOCATION: 389..393
        (D) OTHER INFORMATION: /note= "N = one or more
            nucleotides."

(ix) FEATURE:
        (A) NAME/KEY: unsure
        (B) LOCATION: 810..814
        (D) OTHER INFORMATION: /note= "N = one or more
            nucleotides."

(ix) FEATURE:
        (A) NAME/KEY: unsure
        (B) LOCATION: 1118..1120
        (D) OTHER INFORMATION: /note= "N = one or more
            nucleotides."

(ix) FEATURE:
        (A) NAME/KEY: misc_feature
        (B) LOCATION: 1..1120
        (D) OTHER INFORMATION: /note= "sequence = Brassica
            oleracea CAL gene"

(xi) SEQUENCE DESCRIPTION: SEQ ID NO:21:

TCTAGATAAT CTTCTCAAGA AGGATTTAGA ATGGCATAAT CCAAAGGCTC AAATCTCGGC        60

ATCTGAAACC ATATTATCAA TTTATTCATG ATTTAGGATG CAACCAATTA AAAATAATCA       120

GTGCATATGA TTTCATAAGT CTCTCGACCA AAACACTTTA CTACTCGATC ATGGTGCGAA       180
```

```
ACAAGTCGAG AATGCTAGGT CTATATGTGA TGCTTAGGCC ACACGGCATG TAATGTGATA      240

CAACGATCCT AGAGATCGGT TCTGAGATAT GCAAGCAAGG TCACACGACC ATTCATATAT      300

GGTGTCTCTC TAGGCCACAC GGCAAGCTAT GATGCATTAA GCCACACGGC TTTCAATCAC      360

ATGATGCAAC AATGTGATCT ATCAAGGGNN NNNCTCGAGC TGCACACAGA CGGACGCGAG      420

CTGGCTGTCG TCGGATGCGA GCTGAACGGG ACGGGACTCG TCTGCTTCCT ATCGGGTTCG      480

CGAGCTGCTT CCTATCGGGT TTTCAAGCGG CTGATCGGGA TTACAAGCTG GTTGATCAGG      540

AACACGAGCT GGCTGTGATG CGAACGGAAG CTGAGGTTGT CTAGGATCAG GAACACCTTA      600

GGGATGGAGC TGATCGGTTG CTGACGAGCT GGAACGCGAG CTAGGACGAA TTAGGGTTCG      660

TCGGATTAG GTTAAAGTCG CCGGCTAGGT TAGGTTTAAG GGATTGGCGA TTTTAGCTTA      720

GATTGCAGAG AACAATCGTG CTGATAACAT GTTGTAATTA GAAGATTGAA GATTGAATAG      780

TTCTGTGTTT TATTAACATA ACATGAATTN NNNNAAAGAT TCCACGAGTT TCGTACATGT      840

TCTATTGCTA GTTAGGTTAA GGGAGTTAAG CAAAGTAGAG TGATTGGCAT TAACTCTTCA      900

GTAGTGCCCA CGAAGACTCT AGTTAGAAGT CAGTTCAATC TGACAAGCTG TTAGAGGTTC      960

ACTAACACTT GAGTTTGGAT CTTGAAGGTC CATATAATAG TATAACGTAG ACCCAATATA     1020

ATACAAAACT ATAGTATTGA CTATAAATTT GAGTGTCTAC ACCAACTCGT TTAAGCAAGA     1080

CAGGTCCCGA GACCGGAGTG GTTTCTTTGT TGAGCTCNNN                           1120

(2) INFORMATION FOR SEQ ID NO:22:

(i) SEQUENCE CHARACTERISTICS:
        (A) LENGTH: 4816 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: unsure
        (B) LOCATION: 700..709
        (D) OTHER INFORMATION: /note= "N = one or more
            nucleotides."

(ix) FEATURE:
        (A) NAME/KEY: unsure
        (B) LOCATION: 3846..3853
        (D) OTHER INFORMATION: /note= "N = one or more
            nucleotides."

(ix) FEATURE:
        (A) NAME/KEY: unsure
        (B) LOCATION: 4545..4548
        (D) OTHER INFORMATION: /note= "N = one or more
            nucleotides."

(ix) FEATURE:
        (A) NAME/KEY: misc_feature
        (B) LOCATION: 1..4816
        (D) OTHER INFORMATION: /note= "sequence = Brassica
            oleracea var. botrytis CAL gene"

(xi) SEQUENCE DESCRIPTION: SEQ ID NO:22:

AAGCTTTAGG GTTTTAGGGT TTTTGATTCC AAGATTTAGG GTTTTCATAA TTCAGATCAG       60

AACAATCAAT CAACATGTTC TAATGAATC GATTTCAATC TAGTGATTAT AAGATGATCA      120

GTTTTAGGTT ATACCAATTT TTAGGATTTA TCAAGATCAT TGGATTTCCA TAATAATGGA      180

TTAGGGTTTT AGGGTTTGAT CATTATGTTT TTAGATTAAT CGGTATACTT TTGTTTGTAG      240

GGTTGAAACC GGACCACCAA AGAGAACGGA TGAACCTCGA GCTGCACACC GACAGATGCG      300
```

```
AGCTGGCTGT CGTCGGATGC GAGCTGAACG GGACGGGACG CGTCTGCTTC CTATCGGGTT      360

CGCGAGCTGC TTCCTATCGG GTTTGCAAGC GGCTGATCGG GATTGCGAGC TGGTTGATCG      420

GGAACACGAG CTGGCTGTGA TGCGAACGGA AGCTGAGGTC GTCTAGGATC AGGAACACCT      480

TAGGGATGGA GCTGATCGGT TGCTGACGAG CTGGAACGCG AGCTAGGACA AATTAGGGTT      540

CGTCGGGATT AGGTTAAAGT CGCCGGCTAG GTTAGGTTTA AGGGATTGGC GATTTTAGCT      600

TAGATTGCAG AGAACAATCG TGCTGATAAC GTGTTGTAAA ACAAACGGTT TTAGAAACTG      660

AATGTTTATG TGTATTATTA ATCATAATAT GGGTTTTTTN NNNNNNNNNT ACAGTGCGAG      720

AATGATAGAC TCGCATAGCC AATGAAGTCC AGTCAGACCA ATGAGAAGTC GACAGCAAAA      780

CCTAGTAAAC TACTCTTGTT TTATCCTTGT CCAAAACCAG CTTTAGGTTT CCCTGAAACC      840

GCTTATTCCA AAACATCTTC TCCTTAAATA AGAAAGACT CTTTCACATT GTTATTATCA       900

TCAGAAGGGA AAGAAGAAAA ACTTTCCTAA TTAGATCGAG CTTGTCGTTA TCTCTCTATT      960

ATAGTTTATA TTTCTTACTG GGCTTGTTT GGTTGCTTCT CTTTTTGGAC TTCTTTTATA      1020

TAATTTATAT ATTCTACGAG AAATGGGAAG GGGTAGGGTT GAAATGAAGA GGATAGAGAA     1080

CAAGATCAAC AGACAAGTGA CGTTTTCGAA AAGAAGAGCT GGTCTTTTGA AGAAAGCCCA     1140

TGAGATCTCG ATTCTTTGTG ATGCTGAGGT TTCCCTTATT GTCTTCTCCC ATAAGGGGAA     1200

ACTGTTCGAG TACTCGTCTG AATCTTGGTA ACTGCATAAT TCCCTTTTTA ATTGTTTTAG     1260

TGTGCCTTTG TTCGCCCTAA TAAATAGTTT TTGTTCTCCT TTAGGCCATT TCTTGGTATC     1320

TTCTTATGTT TTTATGAAAA TTCTCACAAA TTTTGTAGTT AATTACTTGG ATCTACGAAT     1380

TGATTTCACC AAAGTGAAAT TAAACCATTA TAGCATATTT GCTTATATCA GAAGAAAATA     1440

AAAAAAATAG GCATAATAA GGTGTTATGT GAAGTGAAAG TTTACTTCAG GTAACACGTT      1500

ATTAAGATAT GCTTAACCCT AGATCAAGAT CTACTTCTAC TGGTCGCGAC ATGGATTTAC     1560

AAGAAATCGT CACTGTATAT GAACTTTAAT TTAAACATGT ATAGACCTTT TTGTTTCAAA     1620

TAGAGAGTTA AGTAATTTAA TCATAGAAAG AACCAACGTT ATGTTCATCT AGGCTAGAGT     1680

GATTTTTGCC TAACAATTTT GAAAAGCTGT CCTTATGCTT AAATATCTTT CAGCAGCATA     1740

GTAGTATGAA AGAAAATATT TCAATATCGT TGTATAAAGG TTCTATAATT TTCGTTTTTT     1800

TTTTTTTCGC AAATGGTTTA TATAGAGAAA CTAGAACTAG GGATGTGACA TCTAGGTATA     1860

GGGGTCTTTG ACCTCTGGGA TCAATGTAAA AGAGACCATT CTATTTTCTA TCAACTTCTC    1920

AGTTTCCGAT GGTCAAAACT TAACTTCAAC AACTGTTTTT CTTTTCAGAA GAGGACAAAC    1980

TATTATATGT ATATTATGTT ATGTCGTTTC ATACATAAAT ATCTAATAAC AAATTTATTT    2040

TTAAAAACAT ATAACAAAAC TTTATTGAAG AATTGGAAAC TCAAACGGG GACATATAGG     2100

ACGCTGCACG TCTAGAGGTG TGGGGTTAGT GATTCAACGG GTTTTAATG TAGAGAAACT     2160

GTAGATGTAA GATTGTTTCT AGGGTTAAGG CACTAAACCA GGGATTATCT CTTTTCCATG    2220

ATAAAGTTA ATGTCTTAAA TGCATCGCTA ATTAATTAGG CAAACTAGAT GATAGTACGT     2280

AGTGTGTGTG TGTGTGTGTA TTGGATATTT TGGGTTAATA GTTACATCTT AGACAAATGT    2340

GTGGTCTTCT GATAAGCTGA GAAAATATTT GGGTGCAGAC TCTTAGTGGT AATTAATTAT    2400

ATCTAGAAAN NCCANATAC NAATTTAATA CGGCTACTTT TTGGGTGAAT GAATCTACAC     2460

TAACCCTAAG CCTAATGATA GCATGGAGAA GGTACTAGAA CGCTACGAGA GGTACTCTTA    2520

CGCCGAGAAA CAGCTAAAAG CTCCAGACTC TCACGTCAAT GTATGTTTAA TGATCTCCAA    2580

GACTCTGTCA AACATATATG TACTATATCT TGAATGTGTT TTCTTAATTA ACATAATTGA    2640
```

```
TGCACTGTTT ACATAATGAA AATTAATTGT GTAGGCACAA ACGAACTGGT CAATGGAATA       2700

TAGCAGGCTT AAGGCTAAGA TTGAGCTTTG GGAGAGGAAC CAAAGGTACT TATAGAATTT       2760

AGGAATTAGC ATGTGTAAAT AATAGTTTAT TGTATTAGTT TTTTTTGGTA AAATTATTGT       2820

ATTAGTTAAA CACTGGGAAT TAACAAAAAA GATGGTGGTA TGGATTAATC ATAGGCATTA       2880

TCTGGGAGAA GATTTAGAAT CAATCAGCAT AAAGGAGCTA CAGAATCTGG AGCAGCAGCT       2940

TGACACTTCT CTTAAACATA TTCGCTCCAG AAAAGTGTGT AAATAAGCAC ATACAAACGC       3000

AAACATCTCT ATCTTATCTT TGAGTTTGTG AAGATATATA TGCCTAATTT TATATAGAGT       3060

TTGTCTCATA TGAATGAATA CAATTTGAAC TCAATTGTAT GCAGAATCAA CTAATGCACT       3120

AGTCCCTCAA CCACCTCCAA AGAAAGGTAC GTTAAAACCA TTTCATCTCT CAAGTCGTAC       3180

GTGTGTATGT GTGACTTATG TTACCGTTTA AATCTTTCAG TTAAATACAA AACATATGGT       3240

TTTACACATG TTAGACTATT TTGGTGAAGG AAACATTGTA AATGTAAACA AAGGGGTTTT       3300

TTGGATTGAA TAAAATTTAA CATTCATTCA AAAAAAACAT ATGGTTCATA TATATATTCG       3360

GTTTATATGA TTATATATAT ATATTTATAT AGGTTAATAT ATTAGTGTTT AATTATATGT       3420

GTATACATAT AGATGTAGAA AGAACCTCTA GAGCGATCCC TGAGAATTGT TTCATTTTGT       3480

AAAATTGACA GGAGAAAGAA ATACTGGAGG AAAACAGCAT GCTTGCCAAA CAGGTAATCA       3540

TTGTATGTTG CATTTTTTAC TGTTTCACAA CTGTTTTACT ATTTAAACTC CACTGTTCTA       3600

CTCCACTTCA ACCTTAAACT ACCATTGCTC AACTTTCGGC ACCAACTCTT TTTTAAAAAG       3660

GAAGAATTAG TTGTTTCATG TGATTGGTAT AATCATGAGC ATATGTGCAC ACATGTAGGT       3720

GGGCTTTGTC CGTTTAGTAT TAAGGTTGTC TCCTAGAATT GAACTTGAAC TGTCTTCTCG       3780

TAATCATAGT CTATATATAA CACGCTGCAC ATACAGTAGC CAGTAGGTTT ATTTGAGCAA       3840

GATACNNNNN NNNTGCTCTT ACTGTAATAC CGTGCCAACA TTGATTGTGA TTCGATACAT       3900

AAATTTAGTT GATCATAACG TTTATCGGTA TTTGAAATTG GTAGATAAAG GAGAGGGAGA       3960

GTATCCTAAG GACACATCAA AACCAATCAG AGCAGCAAAA CCGCAGCCAC CATGTAGCTC       4020

CTCAGCCGCA ACCGCAGTTA AATCCTTACA TGGCATCATC TCCTTTCCTA AATATGGGGT       4080

AACGGTAGTG TTTCATTTTT ATCTTGGTAT ACATATATAC ATATAGATCC GACACTCTTG       4140

GTGTTAGTAA TTCAGTGTAT GCGATGATGT TGTATGTATG TATGTTCATA TTTAGGGTTT       4200

GTGTTAAGTG TGGCGTTAGA GGTTGATGGC TTTGTAACTA CATGTCTAGA ACTATACAAT       4260

AATTAATAAG ATGAATGAT ATATATATAT ACATATATTT TAATTTGCCA TATGATTGTG       4320

ATTTCAGTGG CATGTACCAA GGAGAATATC CAACGGCGGT GAGGAGGAAC CGTCTCGATC       4380

TGACTCTTGA ACCCATTTAC AACTGCAACC TTGGTTACTT TGCCGCATGA ATGGACTCGC       4440

CATATATCGA CATAAAATAA TTTATATAAG ATCGATTTTT ACGTATAATA ATAGGCAGCA       4500

ATGGTTAGCC ACCATATCTA TATACACTGG AAATTCTATT TATCNNNNTT ACATTGATTT       4560

ATACTACATA AACCCTCCAG ACCAAACTCG TCTCCATGCC AACTGATAGA TTTCCTAGAC       4620

ATGCTACACA CTCCATGACT CCGACTAATT TTTGGTTTGG CGTTTTCTAT GTTTTTATTA       4680

ATTGTTTTGA ATTTTACTCT TTCACGATAT TTAAAATTTT TCAAACTTAT TTTTGTTGCT       4740

CACAGTGAAC AAATCTTCTG TGAAGAAGTG GTATATATTC TGTGGAGCCA CTTCCCCAAT       4800

GTTCTTTGGT GGATCC                                                      4816
```

(2) INFORMATION FOR SEQ ID NO:23:

(i) SEQUENCE CHARACTERISTICS:
        (A) LENGTH: 855 base pairs

```
            (B) TYPE: nucleic acid
            (C) STRANDEDNESS: double
            (D) TOPOLOGY: linear (ix) FEATURE:
            (A) NAME/KEY: CDS
            (B) LOCATION: 1..853

(ix) FEATURE:
            (A) NAME/KEY: misc_feature
            (B) LOCATION: 1..855
            (D) OTHER INFORMATION: /note= "product = Rat
                glucocorticoid receptor ligand binding domain"

(xi) SEQUENCE DESCRIPTION: SEQ ID NO:23:

ACA AAG AAA AAA ATC AAA GGG ATT CAG CAA GCC ACT GCA GGA GTC TCA        48
Thr Lys Lys Lys Ile Lys Gly Ile Gln Gln Ala Thr Ala Gly Val Ser
  1               5                  10                  15

CAA GAC ACT TCG GAA AAT CCT AAC AAA ACA ATA GTT CCT GCA GCA TTA        96
Gln Asp Thr Ser Glu Asn Pro Asn Lys Thr Ile Val Pro Ala Ala Leu
             20                  25                  30

CCA CAG CTC ACC CCT ACC TTG GTG TCA CTG CTG GAG GTG ATT GAA CCC       144
Pro Gln Leu Thr Pro Thr Leu Val Ser Leu Leu Glu Val Ile Glu Pro
         35                  40                  45

GAG GTG TTG TAT GCA GGA TAT GAT AGC TCT GTT CCA GAT TCA GCA TGG       192
Glu Val Leu Tyr Ala Gly Tyr Asp Ser Ser Val Pro Asp Ser Ala Trp
     50                  55                  60

AGA ATT ATG ACC ACA CTC AAC ATG TTA GGT GGG CGT CAA GTG ATT GCA       240
Arg Ile Met Thr Thr Leu Asn Met Leu Gly Gly Arg Gln Val Ile Ala
 65                  70                  75                  80

GCA GTG AAA TGG GCA AAG GCG ATA CTA GGC TTG AGA AAC TTA CAC CTC       288
Ala Val Lys Trp Ala Lys Ala Ile Leu Gly Leu Arg Asn Leu His Leu
                 85                  90                  95

GAT GAC CAA ATG ACC CTG CTA CAG TAC TCA TGG ATG TTT CTC ATG GCA       336
Asp Asp Gln Met Thr Leu Leu Gln Tyr Ser Trp Met Phe Leu Met Ala
            100                 105                 110

TTT GCC TTG GGT TGG AGA TCA TAC AGA CAA TCA AGC GGA AAC CTG CTC       384
Phe Ala Leu Gly Trp Arg Ser Tyr Arg Gln Ser Ser Gly Asn Leu Leu
        115                 120                 125

TGC TTT GCT CCT GAT CTG ATT ATT AAT GAG CAG AGA ATG TCT CTA CCC       432
Cys Phe Ala Pro Asp Leu Ile Ile Asn Glu Gln Arg Met Ser Leu Pro
    130                 135                 140

TGC ATG TAT GAC CAA TGT AAA CAC ATG CTG TTT GTC TCC TCT GAA TTA       480
Cys Met Tyr Asp Gln Cys Lys His Met Leu Phe Val Ser Ser Glu Leu
145                 150                 155                 160

CAA AGA TTG CAG GTA TCC TAT GAA GAG TAT CTC TGT ATG AAA ACC TTA       528
Gln Arg Leu Gln Val Ser Tyr Glu Glu Tyr Leu Cys Met Lys Thr Leu
                165                 170                 175

CTG CTT CTC TCC TCA GTT CCT AAG GAA GGT CTG AAG AGC CAA GAG TTA       576
Leu Leu Leu Ser Ser Val Pro Lys Glu Gly Leu Lys Ser Gln Glu Leu
            180                 185                 190

TTT GAT GAG ATT CGA ATG ACT TAT ATC AAA GAG CTA GGA AAA GCC ATC       624
Phe Asp Glu Ile Arg Met Thr Tyr Ile Lys Glu Leu Gly Lys Ala Ile
        195                 200                 205

GTC AAA AGG GAA GGG AAC TCC AGT CAG AAC TGG CAA CGG TTT TAC CAA       672
Val Lys Arg Glu Gly Asn Ser Ser Gln Asn Trp Gln Arg Phe Tyr Gln
    210                 215                 220

CTG ACA AAG CTT CTG GAC TCC ATG CAT GAG GTG GTT GAG AAT CTC CTT       720
Leu Thr Lys Leu Leu Asp Ser Met His Glu Val Val Glu Asn Leu Leu
225                 230                 235                 240

ACC TAC TGC TTC CAG ACA TTT TTG GAT AAG ACC ATG AGT ATT GAA TTC       768
Thr Tyr Cys Phe Gln Thr Phe Leu Asp Lys Thr Met Ser Ile Glu Phe
                245                 250                 255
```

```
CCA GAG ATG TTA GCT GAA ATC ATC ACT AAT CAG ATA CCA AAA TAT TCA      816
Pro Glu Met Leu Ala Glu Ile Ile Thr Asn Gln Ile Pro Lys Tyr Ser
            260                 265                 270

AAT GGA AAT ATC AAA AAG CTT CTG TTT CAT CAA AAA T GA                 855
Asn Gly Asn Ile Lys Lys Leu Leu Phe His Gln Lys
        275                 280
```

(2) INFORMATION FOR SEQ ID NO:24:

(i) SEQUENCE CHARACTERISTICS:
        (A) LENGTH: 284 amino acids
        (B) TYPE: amino acid
        (D) TOPOLOGY: linear (ii) MOLECULE TYPE: protein (xi) SEQUENCE DESCRIPTION: SEQ ID NO:24:

```
Thr Lys Lys Ile Lys Gly Ile Gln Gln Ala Thr Ala Gly Val Ser
 1               5                  10                  15

Gln Asp Thr Ser Glu Asn Pro Asn Lys Thr Ile Val Pro Ala Ala Leu
            20                  25                  30

Pro Gln Leu Thr Pro Thr Leu Val Ser Leu Leu Glu Val Ile Glu Pro
        35                  40                  45

Glu Val Leu Tyr Ala Gly Tyr Asp Ser Ser Val Pro Asp Ser Ala Trp
 50                  55                  60

Arg Ile Met Thr Thr Leu Asn Met Leu Gly Gly Arg Gln Val Ile Ala
 65                  70                  75                  80

Ala Val Lys Trp Ala Lys Ala Ile Leu Gly Leu Arg Asn Leu His Leu
                85                  90                  95

Asp Asp Gln Met Thr Leu Leu Gln Tyr Ser Trp Met Phe Leu Met Ala
            100                 105                 110

Phe Ala Leu Gly Trp Arg Ser Tyr Arg Gln Ser Ser Gly Asn Leu Leu
        115                 120                 125

Cys Phe Ala Pro Asp Leu Ile Ile Asn Glu Gln Arg Met Ser Leu Pro
    130                 135                 140

Cys Met Tyr Asp Gln Cys Lys His Met Leu Phe Val Ser Ser Glu Leu
145                 150                 155                 160

Gln Arg Leu Gln Val Ser Tyr Glu Glu Tyr Leu Cys Met Lys Thr Leu
                165                 170                 175

Leu Leu Leu Ser Ser Val Pro Lys Glu Gly Leu Lys Ser Gln Glu Leu
            180                 185                 190

Phe Asp Glu Ile Arg Met Thr Tyr Ile Lys Glu Leu Gly Lys Ala Ile
        195                 200                 205

Val Lys Arg Glu Gly Asn Ser Ser Gln Asn Trp Gln Arg Phe Tyr Gln
    210                 215                 220

Leu Thr Lys Leu Leu Asp Ser Met His Glu Val Val Glu Asn Leu Leu
225                 230                 235                 240

Thr Tyr Cys Phe Gln Thr Phe Leu Asp Lys Thr Met Ser Ile Glu Phe
                245                 250                 255

Pro Glu Met Leu Ala Glu Ile Ile Thr Asn Gln Ile Pro Lys Tyr Ser
            260                 265                 270

Asn Gly Asn Ile Lys Lys Leu Leu Phe His Gln Lys
        275                 280
```

(2) INFORMATION FOR SEQ ID NO:25:

(i) SEQUENCE CHARACTERISTICS:

```
        (A) LENGTH: 20 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1..20
        (D) OTHER INFORMATION: /note= "sequence name = AGL10-1"

(xi) SEQUENCE DESCRIPTION: SEQ ID NO:25:

GATCGTCGTT ATCTCTCTTG                                                    20

(2) INFORMATION FOR SEQ ID NO:26:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1..19
        (D) OTHER INFORMATION: /note= "sequence name = ALG10-12"

(xi) SEQUENCE DESCRIPTION: SEQ ID NO:26:

GTAGTCTATT CAAGCGGCG                                                     19

(2) INFORMATION FOR SEQ ID NO:27:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1..19
        (D) OTHER INFORMATION: /note= "sequence name = ALG10-2"

(xi) SEQUENCE DESCRIPTION: SEQ ID NO:27:

GATGGAGACC ATTAAACAT                                                     19

(2) INFORMATION FOR SEQ ID NO:28:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1..18
        (D) OTHER INFORMATION: /note= "sequence name = AGL10-3"

(xi) SEQUENCE DESCRIPTION: SEQ ID NO:28:

GGAGAAGGTA CTAGAACG                                                      18

(2) INFORMATION FOR SEQ ID NO:29:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ix) FEATURE:
        (A) NAME/KEY: misc_feature
```

```
          (B) LOCATION: 1..18
          (D) OTHER INFORMATION: /note= "sequence name = ALG10-4"

(xi) SEQUENCE DESCRIPTION: SEQ ID NO:29:

GCCCTCTTCC ATAGATCC                                                       18

(2) INFORMATION FOR SEQ ID NO:30:

(i) SEQUENCE CHARACTERISTICS:
          (A) LENGTH: 19 base pairs
          (B) TYPE: nucleic acid
          (C) STRANDEDNESS: single
          (D) TOPOLOGY: linear (ix) FEATURE:
          (A) NAME/KEY: misc_feature
          (B) LOCATION: 1..19
          (D) OTHER INFORMATION: /note= "sequence name = BOB1"

(xi) SEQUENCE DESCRIPTION: SEQ ID NO:30:

TCTACGAGAA ATGGGAAGG                                                      19

(2) INFORMATION FOR SEQ ID NO:31:

(i) SEQUENCE CHARACTERISTICS:
          (A) LENGTH: 19 base pairs
          (B) TYPE: nucleic acid
          (C) STRANDEDNESS: single
          (D) TOPOLOGY: linear (ix) FEATURE:
          (A) NAME/KEY: misc_feature
          (B) LOCATION: 1..19
          (D) OTHER INFORMATION: /note= "sequence name = BOB2"

(xi) SEQUENCE DESCRIPTION: SEQ ID NO:31:

GTCGATATAT GGCGAGTCC                                                      19

(2) INFORMATION FOR SEQ ID NO:32:

(i) SEQUENCE CHARACTERISTICS:
          (A) LENGTH: 19 base pairs
          (B) TYPE: nucleic acid
          (C) STRANDEDNESS: single
          (D) TOPOLOGY: linear (ix) FEATURE:
          (A) NAME/KEY: misc_feature
          (B) LOCATION: 1..19
          (D) OTHER INFORMATION: /note= "sequence name = BOB4B"

(xi) SEQUENCE DESCRIPTION: SEQ ID NO:32:

CCATTGACCA GTTCGTTTG                                                      19

(2) INFORMATION FOR SEQ ID NO:33:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (ix) FEATURE:
          (A) NAME/KEY: misc_feature
          (B) LOCATION: 1..18
          (D) OTHER INFORMATION: /note= "sequence name = BOB33"

(xi) SEQUENCE DESCRIPTION: SEQ ID NO:33:

GCTCCAGACT CTCACGTC                                                       18
```